United States Patent
Garb et al.

(10) Patent No.: US 12,202,864 B2
(45) Date of Patent: Jan. 21, 2025

(54) SILK NUCLEOTIDES AND PROTEINS AND METHODS OF USE

(71) Applicants: University of Massachusetts, Boston, MA (US); The University of Akron, Akron, OH (US); The University of Vermont and State Agricultural College, Burlington, VT (US)

(72) Inventors: Jessica Garb, Arlington, MA (US); Todd A. Blackledge, Akron, OH (US); Ingi Agnarsson, South Burlington, VT (US)

(73) Assignees: UNIVERSITY OF MASSACHUSETTS, Boston, MA (US); THE UNIVERSITY OF VERMONT AND STATE AGRICULTURAL COLLEGE, Burlington, VT (US); THE UNIVERSITY OF AKRON, Akron, OH (US)

( * ) Notice: Subject to any disclaimer, the term of this patent is extended or adjusted under 35 U.S.C. 154(b) by 846 days.

(21) Appl. No.: 17/286,898

(22) PCT Filed: Oct. 31, 2019

(86) PCT No.: PCT/US2019/059165
§ 371 (c)(1),
(2) Date: Apr. 20, 2021

(87) PCT Pub. No.: WO2020/092769
PCT Pub. Date: Aug. 7, 2020

(65) Prior Publication Data
US 2022/0119462 A1    Apr. 21, 2022

Related U.S. Application Data

(60) Provisional application No. 62/771,210, filed on Nov. 26, 2018, provisional application No. 62/753,126, filed on Oct. 31, 2018.

(51) Int. Cl.
*C07K 14/435* (2006.01)
*A61L 27/22* (2006.01)

(52) U.S. Cl.
CPC ...... *C07K 14/43518* (2013.01); *A61L 27/227* (2013.01); *C07K 2319/00* (2013.01)

(58) Field of Classification Search
CPC .......... C07K 14/43518; C07K 2319/00; A61L 27/227
See application file for complete search history.

(56) References Cited

U.S. PATENT DOCUMENTS

| 9,051,383 B2 * | 6/2015 | Hayashi ........... C07K 14/43518 |
| 2020/0285070 A1 | 9/2020 | Neuman |
| 2023/0042322 A1 * | 2/2023 | Ittah ..................... D01D 5/0038 |

FOREIGN PATENT DOCUMENTS

| WO | 2017138002 A1 | 8/2017 |
| WO | 20180022016 A1 | 1/2018 |

OTHER PUBLICATIONS

International Search Report and Written Opinion for International Application PCT/US2019/059165; International Filing Date: Oct. 31, 2019; Date of Mailing: May 29, 2020; 11 pages.

* cited by examiner

*Primary Examiner* — Maria G Leavitt
*Assistant Examiner* — Joel D Levin
(74) *Attorney, Agent, or Firm* — CANTOR COLBURN LLP

(57) ABSTRACT

An engineered polypeptide includes at least two units, wherein each unit includes a polypeptide of SEQ ID NO: 4, a polypeptide of SEQ ID NO: 5, a polypeptide with 90% or greater homology to SEQ ID NO: 4, or a polypeptide with 90% or greater homology to SEQ ID NO: 5, wherein the engineered polypeptide does not comprise SEQ ID NO: 12 or SEQ ID NO: 13. Further described is a synthetic materials including the peptides. Also included are synthetic materials including polypeptide of any one of SEQ ID NOs: 9-32, a polypeptide with 90% or greater homology any one of SEQ ID NOs: 9-32, a polypeptide encoded by any one of SEQ ID NOs. 57-79, or a polypeptide with 90% or greater homology to a polypeptide encoded by any one of SEQ ID NOs. 57-79.

9 Claims, 5 Drawing Sheets
Specification includes a Sequence Listing.

SILK NUCLEOTIDES AND PROTEINS AND METHODS OF USE

CROSS REFERENCE TO RELATED APPLICATIONS

This application is a National Stage application of PCT/US2019/059165, filed Oct. 31, 2019, which claims the benefit of priority to U.S. Provisional Application No. 62/771,210, filed Nov. 26, 2018, and U.S. Provisional Application No. 62/753,126, filed Oct. 31, 2018, both of which are incorporated by reference in their entirety herein.

STATEMENT REGARDING FEDERALLY SPONSORED RESEARCH & DEVELOPMENT

This invention was made with government support under IOS1656645, IOS 1656458 and IOS 1656460 awarded by the National Science Foundation. The government has certain rights in the invention.

FIELD OF THE DISCLOSURE

The present disclosure is related to silk proteins from Darwin's bark spider (*Caerostris darwini*) and methods of use thereof.

BACKGROUND

Spider silks are the toughest materials in nature due to combined strength and extensibility, leading to enormous interest in engineering silk-based biomaterials for industrial applications. Among the seven silk types spun by orb-weaving spiders, dragline from major ampullate (MA) glands is the most studied for its high tensile strength and toughness, which functions to dissipate kinetic energy from flying prey in web radial and frame lines.

What is needed are novel proteins from spider silks and biomaterials containing the novel proteins.

BRIEF SUMMARY

In one aspect, an engineered polypeptide comprises at least two units, wherein each unit comprises a polypeptide of SEQ ID NO: 4, a polypeptide of SEQ ID NO: 5, a polypeptide with 90% or greater homology to SEQ ID NO: 4, or a polypeptide with 90% or greater homology to SEQ ID NO: 5, wherein the engineered polypeptide does not comprise SEQ ID NO: 12 or SEQ ID NO: 13.

In another aspect, a synthetic material comprises the engineered polypeptide described above.

In yet another aspect, a synthetic material comprises a polypeptide of any one of SEQ ID NOs: 9-32, a polypeptide with 90% or greater homology any one of SEQ ID NOs: 9-32, a polypeptide encoded by any one of SEQ ID NOs. 57-79, or a polypeptide with 90% or greater homology to a polypeptide encoded by any one of SEQ ID NOs. 57-79.

In a further aspect, a synthetic material comprises a polypeptide comprising SEQ ID NO: 4, a polypeptide comprising SEQ ID NO: 5, a polypeptide with 90% or greater homology to SEQ ID NO: 4, or a polypeptide with 90% or greater homology to SEQ ID NO: 5, wherein the synthetic material is not found in nature.

Figure 1:
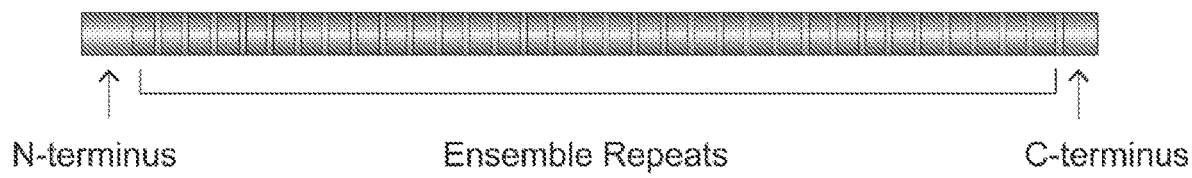
FIG. 1 shows a schematic of spider silk proteins (spidroins) composed of tandem-repeated amino acid sequences (ensemble repeats) flanked by non-repetitive amino (N)- and carboxy (C-) terminal domains.

The above-described and other features will be appreciated and understood by those skilled in the art from the following detailed description, drawings, and appended claims.

DETAILED DESCRIPTION

The dragline silk of the Darwin's bark spider (*Caerostris darwini*) from Madagascar is twice as tough as all other silks measured (354±93 MJ/m$^3$) and 10-fold tougher than Kevlar due to its unusual extensibility (91% its length). Extraordinarily tough dragline is hypothesized to be adaptive for *C. darwini* because it constructs the largest recorded orb webs, up to 2.8 m$^2$, suspended by bridgelines up to 25 meters across rivers, capturing prey inaccessible to most predators. The toughness of *C. darwini* dragline comes from increased extensibility relative to other draglines, while retaining strength. Moreover, *C. darwini* silk proteins present innovative designs for novel biomaterials. Here we show *C. darwini* MA glands highly express a novel silk protein (MaSp4) that diverges markedly from closely related dragline proteins, being largely comprised of GPGPQ amino acid motifs similar to those known to confer fiber extensibility. Analyses indicate MaSp4 is derived from typical dragline (MaSp) genes, suggesting *C. darwini* evolved unique proteins that increased its dragline's toughness. *C. darwini*'s MA gland spinning ducts are also unusually long, which may facilitate intermolecular alignment of silk proteins into extremely tough fibers. Thus, a suite of novel traits from the level of genes to spinning physiology to silk biomechanics are associated with the unique ecology of Darwin's bark spider.

Spider silks are formed from spidroins, a family of repetitive structural proteins exhibiting differing expression among the diverse toolkit of spider silk glands. The amino acid motifs composing spidroin repeats are highly variable, generating the distinctive mechanical and functional properties of each silk type. Repetitive regions are flanked by amino (N) and carboxy (C)-terminal domains critical for fiber assembly that also serve as phylogenetic markers. Orb-weaver dragline is primarily comprised of MA spidroins MaSp1 and MaSp2, both having repetitive regions containing beta-sheet forming poly-alanine ($A_n$) amino acid motifs that contribute to tensile strength by stacking into nanocrystals. Unlike MaSp1, MaSp2 also contains many $GPGX_1$ motifs ($X_1$=G, S, A or Q) (SEQ ID NO: 53), which form beta-turns supplying dragline extensibility. Many $GPGX_1$ and fewer $A_n$ motifs are in Flag, the spidroin contributing the orb web's highly elastic capture spiral silk, where $GPGX_1$-forming beta-turns assemble into "nano-springs", allowing 1000% reversible extensibility. Here we show that *C. darwini* dragline silk contains novel silk proteins that likely explain the greater extensibility, and hence toughness, of its dragline relative to other orb-weavers.

The polypeptides of the present disclosure can be described as follows.

SEQ ID NOs. 1-7 as provided in Table 1 are the consensus sequence units for the *C. darwini* dragline spidroin (MaSp) proteins:

SEQ ID NO: 8 shows the repeat units of the MaSp4a sequence. Additional sequences are provided in Tables 2-4. Table 2 provides the longest protein sequences for each *C. darwini* spidroin C-terminal cluster. These sequences were used in protein analyses. The name begins with name used in main text, figures and tables, followed by transcript translated from, those with names beginning with "c" derived from Iso-Seq assembly, those starting with "TR" derived from Illumina® assembly. A name containing "RC" has coding sequence translated in reverse complement direction.

TABLE 2

Longest identified protein sequences for each *C. darwini* spidroin C-terminal cluster

| SEQ ID NO: | Description | SEQ ID NO: for corresponding polynucleotide sequence |
|---|---|---|
| 9 | MaSp2_c6135_f1p11_2123 | 57 |
| 10 | MaSp1a_c23000_f4p48_1723 | 58 |
| 11 | MaSp1b_c18326/f3p41/1509 | 59 |
| 12 | MaSp4a_c26805_f1p25_2132 | 60 |
| 13 | MaSp4b_c19205_f1p0_1636 | 61 |
| 14 | MaSp1c_c31462_f1p21_1336 | 62 |
| 15 | MaSp5_c20015_f4p27_1444 | 63 |
| 16 | MiSp1_TR41386_c0_g1_i1 | 64 |
| 17 | Flag_RC_TR56526_c0 g1_i1 length = 1619 | 65 |
| 18 | TuSp1_TR23580_c0_g2_i2 length = 1093 | 66 |
| 19 | MiSp2_RC_TR78167_c0_g3_i1 length = 925 | 67 |
| 20 | PySp_TR732771c0_g1_i1 | 68 |

TABLE 1

Consensus sequence units

| SEQ ID NO: | Description | Sequence | Minimum Number of Repeats in Natural Protein |
|---|---|---|---|
| 1 | MaSp2 | GGYGPGGQGPSGPGSQGPGGAGPYGPGGAA AAAAAA | 14 |
| 2 | MaSp1a | $X_1$GGLGGQGGGQX$_{12}$QGGYGSGX$_{20}$GGX$_{23}$GX$_{25}$ GX$_{27}$AAAAAAA<br>$X_1$ is GGA or GGAGGA<br>$X_{12}$ is GAG or GAG GAG<br>$X_{20}$ is L or Q<br>$X_{23}$ is L or Q<br>$X_{23}$ is A or G<br>$X_{27}$ is A or S | 11 |
| 3 | MaSp1b | GGAGGAGGLGGQGGGQGAGQGGYGSGQGGQ GAGX$_{34}$AAAAAAA<br>$X_{34}$ is A or S | 10 |
| 4 | MaSp4a | GPGPQGPSGPGPQGPYGPGPQGPGPQGPGP QGPSGPGPQRPQGPGPQGPYGPGGVSVVSX$_{60}$ TVS<br>$X_{60}$ is A or T | 9 |
| 5 | MaSp4b | GPGPQGPSGPGPQGPYGPGPQGPGPQGPGP QGPGPQGPGPX$_{41}$GPSGPGPQGPYGPGGVSV VSASVS<br>$X_{41}$ is Q or R | 6 |
| 6 | MaSp1c | GSGGDGSGSGGYGGRGGQGGAGSSSAAAAA | 8 |
| 7 | MaSp5 | GGLGGSG | 46 |

TABLE 2-continued

Longest identified protein sequences for each *C. darwini* spidroin C-terminal cluster

| SEQ ID NO: | Description | SEQ ID NO: for corresponding polynucleotide sequence |
|---|---|---|
| 21 | AcSp_TR330341c0_g1_i2 | 69 |
| 22 | AgSp_TR660831c0_g1_i1 | 70 |

Table 3 provides the N terminal clusters. Longest exemplars per cluster containing N-termini (Sequences contain no-C-terminus).

TABLE 3

N terminal clusters

| SEQ ID NO: | Description | SEQ ID NO: for corresponding polynucleotide sequence |
|---|---|---|
| 23 | MaSp4a_RC_TR60988_c2_g1_i1 | 71 |
| 24 | MaSp2_RC_TR18301_c2_g3_i1 | 72 |
| 25 | Fibroin1_MaSp1-like_N-term_TR44210_c2_g2_i1 | 73 |
| 26 | Fibroin2_MaSp5-like_N-term_TR55725_c2_g1_i | 74 |
| 27 | Fibroin3_MaSp1-like_Nterm_TR67764_c0_g1_i1 | 75 |
| 28 | PySp_Nterm_TR121361c0_g1_i1_len = 1230 | 76 |

Table 4 provide the longest "short isoforms" per type including N and C-terminal domains.

TABLE 4

Longest "short isoforms" per type including N and C-terminal domains

| SEQ ID NO: | Description | SEQ ID NO: for corresponding polynucleotide sequence |
|---|---|---|
| 29 | MaSp2_c24257_f1p13_1860_Nterm_Cterm length = 593 | 77 |
| 30 | MaSp4a_c16597_f1p7_1747_Nterm_Cterm length = 504 | 78 |
| 31 | MaSp4b_c13621_f1p2_1363_Nterm_Cterm length = 401_Nterm | 79 |

SEQ ID NO: 32 is an additional long Piriform spidroin lacking N and C-terminal domains (only repetitive sequence) identified from blast annotations in Illumina® transcriptomes.

Described herein are *C. darwini* spider silk polypeptides and methods of use thereof. In an aspect, the polypeptide is a MaSp4a polypeptide comprising the consensus sequence of SEQ ID NO: 4, or a MaSp4b polypeptide comprising the consensus sequence of SEQ ID NO: 5. In an aspect, the MaSp4a polypeptide or MaSp4b polypeptide does not comprise a sequence found in nature, such as SEQ ID NO: 12 or SEQ ID NO: 13.

Also described herein are engineered polypeptides, wherein an engineered polypeptide comprises a polypeptide of SEQ ID NO: 4, a polypeptide of SEQ ID NO: 5, a polypeptide with 90% or greater homology, specifically 95% or greater homology to SEQ ID NO: 4, or a polypeptide with 90% or greater homology, specifically 95% or greater homology to SEQ ID NO: 5, wherein the engineered polypeptide does not comprise SEQ ID NO: 12 or SEQ ID NO: 13. As used herein, an "engineered polypeptide" is a non-natural peptide, that is, a peptide that does not correspond to an amino acid sequence that is found in nature. Engineered polypeptides can be produced by chemical synthesis methods or recombinant DNA technology.

In an aspect, the engineered polypeptide further comprises an N-terminal sequence having 90% or greater homology to any one of SEQ ID NOs: 80-85 or and/or a C-terminal sequence having 90% or greater homology to any one of SEQ ID NOs: 86-92. In another aspect, the engineered polypeptide further comprises an N-terminal sequence having 95% or greater homology to any one of SEQ ID NOs: 80-85 or and/or a C-terminal sequence having 95% or greater homology to any one of SEQ ID NOs: 86-92. In yet another aspect, engineered polypeptide further comprises an N-terminal sequence of SEQ ID NOs: 80-85 or and/or a C-terminal sequence of SEQ ID NOs: 86-92.

The C-terminal sequence, for example, can play a role in aggregation of the polypeptides, which can affect their physical properties. The N-terminal sequence is believed to play a role in the in the proper transport of the proteins from secretory cells to silk gland lumen, aid in fiber formation, and contribute to the structural properties of silk fibers.

The engineered polypeptides optionally additionally comprise units of SEQ ID NO: 1, SEQ ID NO: 2, SEQ ID NO: 3, SEQ ID NO: 6, or SEQ ID NO: 7, or units with 95% or greater homology to SEQ ID NO: 1, SEQ ID NO: 2, SEQ ID NO: 3, SEQ ID NO: 6, SEQ ID NO: 7.

Exemplary polypeptides include 100 to 8,000 amino acid residues.

A "consensus sequence" or a "unit" is a repetitive short sequence found in a spider silk protein. Thus, the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. Engineered spider silks, however, can be made wherein the primary structure of the protein comprises a number of exact repetitions of a single unit repeat. Additional synthetic spider silks can be synthesized which comprise a number of repetitions of one unit repeat together with a number of repetitions of a second unit repeat. Such a structure would be similar to a typical block copolymer fiber. Unit repeats of several different sequences can also be combined to provide a synthetic spider silk protein having properties suited to a particular application. The term "direct repeat" as used herein is a repeat in tandem (head-to-tail arrangement) with a similar repeat.

Peptide fragments of MaSp2, MaSp1a, MaSp1b, MaSp4a, MaSp4b, MaSp1c, and MaSp5 sequences and consensus sequences and polypeptides of the disclosure, and polynucleotides encoding such fragments include amino acid or nucleotide sequence lengths that are at least 25% (typically greater than 50%, 60%, or 70%, and commonly greater than 80%) of the length of an MaSp2, MaSp1a, MaSp, MaSp4a, MaSp4b, MaSp1c, and MaSp5p polypeptide or polynucleotide. Typically such sequences will have greater than 60% sequence identity (more typically greater than 70%, 75%, 80%, 85%, 90%, 95%, 97.5%, 99%, or 99.5%) with an MaSp2, MaSp1a, MaSp, MaSp4a, MaSp4b, MaSp1c, and MaSp5 polypeptide or polynucleotide when aligned so as to maximize overlap and identity while minimizing sequence gaps. Also included in the disclosure are polypeptides, peptide fragments, and polynucleotides encoding them, that contain or encode a segment comprising at least 8 to 10, typically at least 20, at least 30, or most commonly at least 40 contiguous amino acids. Such polypeptides and fragments may also contain a segment that shares greater than 70%, 75%, 80%, 85%, 90%, 95%, 97.5%, 99%, or 99.5% identity with any such segment of any of the MaSp family polypeptides or MiSp family of polypeptides, when aligned so as to maximize overlap and identity while minimizing sequence gaps. Visual inspection, mathematical calculation, or computer algorithms can determine the percent identity.

In another aspect of the disclosure, an engineered polypeptide may comprise various combinations of the consensus sequences described herein. Accordingly, polypeptides of the disclosure and polynucleotides include those comprising or encoding two or more copies, three or more copies, or four or more copies of the consensus sequences of Table 1. Also included are recombinant polypeptides and the polynucleotides encoding the polypeptides wherein the recombinant polypeptides are "chimeric polypeptides" or "fusion polypeptides" and comprise the sequence of any one of SEQ ID NOs. 1-31 operatively linked to a second polypeptide. The second polypeptide can be any polypeptide of interest having an activity or function independent of, or related to, the function of a spider silk protein as described herein. The term "operatively linked" is intended to indicate that the MaSp2, MaSp1a, MaSp1b, MaSp4a, MaSp4b, MaSp1c or MaSp5 sequence and the second polypeptide sequence are fused in-frame to each other. The second polypeptide can be fused to the N-terminus or C-terminus of an MaSp2, MaSp1a, MaSp1b, MaSp4a, MaSp4b, MaSp1c or MaSp5 sequence. For example, in one embodiment, the fusion polypeptide is a GST-MaSp4a or MaSp4b fusion polypeptide in which the MaSp4a or MaSp4b sequences are fused to the C-terminus of the GST sequences. Such fusion polypeptides can facilitate the purification of recombinant MaSp4a or MaSp4b polypeptides. In another embodiment, the fusion polypeptide comprises an MaSp4a or MaSp4b sequence comprising a heterologous signal sequence at its N-terminus. In certain host cells (e.g., mammalian host cells), expression and/or secretion of an MaSp4a and MaSp4b polypeptide can be increased through use of a heterologous signal sequence. As another example, an MaSp4a and MaSp4b polypeptide or fragment thereof may be fused to a hexa-histidine tag to facilitate purification of bacterially expressed protein, or to a hemagglutinin tag to facilitate purification of protein expressed in eukaryotic cells. Further, fusion polypeptides can comprise, for example, poly-His or the antigenic identification peptides described in the art. One such peptide is the FLAG® peptide, which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG peptide in the presence of certain divalent metal cations is described in the art. Monoclonal antibodies that bind the FLAG peptide are commercially available.

In an aspect, the engineered polypeptide has a tensile strength of greater than 3.4 G/denier, an elasticity as great as 35% and a stiffness as low as 0.6 Mpsi. In another aspect, the engineered polypeptide has a Young's modulus of about 3-10 GPa, an Ultimate Strength of about 200-800 MPa, an Extensibility of about 0.5-0.8 mm/mm, a Toughness of about 75-150 Mpa, or a combination thereof.

Encompassed by the disclosure are oligomers or fusion polypeptides that contain an MaSp2, MaSp1a, MaSp1b, MaSp4a, MaSp4b, MaSp1c or MaSp5 polypeptide or repeat fragment thereof. Oligomers that can be used as fusion partners can be in the form of covalently linked or non-covalently-linked multimers, including dimers, trimers, or higher oligomers. In an alternative embodiment the disclosure is directed to oligomers comprising multiple polypeptides joined via covalent or non-covalent interactions between peptide moieties fused to the polypeptides. Such peptides can be peptide linkers (spacers), or peptides that have the property of promoting oligomerization. Leucine zippers and certain polypeptides derived from antibodies are among the peptides that can promote oligomerization of the polypeptides attached thereto may be employed.

The units in the engineered polypeptides can be joined by linkers. In an aspect, a linker is a peptide linker moiety. The length of the linker moiety is chosen to optimize the biological activity of the polypeptide having an MaSp2, MaSp1a, MaSp1b, MaSp4a, MaSp4b, MaSp1c or MaSp5 sequence and can be determined empirically without undue experimentation. The linker moiety should be long enough and flexible enough to allow an MaSp2, MaSp1a, MaSp1b, MaSp4a, MaSp4b, MaSp1c or MaSp5 moiety to freely interact with a substrate or ligand. The linker moiety is typically a peptide between about one and 30 amino acid residues in length. A DNA sequence encoding a desired peptide linker can be inserted between, and in the same reading frame as, DNA sequences of the disclosure, using any suitable conventional technique. For example, a chemically synthesized oligonucleotide encoding the linker can be ligated between the sequences. In particular embodiments, a fusion polypeptide comprises from two to four or more MaSp2, MaSp1a, MaSp1b, MaSp4a, MaSp4b, MaSp1c or MaSp5 or chimeric polypeptides, separated by peptide linkers.

The engineered polypeptides of the disclosure can also include a localization sequence to direct the polypeptide to particular cellular sites by fusion to appropriate organellar targeting signals or localized host proteins. A polynucleotide encoding a localization sequence, or signal sequence, can be ligated or fused at the 5' terminus of a polynucleotide encoding an engineered polypeptide such that the signal peptide is located at the amino terminal end of the resulting fusion polynucleotide/polypeptide. In eukaryotes, the signal peptide functions to transport a polypeptide across the endoplasmic reticulum. The secretory protein is then transported through the Golgi apparatus, into secretory vesicles and into the extracellular space or the external environment. Signal peptides include pre-pro peptides that contain a proteolytic enzyme recognition site.

Exemplary localization sequences include a nuclear-, an endoplasmic reticulum-, a peroxisome-, or a mitochondrial-localization sequence, or a localized protein. Exemplary localization sequences include those targeting the nucleus, mitochondria, endoplasmic reticulum, peroxisome (SKF), plasma membrane, CC, CXC and the like, cytoplasmic side of plasma membrane (fusion to SNAP-25), or the Golgi apparatus (fusion to furin).

An engineered polypeptide of the disclosure can be produced by standard recombinant molecular biology techniques. In one aspect, polynucleotide fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another aspect, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence. Moreover, many expression vectors are commercially available that already encode a fusion moiety (e.g., a GST polypeptide).

Polynucleotides are described in the tables above and the sequence listing.

The disclosure further includes engineered polypeptides with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the disclosure in bacterial expression systems, such as *E. coli*, provides non-glycosylated molecules. Further, a given preparation can include multiple differentially glycosylated species of the polypeptide. Glycosyl groups can be removed through conventional methods, in particular those utilizing glycopeptidase.

Additional variants within the scope of the disclosure include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide.

In another aspect, the engineered polypeptides can comprise a therapeutic agent. The engineered polypeptide can be mixed with a therapeutic agent prior to forming a biomaterial, for example, or loaded into a biomaterial after it is formed. Alternatively, the therapeutic agent can be covalently or noncovalently linked to the engineered polypeptide. The variety of different therapeutic agents that can be used in conjunction with the engineered polypeptides and materials is vast and includes small molecules, proteins, peptides and nucleic acids. In general, therapeutic agents include antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); anti-angiogenic proteins such as endostatin, and other naturally derived or genetically engineered proteins, polysaccharides, glycoproteins, and lipoproteins. Additionally, the engineered polypeptides and materials can be used to deliver any type of molecular compound, such as, pharmacological materials, vitamins, sedatives, steroids, hypnotics, antibiotics, chemotherapeutic agents, prostaglandins, and radiopharmaceuticals. The delivery system can also be used to deliver proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

A polypeptide of the disclosure may be prepared by culturing transformed or recombinant host cells under culture conditions suitable to express a polypeptide of the disclosure. The resulting expressed polypeptide may then be purified from such culture using known purification processes. The purification of the polypeptide may also include an affinity column containing agents which will bind to the polypeptide; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide of the disclosure may also be expressed in a form that will facilitate purification. For example, it may be expressed as a fusion polypeptide, such as those of maltose binding polypeptide (MBP), glutathione-5-transferase (GST) or thioredoxin (TRSX). Kits for expression and purification of such fusion polypeptides are commercially available from New England BioLab (Beverly, Mass.), Pharmacia (Piscataway, N.J.), and Invitrogen, respectively. The polypeptide can also be tagged with an epitope and subsequently purified by using a specific antibody directed to such epitope. Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous recombinant polypeptide. The polypeptide thus purified is substantially free of other insect, plant, bacterial or mammalian polypeptides and is defined in accordance with the disclosure as a "substantially purified polypeptide. A polypeptide of the disclosure may also be expressed as a product of transgenic animals or insects, which are characterized by somatic or germ cells containing a polynucleotide encoding a polypeptide of the disclosure.

It is also possible to utilize an affinity column such as a monoclonal antibody generated against polypeptides of the disclosure, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure. In this aspect of the disclosure, proteins that bind a polypeptide of the disclosure can be bound to a solid phase support or a similar substrate suitable for identifying, separating, or purifying cells that express polypeptides of the disclosure on their surface. Adherence of, for example, an antibody to a solid phase surface can be accomplished by any means, for example, magnetic microspheres can be coated with these polypeptide-binding proteins and held in the incubation vessel through a magnetic field.

A polypeptide of the disclosure may also be produced by known conventional chemical synthesis. Methods for constructing the polypeptides of the disclosure by synthetic means are known to those skilled in the art. The synthetically-constructed polypeptide sequences, by virtue of sharing primary, secondary or tertiary structural and/or conformational characteristics with a native polypeptides may possess biological properties in common therewith, including biological activity.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Typically, the polypeptide of the disclosure is purified to substantial homogeneity, as indicated by a single polypeptide band upon analysis by SDS-PAGE.

The polypeptide band can be visualized by silver staining, Coomassie blue staining, or (if the polypeptide is radiolabeled) by autoradiography.

Also included herein are synthetic materials comprising the engineered polypeptides and/or other polypeptides described herein such as the polypeptides of SEQ ID NOs. 9-32.

In an aspect, a synthetic material comprises an engineered polypeptide comprising at least two units, wherein each unit comprises SEQ ID NO: 4 or SEQ ID NO: 5, or a polypeptide with 90% or greater homology to SEQ ID NO: 4 or SEQ ID NO: 5, wherein the engineered polypeptide does not comprise SEQ ID NO: 12 or SEQ ID NO: 13.

In another aspect, a synthetic material comprises a polypeptide of any one of SEQ ID NOs: 9-32, a polypeptide with 90% or greater homology any one of SEQ ID NOs: 9-32, a polypeptide encoded by any one of SEQ ID NOs. 57-79 or a polypeptide with 90% or greater homology to a polypeptide encoded by any one of SEQ ID NOs. 57-79. In specific aspects, the synthetic material comprises SEQ ID NO. 12, SEQ ID NO: 13, a polypeptide with 90% or greater homology to SEQ ID NO. 12, a polypeptide with 90% or greater homology to SEQ ID NO: 13, or a combination thereof.

In yet another aspect, a synthetic material comprises a polypeptide comprising SEQ ID NO: 4 or SEQ ID NO: 5, or a sequence with 90% or greater homology to SEQ ID NO: 4 or SEQ ID NO: 5, wherein the synthetic material is not found in nature.

In a specific aspect, polypeptide further comprises an N-terminal sequence having 90% or greater homology to any one of SEQ ID NOs: 80-85 and/or a C-terminal sequence having 90% or greater homology to any one of SEQ ID NOs: 86-92. In another aspect, the polypeptide further comprises an N-terminal sequence having 95% or greater homology to any one of SEQ ID NOs: 80-85 or and/or a C-terminal sequence having 95% or greater homology to any one of SEQ ID NOs: 86-92. In yet another aspect, the polypeptide further comprises an N-terminal sequence of SEQ ID NOs: 80-85 or and/or a C-terminal sequence of SEQ ID NOs: 86-92.

In yet another aspect, the polypeptide further comprises one or more units of SEQ ID NO: 1, SEQ ID NO: 2, SEQ ID NO: 3, SEQ ID NO: 6, or SEQ ID NO: 7, or one or more units with 90% or greater homology to SEQ ID NO: 1, SEQ ID NO: 2, SEQ ID NO: 3, SEQ ID NO: 6, SEQ ID NO: 7.

Synthetic materials find uses in the textile industry (e.g., as filaments, yarns, ropes, and woven material). Such materials made using the methods and compositions described herein will take advantage of the extreme toughness, tensile strength, and extensibility of silk. In addition, the polypeptides of the disclosure can be used in pliant energy absorbing devices including armor and bumpers. Besides the mechanical properties of spider silk, silk is proteinaceous (thus not petroleum-based like nylon or para-aramid synthetic fibers, e.g., Kevlar®). Accordingly, the polypeptides of the disclosure provide biocompatible and biodegradable material useful in various industries including textiles and medicine. For example, the supercontraction ability of dragline silk can be beneficial for sutures that can tighten, compression bandages, or space minimizing packaging. Additionally the polypeptides can be used in the generation of scaffolds and material in tissue engineering, implants and other cell scaffold-based materials.

In an aspect, the biomaterials can be shaped into articles for tissue engineering and tissue guided regeneration applications, including reconstructive surgery. The structure of the scaffold allows generous cellular ingrowth, eliminating the need for cellular preseeding. The scaffolds may also be molded to form external scaffolding for the support of in vitro culturing of cells for the creation of external support organs. For example, the scaffold can function to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support.

The tissue engineering scaffold may comprise cells. A number of different cell types or combinations thereof may be employed, depending upon the intended function of the tissue engineered construct being produced. These cell types include, but are not limited to: smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. For example, smooth muscle cells and endothelial cells may be employed for muscular, tubular constructs, e.g., constructs intended as vascular, esophageal, intestinal, rectal, or ureteral constructs; chondrocytes may be employed in cartilaginous constructs; cardiac muscle cells may be employed in heart constructs; hepatocytes and bile duct cells may be employed in liver constructs; epithelial, endothelial, fibroblast, and nerve cells may be employed in constructs intended to function as replacements or enhancements for any of the wide variety of tissue types that contain these cells. In general, any cells may be employed that are found in the natural tissue to which the construct is intended to correspond. In addition, progenitor cells, such as myoblasts or stem cells, may be employed to produce their corresponding differentiated cell types. In some instances it may be preferred to use neonatal cells or tumor cells.

Cells can be obtained from donors (allogenic) or from recipients (autologous). Cells can also be of established cell culture lines, or even cells that have undergone genetic engineering. Pieces of tissue can also be used, which may provide a number of different cell types in the same structure.

Appropriate growth conditions for mammalian cells are well known in the art. Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and tissue desired.

The invention is further illustrated by the following non-limiting examples.

EXAMPLES

Methods

PacBio® SMRT and Illumina® Sequencing of Major Ampullate Silk Gland Expression Libraries: Major ampullate (MA) glands were dissected from *C. darwini* females reared by MK and MG from egg sacs collected in Andasibe-Mantadia National Park (between 18.94760oS, 48.41972oE at 960 m elev.), Toamasina Province, eastern Madagascar in 2012. Major ampullate glands from seven *C. darwini* females were imaged, along with MA glands from four female *Argiope aurantia* and three female *Nephila clavipes*, measuring duct and ampullate length with ImageJ. RNA was extracted from major ampullate glands (one individual per extraction) by homogenization in TriZol® and cleanup using Qiagen's RNeasy® kit, and removal of DNA. Using one *C. darwini* MA gland RNA extraction (cd46) cDNA was synthesized at the UMass Medical School's Deep Sequencing Core (UMMS-DSC) using the Iso-Seq™ protocol (Pacific Bioscience, Inc; Menlo Park, CA). cDNA was fractionated into two size distributions. The larger fraction >1.2 kb was used to construct a SMRTBell™ library, which was sequenced on three SMRTCells™ on a PacBio® RS II instrument with 120-minute movies. RNA from the MA silk glands of two individuals (cd46 and cd47) was submitted to the UMMS-DSC, where cDNA was synthesized separately for each individual using the creator SMARTer™ method (Takara Bio USA), and fragmented to 650 bp prior to Illumina RNA-Seq library construction. The two MA gland RNA-Seq libraries were sequenced on three separate MiSeq instrument runs, sequencing 300 bp paired end reads. Illumina® adapters and SMART oligos (Table 5) used in cDNA synthesis were trimmed from reads using CUTADAPT 1.14.

TABLE 5

Sequencing primers

| Primer Name | SEQ ID NO: | Forward | SEQ ID NO: | Reverse |
|---|---|---|---|---|
| Illumina® TruSeq P5 | 33 | AATGATACGGCGAC CACCG | 34 | CGGTGGTCGCCGTATCAT T |
| Illumina® TruSeq P7 | 35 | AGGATACGGCAGAA GACGAAC | 36 | GTTCGTCTTCTGCCGTATG CT |
| TS index primer | 37 | AGATCGGAAGAGCA CACGTCTGAACTCCA GTCAC | 38 | GTGACTGGAGTTCAGACG TGTGCTCTTCCGATCT |
| TS R2 Seq Primer | 39 | CTAGCCTTCTCGTGT GCAGACTTGAGGTCA GTG | 40 | CACTGACCTCAAGTCTGC ACACGAGAAGGCTAG |
| Illumina® Universal R1 | 41 | ACACTCTTTCCCTAC ACGACGCTCTTCCGA TCT | 42 | AGATCGGAAGAGCGTCGT GTAGGGAAAGAGTGT |
| Illumina® PCR index2 fastqc | 43 | CGATGTATCTCGTAT GCCGTCTTCTGCTTG | 44 | CAAGCAGAAGACGGCAT ACGAGATACATCG |
| Illumina SE PCR fastqc | 45 | AGATCTCGGTGGTCG CCGTATCATT | 46 | AATGATACGGCGACCACC GAGATCT |
| Clontech common | 47 | AAGCAGTGGTATCA ACGCAGAGTAC | 48 | GTACTCTGCGTTGATACC ACTGCTT |
| Clontech SMARTE RIIA | 49 | AAGCAGTGGTATCA ACGCAGAGTACNNN NN | 50 | NNNNNGTACTCTGCGTTG ATACCACTGCTT |
| Clontech polyT | 51 | AAGCAGTGGTATCA ACGCAGAGTACTTTT TTTTTTTTTTTTTTT TTTTT | 52 | AAAAAAAAAAAAAAAA AAAAAAAGTACTCTGCG TTGATACCACTGCTT |

Assembly of transcriptomes: Data from the SMRT sequencing cells were processed with Pacific Biosciences' RS_IsoSeq Classify script to identify non-chimeric full-length transcripts (i.e., sequences containing 5' 3' primers and poly A tails), which were used as input to the Cluster script to collapse highly similar sequences into non-redundant consensus isoforms using the ICE algorithm, followed by use of the QUIVER algorithm to "polish" isoforms with highly similar but non-full length transcripts corresponding to each full-length isoform. Given this pipeline separates partial cDNAs of the same transcript only differing in length (because they are interpreted as full-length), we further clustered tBLASTn hits to spidroin terminal domain queries using CD-HIT at 95% nucleotide identity across their full-length, selecting the longest sequence per cluster for analyses. A separate de novo transcriptome from all Illumina® data was generated from 14.3 million reads using Trinity 2.0.6. BUSCO was used to evaluate the transcriptome by assessing the presence and length of conserved single copy orthologs from arthropod species. Assembled sequences were subject to BLASTx searches against NCBI's nr database, retaining hits with e-scores ≤e-0.5. Translations were produced based on the frame of significant BLAST hits, or the longest open reading frame in the absence of a BLAST hit.

Spidroin Characterization: Spidroin sequences in transcriptome assemblies were identified using tBLASTn with known spidroin N- and C-terminal domain protein sequences as queries. getORF was used to translate spidroin transcripts, and the longest translation in the frame of the BLAST hit was identified. CDhit was used to cluster translated spidroins into groups with full-length, identical terminal domains; manual inspection of all spidroin BLAST hits identified additional sequences containing complete termini, all of which were clustered into groups sharing 95% amino acid identity across the terminal domain. For each spidroin sequence cluster we characterized the repetitive structure of the longest sequence based on previously defined spidroin motifs. Larger iterated ("ensemble") repeats composed of combinations of these motifs were defined by aligning highly similar consecutive sequence within proteins using MUSCLE v. 3.2.6, and computing a consensus reporting the modal residue for each position.

Sequences were designated MaSp proteins if terminal domains were most closely related to previously defined MaSp termini. The MaSp1 or MaSp2 designation was based on the presence of amino acid motif combinations in the repetitive region previously defined as characteristic for those proteins. As the recently described MaSp3 was not identified among C. darwini transcripts, nomenclature for MaSp sequences newly described here were named MaSp4a, MaSp4b, and MaSp5, where MaSp4a and MaSp4b may represent alleles of the same protein or closely related paralogs. Protein secondary structure (e.g., percent helices, sheets, and/or turns) was bioinformatically predicted with the garnier EMBOSS plugin in Geneious.

Expression Analyses: Trimmed Illumina® reads from the two MA gland RNA-Seq libraries were used to estimate abundance of Trinity assembled transcripts using Salmon in quasi-mapping mode (data not shown). Determining spidroin expression is challenging because of fragmented transcripts and incorrect mapping of repetitive regions, especially given spidroin transcripts typically contain differing lengths of repetitive sequence. Thus, we reduced sequences in the Illumina® assembly containing identical C-termini to a single representative, trimmed to 500 bp surrounding the non-repetitive termini. TPM was re-estimated for transcripts in this revised assembly using Salmon and aggregating TPM for spidroin C-termini if they shared ≥95% identity at the amino acid level (data not shown).

Spidroin Phylogenetics Analyses: Spidroin terminal domain sequences (data not shown) were used in phylogenetic analyses along with C. darwini sequences sampling C-termini representing gland-associated spidroins (TuSp1, MiSp, Flag, AcSp1, PySp1, AgSp) having linked N-terminal domains from different araneoid species, and including a greater sampling of MaSp C-termini from the Caerostris family Araneidae. N-terminal analyses included sequences linked to C-termini used in the aforementioned C-terminal phylogenetic analysis. Sequences were aligned with MUSCLE 3.8.31. Bayesian phylogenetic trees were generated from amino acid alignments using Mr. Bayes v. 3.2.6, implementing a mixed model for $5 \times 10^6$ generations plus gamma distribution. Consensus Bayesian trees were computed from post burn-in trees (discarding the first 25%), and rooted using a mygalomorph spidroin (B.c. fibroin 1).

Silk Fiber and Gland Protein Analyses: Dragline fibers were collected from forcibly silked C. darwini females. Three samples of spun dragline from three individuals and one pair of C. darwini MA glands from a single individual were sent to the UC Davis Molecular Structure Facility, and hydrolyzed with 6N HCl for 24 hrs at 110° C. This was followed by ion-exchange chromatography using an L-8800 Hitachi analyzer coupled to a post-column ninhydrin reaction system to separate and detect amino acids. One dragline sample was also run on a L-8900 Hitachi analyzer using a lithium citrate buffer to detect hydroxyproline. Results were used to compute percent molarity of amino acids in samples. Amino acid compositions of spidroin sequences were determined with ProtParam.

Data availability: Sequence data from this study is available at NCBI's SRA database under the accession submissions SRR7499252, SRR7499250, SRR7499251. Assembled transcriptomes are available at NCBI's TSA database under accession numbers GGUO00000000 and GGTX00000000.

Results

To obtain C. darwini's major ampullate spidroins, we used Single Molecule Real Time sequencing of MA gland expressed gene transcripts (cDNAs) to produce 10,667 consensus sequences. A C. darwini MA gland transcriptome was also constructed from two Illumina® RNA-Seq libraries producing 207,117 unique sequences. In both assemblies, we surveyed spidroin diversity by clustering translated sequences containing C-terminal domains with ≥95% identity. This yielded 14 sequence groups, seven with best BLAST hits to MaSp sequences. The remainder had top BLAST hits to spidroins associated with other silks: PySp (piriform/cementing silk spidroin), MiSp (minor ampullate silk spidroin), TuSp (tubuliform/egg-case silk spidroin), Flag (flagelliform/capture spiral silk spidroin), AcSp (aciniform/wrapping silk spidroin) and AgSp (aggregate/glue spidroin).

We examined the longest spidroin in each C-terminal cluster and found three were most similar to MaSp1, having GGX and $A_n$ motifs in repetitive sequence, whereas one was most similar to MaSp2 with combined $GPGX_1$ ($X_1$ is G, S, A or Q; SEQ ID NO: 53), GGX and $A_n$ motifs (FIG. 1, SEQ ID NOs. 1-7). However, three newly described spidroins had C-termini with top BLAST hits to MaSp1 or MaSp2 but lacked poly-alanine ($A_n$). One of these, MaSp5, is mostly composed of GGX motifs. By contrast, MaSp4a and MaSp4b are strikingly unique spidroins enriched with novel GPGPQ motifs, occupying 44-52% of the repetitive region (SEQ ID NO: 8). MaSp4 is markedly different from the eight MaSps from the orb-weaver Nephila clavipes' genome, with GPGPQ (SEQ ID NO: 54) only appearing once in Nephila MaSp-g and iterations of this motif are not seen in other species' spidroins. Our longest MaSp4a includes eight 63 amino acid repeats, each containing 4-6 GPGPQ motifs, one GPGG (SEQ ID NO: 55) motif, and one VSVVS[A/T]TVS (SEQ ID NO: 56) motif (SEQ ID NO:8).

Figure 2:
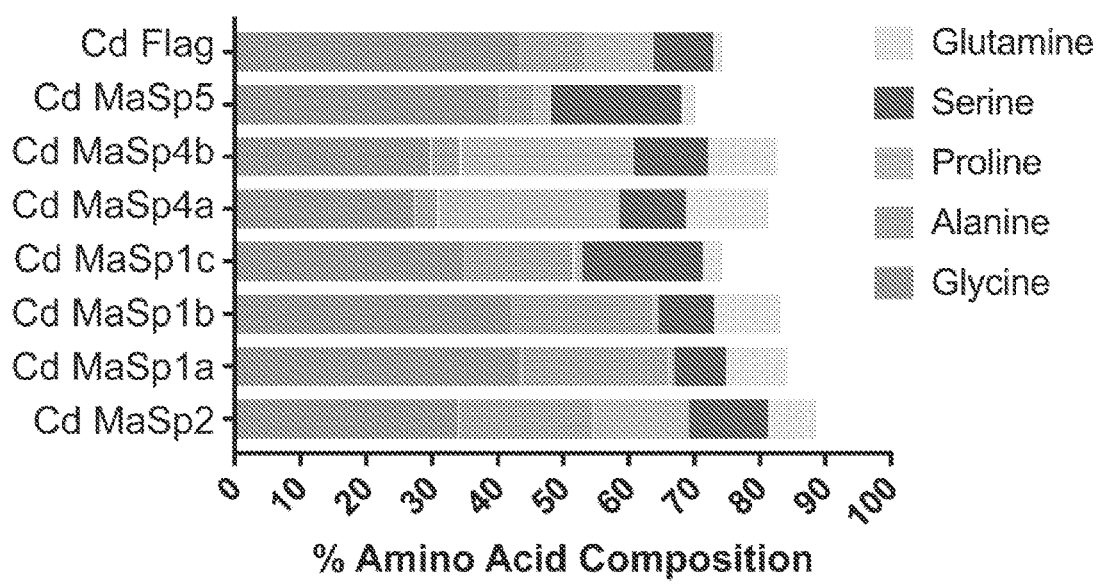
FIG. 2 shows the amino acid composition of *C. darwini* MaSp and Flag proteins.

Orb-weaver dragline is predominately composed of glycine (34.7-42.2%), alanine (17.6-27.5%), and proline (1.7-15.7%), as its primary constituents are MaSp1 and MaSp2. Both proteins are dominated by glycine and alanine, but proline is almost exclusively in MaSp2 (8.6-15.1% vs. 0.4-1.0% in MaSp1). Amino acid compositions of *C. darwini* MaSp1a-c and MaSp2 are similar to those in other species. By comparison, *C. darwini* MaSp4 contains 26.3-27.5% proline and is deficient in alanine (3.6-4.5%; FIG. 2). Higher proline is linked with greater silk extensibility, and MaSp4's proline substantially exceeds the 10.4-16.3% proline in Flag from elastic capture silk (FIG. 2).

Figure 3:
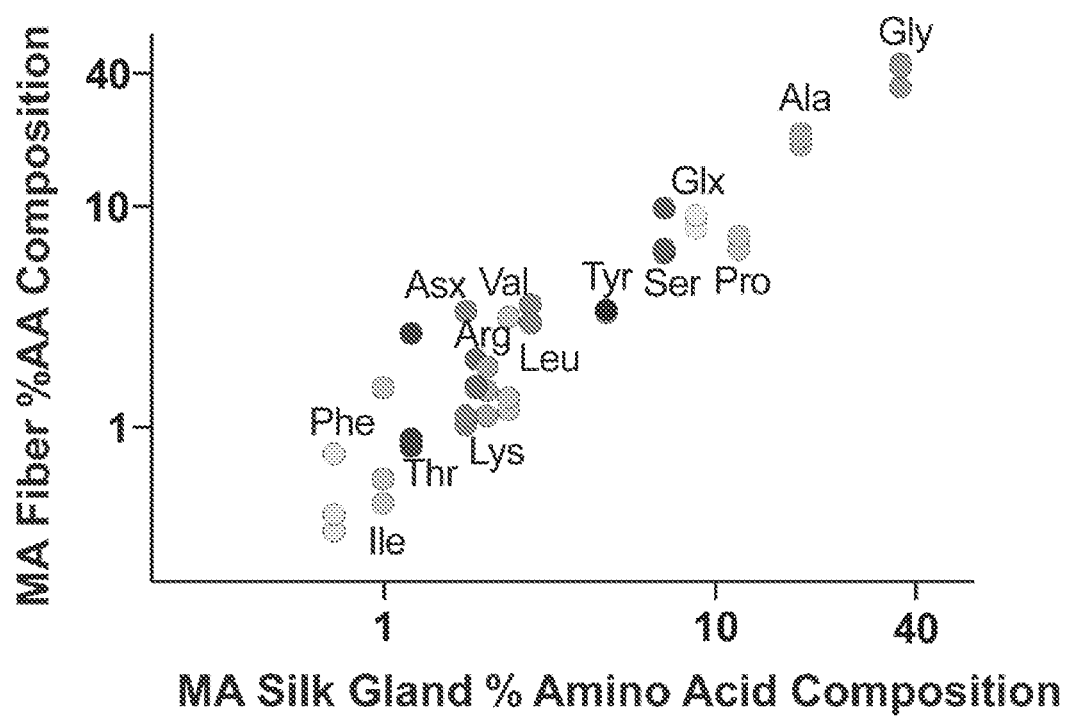
FIG. 3 shows the percent amino acid composition of dragline (major ampullate) fibers (n=3; mean±s.e.m.) against major ampullate gland composition (n=1), five most abundant residues color-coded as in part a (Glx=glutamine+glutamate).

The high proline of MaSp2 and Flag is associated with $GPGX_1$ (SEQ ID NO: 53) motifs, which form beta-turns conferring extensibility to dragline and flagelliform silk. We used the Garnier algorithm to predict secondary structures in *C. darwini* spidroins and found the highest percentage of turns assigned to MaSp4a (32.2%) and MaSp4b (31.6%), exceeding MaSp2 (17.2-26.9%) and Flag (19.3-24.7%). Overall proline levels in *C. darwini* dragline (6.4-7.3%; n=3) and MA glands (11.7%; n=1) fall within the range of other species (FIG. 3) so that proline abundance per se is unlikely to explain the silk's greater extensibility. Instead, we propose that proline's arrangement in GPGPQ motifs may amplify its influence on silk mechanics by forming novel structural domains embedded among other MaSp proteins.

Figure 4:
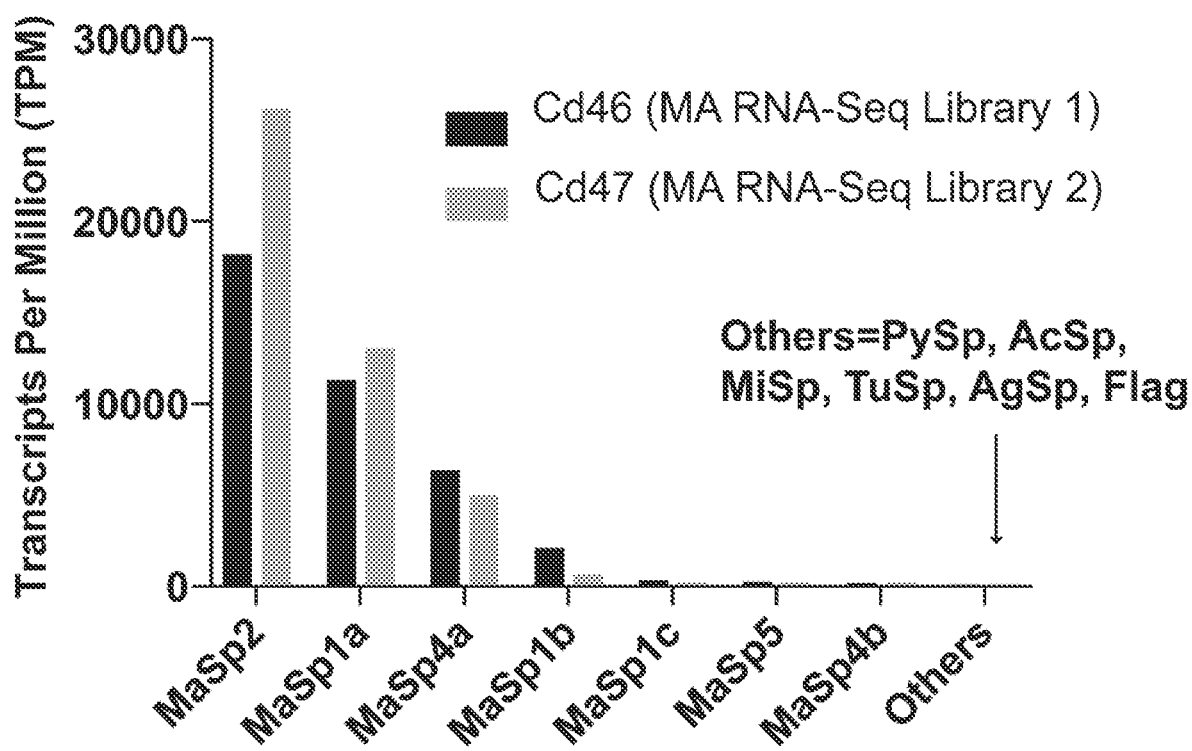
FIG. 4 shows that expression of spidroin transcripts in *C. darwini* Major Ampullate Silk Glands from two gland-specific RNA-Seq libraries. Expression measured in Transcripts Per Million (TPM) in replicate individuals (cd46 and cd47).
Figure 5:
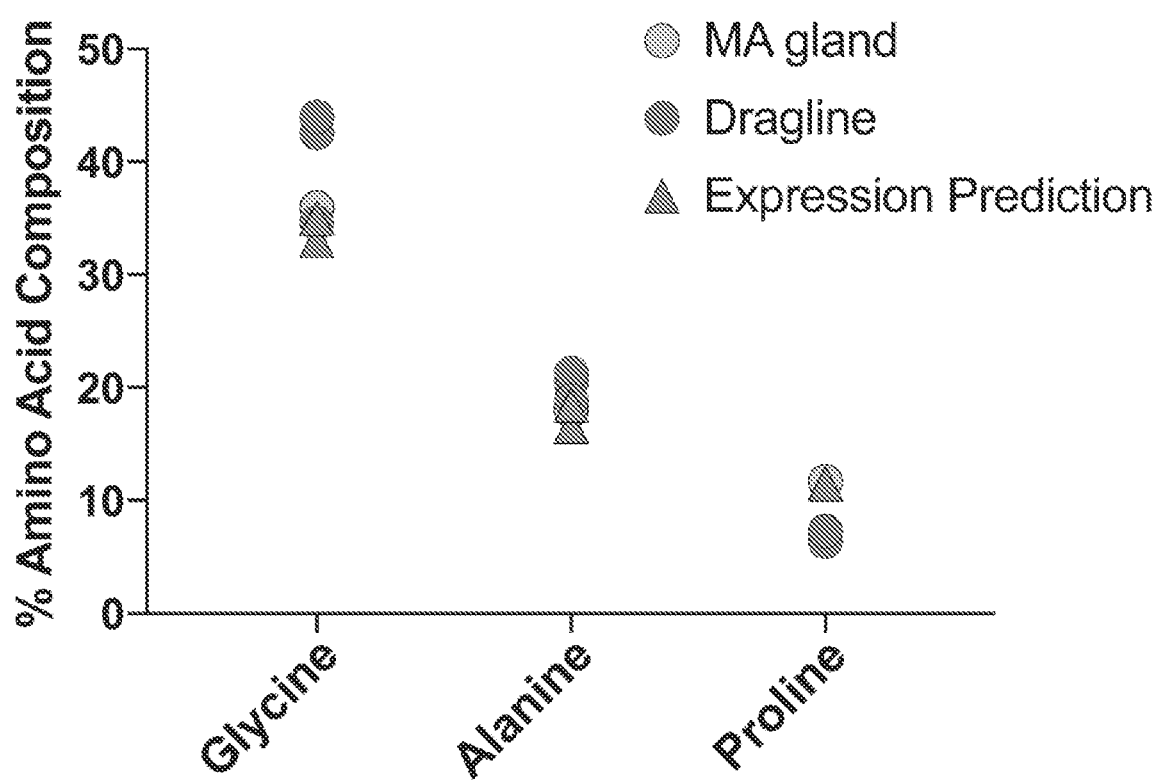
FIG. 5 shows that predicted glycine, alanine and proline composition from expression data closely matched MA gland and dragline composition (error bars represent s.e.m.).

To determine which spidroins are most highly expressed in *C. darwini* MA glands and likely to have the greatest impact on dragline mechanics, we estimated Illumina®-derived transcript abundance across two individual's MA glands in TPM (Transcripts Per Million). Among all spidroins and across replicates, MaSp2 had the highest expression (average TPM=22340.9), representing 46-56% of spidroin expression, followed by MaSp1a (TPM=12326.3). MaSp4a was third most abundant (TPM=5837.4), representing 11-16% of spidroin expression in *C. darwini* MA glands (FIG. 4). By contrast, non-MaSp spidroins (TuSp, Flag, AcSp, PySp, MiSp, AgSp) had a combined TPM of 39.8-91.7, <0.2% of MA expression. The relative ratio of MaSp2, MaSp1a and MaSp4a predict dragline containing 33.0-35.0% glycine, 16.6-18.4% alanine and 11.4-11.5% proline. These values closely match composition values of *C. darwini* dragline (33.6-44.0% glycine, 18.9-21.3% alanine, 6.4-7.3% proline; n=3) and MA glands (36.0% glycine, 18.0% alanine, 11.7% proline; n=1; FIG. 5), consistent with spidroin transcript abundance positively correlating with dragline incorporation. Thus, high expression of MaSp4a in MA glands supports its functional role in *C. darwini* dragline mechanics.

Figure 6:
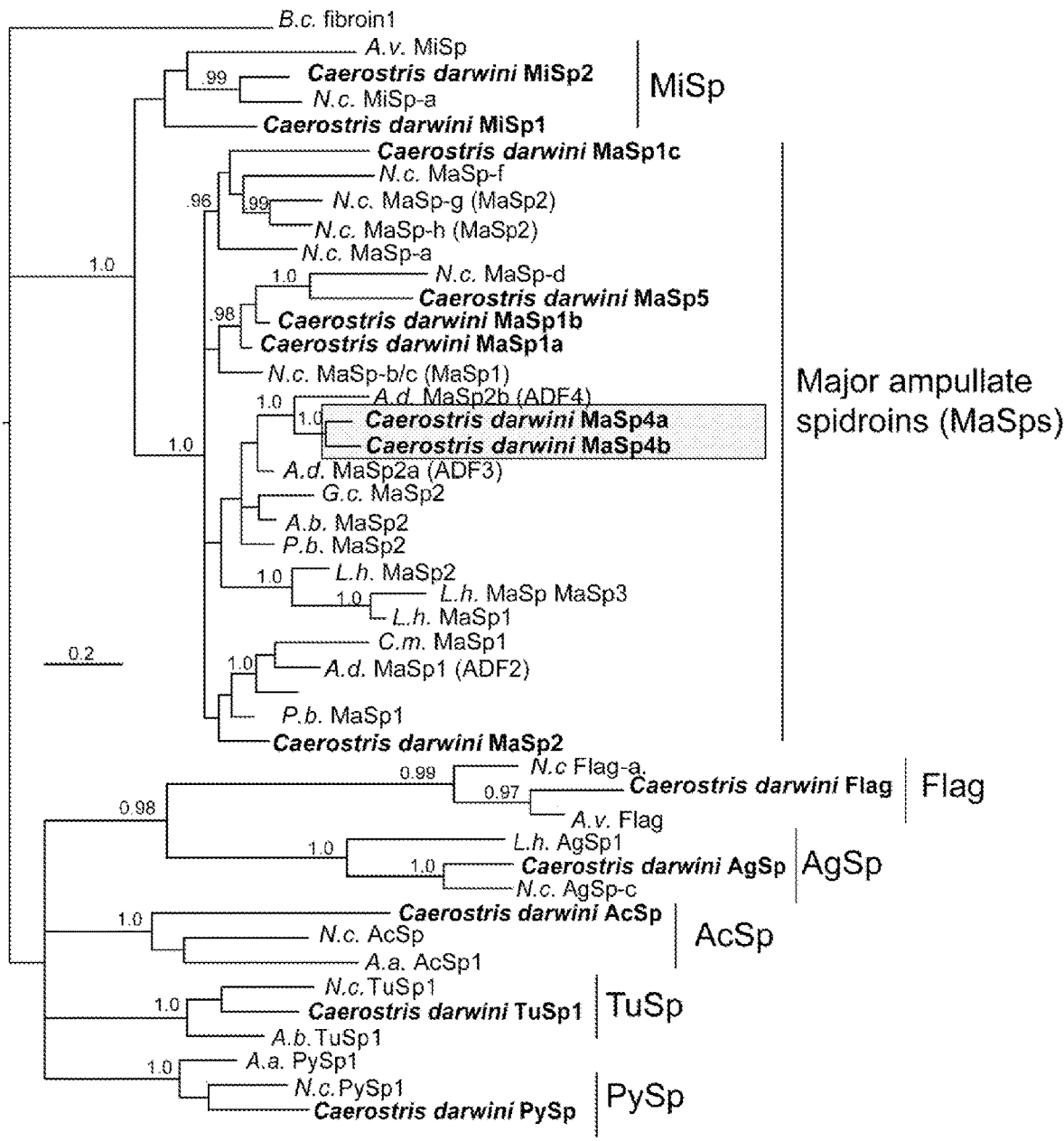
FIG. 6 shows spidroin (silk protein) Carboxy (C)-terminal phylogenetic tree nests GPGPQ-rich *Caerostris darwini* proteins in Major Ampullate Spidroin (MaSp) clade. The tree is Bayesian 50% majority rule consensus of post-burn-in trees. Sequences reported in this study from *C. darwini* in bold text. Support values at nodes are clade posterior probability values where ≥95. Other clades of functionally assigned silk proteins highlighted as follows: PySp=piriform (attachment) silk protein; TuSp=tubuliform (egg-case) silk protein; MiSp=minor ampullate (scaffolding/bridge line) silk protein; Flag=flagelliform (capture spiral) silk protein; AcSp=aciniform (prey-wrapping) silk protein; AgSp=aggregate (glue) protein. Species abbreviations as follows: N.c.=*Trichonephila clavipes*; B.c.=*Bothriocyrtum californicum*; A.v.=*Araneus ventricosus*; L.h.=*Latrodectus hesperus*; A.b=*Argiope bruennichi*; A.a.=*Argiope argentata*; A.d.=*Araneus diadematus*; G. c.=*Gasteracantha mammosa*; C. m.=*Cyrtophora moluccensis*; P.b.=*Parawixia bistriata*.
Figure 7:
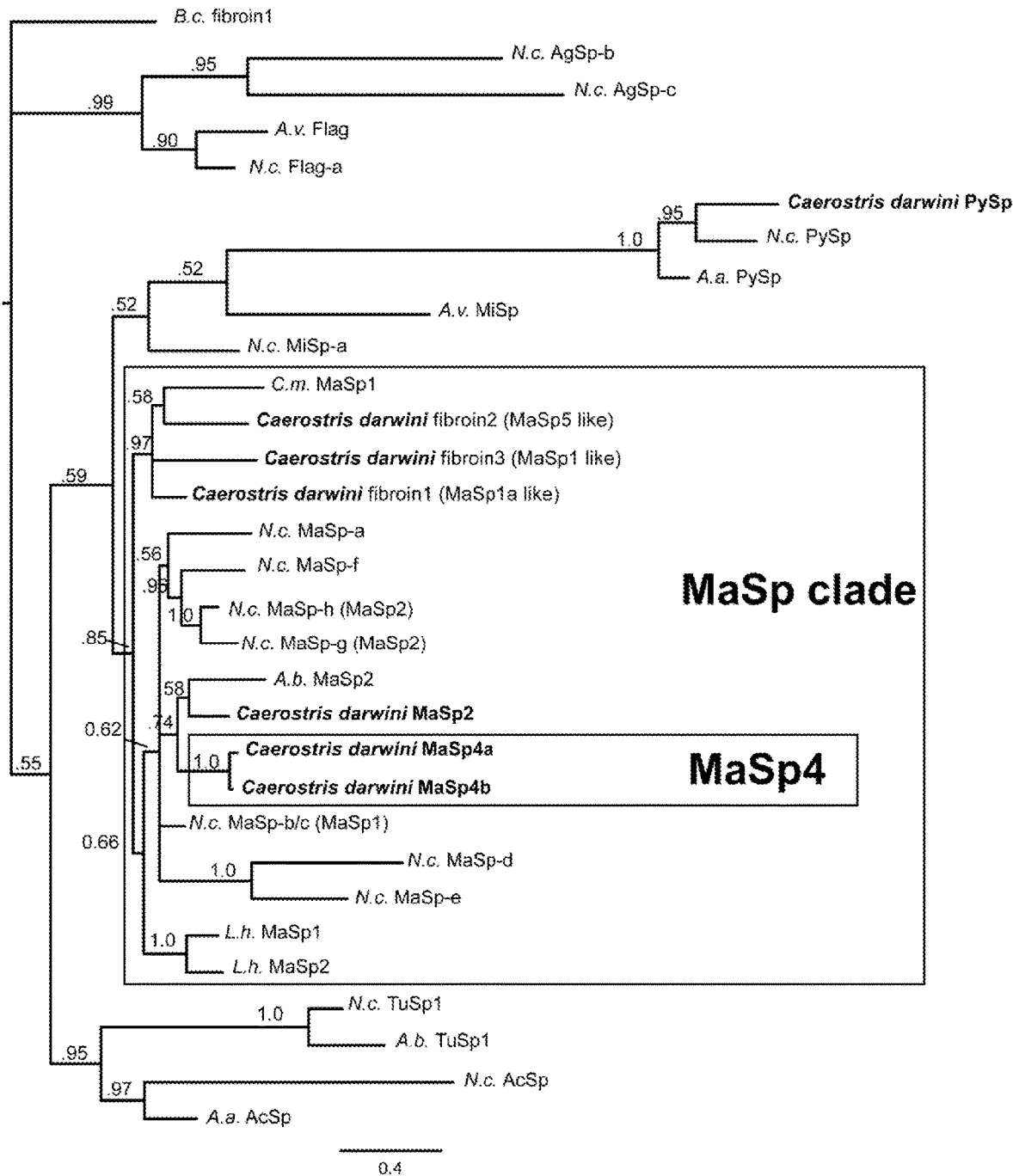
FIG. 7 shows spidroin (silk protein) Amino (N)-terminal phylogenetic tree. The tree is Bayesian 50% majority rule consensus of post-burn-in trees. Sequences reported in this study from *C. darwini* in bold text. Support values at nodes are clade posterior probability values.

To investigate *C. darwini* dragline evolution, we reconstructed spidroin phylogenetic relationships. MaSp4a and MaSpb are firmly nested in the dragline spidroin (MaSp) C-terminal clade and appear most closely related to MaSp2 from confamilial orb-weaver *Araneus diadematus*, with their C-termini sharing 68-69% nucleotide identity (FIG. 6). The assemblies also included seven spidroin N-termini from MaSp4a, MaSp4b, MaSp2, PySp, MaSp1 variants and MaSp5. Their relationships similarly showed MaSp4 within the MaSp N-terminal clade, but closest to *Argiope* and *C. darwini* MaSp2. MaSp1 and MaSp2 do not form reciprocally monophyletic clades, previously attributed to intergenic concerted evolution and selection to homogenize co-expressed termini (FIG. 7). Nevertheless, our results imply the derivation of MaSp4 from a MaSp2 gene, consistent with the GPG-rich nature of both. Consequently, while MaSp4 retains terminal domains highly similar to typical dragline proteins, its repetitive structural sequence has substantially increased in proline suggesting its adaptive evolution to support *C. darwini*'s giant webs.

Orb-weaver MA glands are subdivided into discrete sections: (1) the tail for protein secretion, (2) the ampullate sac storing liquid (data not shown). *C. darwini*'s MA spinning ducts are unusually long with the loop connecting limbs 2 and 3 extending to the ampullate sac midpoint or beyond (average duct length along ampullate sac=4.35 mm±0.78; n=7). In other species examined for this study or from the literature, this duct loop does not extend further than the distal portion of the ampullate sac (e.g., average duct length along sac=1.08 mm±0.18 in *Argiope aurantia*). The average length of the *C. darwini* MA duct (33.64 mm, ±2.50; n=7) exceeds the length in *Nephila clavipes* (25.5 mm±4.8) and *A. aruantia* (16.3 mm±1.02). Moreover, the average duct length to ampullate sac length ratio in *C. darwini* (4.26±0.54) is 1.5-1.8× greater than in *A. aurantia* and *N. clavipes*.

The MA duct transforms liquid silk proteins into a fiber through ion exchange, water removal, and decreasing pH along the duct. These changes and increasing shear forces, align spidroin monomers to form intermolecular secondary structures that determine silk mechanical performance (e.g., beta-sheets providing strength). Extensibility and strength normally tradeoff, but *C. darwini* dragline has increased extensibility without reduced strength, and x-ray diffraction shows it retains crystalline structure like typical orb-weaver dragline. The lengthened spinning duct of *C. darwini*'s MA gland may facilitate alignment of spidroins to maintain dragline tensile strength (potentially by increasing beta-sheet formation) as MaSp4's GPGPQ-containing motifs introduce increased extensibility. This could be tested by investigating biochemical and physical processes along *C. darwini*'s spinning duct.

Thus, in addition to high expression of MaSp2 and MaSp1, *C. darwini* major ampullate glands highly express MaSp4 transcripts, which encode a silk protein dominated by novel GPGPQ (SEQ ID NO: 54) motifs. If these motifs form beta-turns similar to $GPGX_1$ SEQ ID NO: 53) motifs as suggested by Garnier analysis this would introduce secondary structures resembling the nano-springs of flagelliform silk by which *C. darwini* dragline could achieve greater toughness through increased extensibility, That MaSp4's GPGPQ (SEQ ID NO: 54) motifs appear restricted to *C. darwini* suggests a recent origin of this protein within the genus from MaSp2 genes, consistent with selection for tough and extensible silk to support enormous orb-webs. *C. darwini*'s lengthened MA gland's spinning duct may also contribute to assembly of especially tough dragline. Hence, a suite of traits from genes to physiology likely coevolved with the unique ecology of *C. darwini*.

We anticipate these findings will be leveraged to produce silk-based materials mimicking the extraordinary toughness of *C. darwini* dragline. Such work could express *C. darwini* dragline spidroins in varying proportions, or engineer chimeric spidroins for biomaterials with enhanced functional properties. An important open question is how spinning duct length shapes material properties. Accordingly, this study reinforces the importance of evolutionary comparative studies for discovering biotechnology opportunities.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An engineered spider silk protein comprising at least two units, wherein each unit comprises a polypeptide of SEQ ID NO: 4, a polypeptide of SEQ ID NO: 5, a polypeptide with 95% or greater homology to SEQ ID NO: 4, or a polypeptide with 95% or greater homology to SEQ ID NO: 5, wherein the engineered silk protein does not comprise SEQ ID NO: 12 and SEQ ID NO: 13, and
   wherein the engineered silk protein further comprises an N-terminal sequence having 95% or greater homology to any one SEQ ID NOs: 80-85 and/or a C-terminal sequence having 95% or greater homology to any one SEQ ID NOs: 86-92.

2. The engineered silk protein of claim 1, wherein the engineered silk protein polypeptide further comprises one or more units of SEQ ID NO: 1, SEQ ID NO: 2, SEQ ID NO: 3, SEQ ID NO: 6, or SEQ ID NO: 7, or one or more units with 95% or greater homology to SEQ ID NO: 1, SEQ ID NO: 2, SEQ ID NO: 3, SEQ ID NO: 6, SEQ ID NO: 7.

3. The engineered silk protein of claim 1, wherein at least two units is joined by a polypeptide linker.

4. The engineered silk protein of claim 1, further comprising a localization sequence, a detectable label, a therapeutic agent, or a combination thereof.

5. The engineered silk protein of claim 1, further comprising an operatively linked polypeptide to the at least two units.

6. The engineered silk protein of claim 1, having Young's modulus of about 3-10 GPa, an Ultimate Strength of about 200-800 MPa, an Extensibility of about 0.5-0.8 mm/mm, a Toughness of about 75-150 Mpa, or a combination thereof.

7. A synthetic material, comprising the engineered silk protein of claim 1.

8. The synthetic material of claim 7, comprising a textile, a pliant energy absorbing device, a medical device, a suture, a bandage, packaging, a tissue engineering material, or an implant.

9. The synthetic material of claim 7, in the form of a tissue engineering scaffold optionally comprising cells.

* * * * *

SEQUENCE LISTING

```
<160> NUMBER OF SEQ ID NOS: 92

<210> SEQ ID NO 1
<211> LENGTH: 36
<212> TYPE: PRT
<213> ORGANISM: Artificial Sequence
<220> FEATURE:
<223> OTHER INFORMATION: MaSp2 consensus

<400> SEQUENCE: 1

Gly Gly Tyr Gly Pro Gly Gly Gln Gly Pro Ser Gly Pro Gly Ser Gln
1               5                   10                  15

Gly Pro Gly Gly Ala Gly Pro Tyr Gly Pro Gly Gly Ala Ala Ala Ala
            20                  25                  30

Ala Ala Ala Ala
        35

<210> SEQ ID NO 2
<211> LENGTH: 44
<212> TYPE: PRT
<213> ORGANISM: Artificial Sequence
<220> FEATURE:
<223> OTHER INFORMATION: MaSp1a consensus
<220> FEATURE:
<221> NAME/KEY: VARIANT
<222> LOCATION: (4)..(4)
<223> OTHER INFORMATION: X4 is G or nonexistent such that X4X5X6 is GGA
      or nonexistant
<220> FEATURE:
<221> NAME/KEY: VARIANT
<222> LOCATION: (5)..(5)
<223> OTHER INFORMATION: X5 is G or nonexistent such that X4X5X6 is GGA
      or nonexistant
<220> FEATURE:
<221> NAME/KEY: VARIANT
<222> LOCATION: (6)..(6)
<223> OTHER INFORMATION: X6 is A or nonexistent such that X4X5X6 is GGA
      or nonexistant
<220> FEATURE:
<221> NAME/KEY: VARIANT
<222> LOCATION: (20)..(20)
<223> OTHER INFORMATION: X20 is G or nonexistent such that X20X21X22 is
      GAG or nonexistant
<220> FEATURE:
<221> NAME/KEY: VARIANT
<222> LOCATION: (21)..(21)
<223> OTHER INFORMATION: X21 is A or nonexistent such that X20X21X22 is
      GAG or nonexistant
<220> FEATURE:
<221> NAME/KEY: VARIANT
<222> LOCATION: (22)..(22)
<223> OTHER INFORMATION: X22 is G or nonexistent such that X20X21X22 is
```

```
        GAG or nonexistant
<220> FEATURE:
<221> NAME/KEY: VARIANT
<222> LOCATION: (30)..(30)
<223> OTHER INFORMATION: X30 is L or Q
<220> FEATURE:
<221> NAME/KEY: VARIANT
<222> LOCATION: (33)..(33)
<223> OTHER INFORMATION: X33 is L or Q
<220> FEATURE:
<221> NAME/KEY: VARIANT
<222> LOCATION: (35)..(35)
<223> OTHER INFORMATION: X35 is A or G
<220> FEATURE:
<221> NAME/KEY: VARIANT
<222> LOCATION: (37)..(37)
<223> OTHER INFORMATION: X37 is A or S

<400> SEQUENCE: 2

Gly Gly Ala Xaa Xaa Xaa Gly Gly Leu Gly Gly Gln Gly Gly Gly Gln
1               5                   10                  15

Gly Ala Gly Xaa Xaa Xaa Gln Gly Gly Tyr Gly Ser Gly Xaa Gly Gly
            20                  25                  30

Xaa Gly Xaa Gly Xaa Ala Ala Ala Ala Ala Ala Ala
        35                  40

<210> SEQ ID NO 3
<211> LENGTH: 41
<212> TYPE: PRT
<213> ORGANISM: Artificial Sequence
<220> FEATURE:
<223> OTHER INFORMATION: MaSp1b consensus
<220> FEATURE:
<221> NAME/KEY: VARIANT
<222> LOCATION: (34)..(34)
<223> OTHER INFORMATION: A or S

<400> SEQUENCE: 3

Gly Gly Ala Gly Gly Ala Gly Gly Leu Gly Gly Gln Gly Gly Gly Gln
1               5                   10                  15

Gly Ala Gly Gln Gly Gly Tyr Gly Ser Gly Gln Gly Gly Gln Gly Ala
            20                  25                  30

Gly Xaa Ala Ala Ala Ala Ala Ala Ala
        35                  40

<210> SEQ ID NO 4
<211> LENGTH: 63
<212> TYPE: PRT
<213> ORGANISM: Artificial Sequence
<220> FEATURE:
<223> OTHER INFORMATION: MaSp4a Consensus
<220> FEATURE:
<221> NAME/KEY: VARIANT
<222> LOCATION: (60)..(60)
<223> OTHER INFORMATION: A or T

<400> SEQUENCE: 4

Gly Pro Gly Pro Gln Gly Pro Ser Gly Pro Gly Pro Gln Gly Pro Tyr
1               5                   10                  15

Gly Pro Gly Pro Gln Gly Pro Gly Pro Gln Gly Pro Gly Pro Gln Gly
            20                  25                  30

Pro Ser Gly Pro Gly Pro Gln Arg Pro Gln Gly Pro Gly Pro Gln Gly
        35                  40                  45

Pro Tyr Gly Pro Gly Gly Val Ser Val Val Ser Xaa Thr Val Ser
    50                  55                  60
```

```
<210> SEQ ID NO 5
<211> LENGTH: 65
<212> TYPE: PRT
<213> ORGANISM: Artificial Sequence
<220> FEATURE:
<223> OTHER INFORMATION: MaSp4b consensus
<220> FEATURE:
<221> NAME/KEY: VARIANT
<222> LOCATION: (41)..(41)
<223> OTHER INFORMATION: Q or R

<400> SEQUENCE: 5

Gly Pro Gly Pro Gln Gly Pro Ser Gly Pro Gly Gln Pro Tyr
1               5                   10                  15

Gly Pro Gly Pro Gln Gly Pro Gly Pro Gln Gly Pro Gly Pro Gln Gly
            20                  25                  30

Pro Gly Pro Gln Gly Pro Gly Pro Xaa Gly Pro Ser Gly Pro Gly Pro
        35                  40                  45

Gln Gly Pro Tyr Gly Pro Gly Gly Val Ser Val Ser Ala Ser Val
    50                  55                  60

Ser
65

<210> SEQ ID NO 6
<211> LENGTH: 30
<212> TYPE: PRT
<213> ORGANISM: Artificial Sequence
<220> FEATURE:
<223> OTHER INFORMATION: MaSp1c consensus

<400> SEQUENCE: 6

Gly Ser Gly Gly Asp Gly Ser Gly Ser Gly Gly Tyr Gly Gly Arg Gly
1               5                   10                  15

Gly Gln Gly Gly Ala Gly Ser Ser Ala Ala Ala Ala Ala
            20                  25                  30

<210> SEQ ID NO 7
<211> LENGTH: 7
<212> TYPE: PRT
<213> ORGANISM: Artificial Sequence
<220> FEATURE:
<223> OTHER INFORMATION: MaSp5 consensus

<400> SEQUENCE: 7

Gly Gly Leu Gly Gly Ser Gly
1               5

<210> SEQ ID NO 8
<211> LENGTH: 507
<212> TYPE: PRT
<213> ORGANISM: Caerostris darwini

<400> SEQUENCE: 8

Leu Pro Gly Pro Gln Gly Pro Ser Gly Pro Gly Gln Pro Tyr
1               5                   10                  15

Gly Pro Gly Pro Gln Gly Pro Gly Pro Gln Gly Pro Gly Pro Gln Gly
            20                  25                  30

Pro Ser Gly Pro Gly Pro Gln Gln Pro Gln Gly Pro Gly Pro Gln Arg
        35                  40                  45

Pro Tyr Gly Pro Gly Gly Val Ser Val Val Ser Thr Val Ser Gly
    50                  55                  60

Pro Gly Pro Gln Gly Pro Leu Gly Pro Gly Ala Gln Val Pro Tyr Gly
65                  70                  75                  80
```

-continued

```
Pro Gly Pro Gln Val Pro Gly Pro Gln Gly Pro Gln Gly Pro
                85                  90                  95

Ser Gly Pro Gly Pro Gln Arg Pro Gln Gly Pro Gly Pro Gln Gly Pro
            100                 105                 110

Tyr Gly Pro Gly Gly Val Ser Val Ser Gln Thr Val Ser Gly Pro
            115                 120                 125

Gly Pro Gln Gly Pro Ser Gly Pro Gly Pro Gln Gly Pro Tyr Gly Pro
        130                 135                 140

Gly Pro Gln Gly Pro Gly Pro Gln Gly Pro Ala Pro Gln Gly Pro Ser
145                 150                 155                 160

Gly Pro Gly Pro Gln Arg Pro Gln Gly Pro Gly Pro Gln Arg Pro Tyr
            165                 170                 175

Gly Pro Gly Gly Ile Ser Val Val Ser Thr Thr Val Ser Gly Pro Gly
            180                 185                 190

Pro Gln Gly Pro Ser Ala Pro Gly Pro Gln Gly Pro Tyr Gly Pro Gly
        195                 200                 205

Pro Gln Val Pro Gly Pro Gln Gly Pro Gly Pro Gln Gly Pro Ser Gly
        210                 215                 220

Pro Gly Pro Gln Arg Pro Gln Gly Pro Gly Pro Gln Gly Pro Tyr Gly
225                 230                 235                 240

Pro Gly Gly Val Ser Val Val Ser Gln Thr Val Ser Gly Pro Gly Pro
            245                 250                 255

Gln Gly Pro Ser Gly Pro Gly Pro Gln Gly Pro Tyr Gly Pro Gly Pro
            260                 265                 270

Gln Gly Pro Gly Pro Gln Gly Pro Gly Pro Gln Gly Pro Ser Gly Ala
        275                 280                 285

Gly Pro Gln Arg Pro Gln Gly Pro Gly Pro Gln Gly Pro Tyr Gly Pro
        290                 295                 300

Gly Gly Val Ser Val Val Ser Ala Thr Val Ser Gly Pro Gly Pro Gln
305                 310                 315                 320

Gly Pro Ser Gly Pro Gly Pro Gln Gly Pro Tyr Gly Pro Gly Pro Gln
            325                 330                 335

Gly Pro Gly Pro Gln Arg Pro Val Pro Gln Gly Pro Ser Gly Pro Arg
            340                 345                 350

Pro Gln Gln Pro Gln Gly Pro Gly Pro Gln Arg Pro Phe Gly Pro Gly
        355                 360                 365

Gly Val Ser Ala Val Ser Thr Thr Val Phe Gly Pro Gly Pro Gln Gly
        370                 375                 380

Pro Ser Gly Pro Gly Pro Gln Gly Pro Tyr Gly Pro Gly Pro Gln Gly
385                 390                 395                 400

Pro Gly Pro Gln Gly Pro Gly Pro Gln Gly Pro Ser Gly Gln Gly Pro
            405                 410                 415

Gln Arg Pro Ser Gly Pro Arg Pro Gln Gly Pro Tyr Gly Pro Gly Gly
            420                 425                 430

Ile Ser Val Val Ser Ala Thr Val Ser Gly Pro Gly Pro Gln Gly Pro
            435                 440                 445

Ser Gly Pro Gly Pro Gln Arg Pro Tyr Gly Pro Gly Pro Glu Gly Pro
            450                 455                 460

Gly Pro Gln Gly Ala Gly Pro Gln Gly Pro Gly Leu Gln Arg Pro Ser
465                 470                 475                 480

Gly Pro Gly Pro Gln Gly Pro Tyr Gly Pro Gly Pro Arg Gly Pro Ser
            485                 490                 495
```

Ser Thr Pro Glu Ser Ala Ala Ile Asn Ala Ala
              500                 505

<210> SEQ ID NO 9
<211> LENGTH: 682
<212> TYPE: PRT
<213> ORGANISM: Caerostris darwini

<400> SEQUENCE: 9

Tyr Gly Pro Gly Gly Ala Ala Ala Ala Ala Ala Ala Gly Gly Tyr
  1               5                  10                  15

Gly Pro Gly Gly Ser Gly Pro Ser Gly Pro Gly Ser Gln Gly Pro Ser
             20                  25                  30

Gly Pro Gly Ser Gln Gly Pro Gly Ala Gly Pro Tyr Gly Pro Gly
             35                  40                  45

Gly Ala Ala Ala Ala Ala Ala Ala Gly Gly Tyr Gly Pro Gly Ser
             50                  55                  60

Gln Gly Pro Ser Gly Pro Gly Ser Gln Gly Pro Gly Gly Ala Gly Pro
 65                  70                  75                  80

Tyr Gly Pro Gly Gly Ala Ala Ala Ala Ala Ala Ala Gly Gly Tyr
                 85                  90                  95

Ala Pro Ala Gly Gln Gly Gln Ser Gly Pro Gly Ser Gln Gly Gln Gly
                100                 105                 110

Gln Ser Gly Pro Gly Ser Gln Gly Pro Gly Ala Gly Pro Tyr Gly
                115                 120                 125

Pro Gly Gly Ala Ala Ala Gly Gly Tyr Gly Pro Gly Gly Gln Gly
                130                 135                 140

Pro Ser Gly Pro Gly Ser Gln Gly Pro Gly Gly Arg Gly Pro Ser Gly
145                 150                 155                 160

Pro Gly Gly Ala Ala Ala Ala Ala Ser Ala Tyr Gly Pro Gly Gly
                165                 170                 175

Gln Gly Pro Ser Gly Pro Gly Ser Gln Gly Pro Gly Gly Gln Gly Pro
                180                 185                 190

Tyr Gly Pro Gly Ala Ala Ala Ala Ala Ala Ala Gly Gly Tyr Gly
                195                 200                 205

Pro Gly Gly Arg Gly Pro Ser Gly Pro Gly Ser Gln Gly Pro Ser Gly
                210                 215                 220

Pro Gly Ser Gln Gly Pro Gly Ala Gly Pro Tyr Gly Pro Gly Gly
225                 230                 235                 240

Ala Ala Ala Ala Ala Ala Ala Gly Gly Tyr Ala Pro Ala Gly Gln
                245                 250                 255

Gly Gln Ser Gly Pro Gly Ser Gln Gln Gly Gln Ser Gly Pro Gly
                260                 265                 270

Ser Gln Gly Pro Gly Gly Ala Gly Pro Tyr Gly Pro Gly Gly Ala Ala
                275                 280                 285

Ala Ala Ala Ala Ala Gly Gly Tyr Gly Pro Gly Gly Gln Gly Pro
                290                 295                 300

Ser Gly Pro Gly Ser Gln Gly Pro Ser Gln Gly Pro Ser Gly Pro
305                 310                 315                 320

Gly Leu Ala Ala Ala Ala Ala Ala Gly Gly Tyr Gly Pro Gly Gly
                325                 330                 335

Gln Gly Pro Ser Gly Ser Ala Ser Gln Gly Pro Gly Gly Gln Gly Pro
                340                 345                 350

Tyr Gly Pro Gly Gly Ala Ala Ala Ala Ala Ala Ala Gly Gly Tyr
                355                 360                 365

Gly Pro Gly Gly Ser Gly Pro Ser Gly Pro Gly Ser Gln Gly Pro Ser
        370                 375                 380

Gly Pro Gly Ser Gln Gly Pro Gly Gly Ala Gly Pro Tyr Gly Pro Gly
385                 390                 395                 400

Gly Ala Ala Ala Ala Ala Ala Ala Gly Gly Tyr Gly Pro Gly Ser
            405                 410                 415

Gln Gly Pro Ser Gly Pro Gly Ser Gln Gly Pro Gly Gly Arg Gly Pro
            420                 425                 430

Ser Gly Pro Gly Ser Gln Gly Pro Gly Gly Ala Gly Pro Tyr Gly Pro
            435                 440                 445

Gly Gly Ala Ala Ala Ala Ala Ala Ala Gly Gly Tyr Gly Pro Gly
        450                 455                 460

Ser Gln Gly Pro Ser Gly Pro Gly Ser Gln Gly Pro Gly Gly Gln Gly
465                 470                 475                 480

Pro Tyr Gly Pro Gly Gly Ala Ala Ala Ala Ala Ala Ala Gly Gly
            485                 490                 495

Tyr Gly Pro Gly Ser Gln Gly Pro Ser Gly Pro Gly Ser Gln Gly Pro
            500                 505                 510

Gly Gly Gln Gly Pro Tyr Gly Pro Ser Gly Ala Ala Ala Ala Ala
        515                 520                 525

Ala Ala Gly Gly Tyr Gly Pro Ala Gly Gln Gly Pro Ser Gly Pro Gly
        530                 535                 540

Ser Gln Gly Pro Gly Gly Gln Gly Pro Ser Gly Pro Gly Gly Tyr Gly
545                 550                 555                 560

Pro Ser Ser Ala Ala Ala Ala Phe Gly Gly Tyr Gly Pro Ser Gly Gln
            565                 570                 575

Ile Pro Ser Ala Ala Ala Ala Ser Arg Leu Ser Ser Pro Ala Val
            580                 585                 590

Ala Ser Arg Val Ser Ser Thr Val Ser Ser Leu Val Ser Ser Gly Pro
            595                 600                 605

Thr Ser Gln Gly Ala Leu Ser Asn Ala Ile Ser Asn Ala Val Ser Gln
610                 615                 620

Ile Ser Ala Ser Asn Pro Gly Leu Ser Gly Cys Asp Val Leu Val Gln
625                 630                 635                 640

Ala Leu Leu Glu Ile Val Ser Ala Leu Val His Ile Leu Gly Ser Ser
            645                 650                 655

Ser Val Gly Gln Val Ser Tyr Asn Thr Ala Gly Gln Ser Ala Ala Val
            660                 665                 670

Val Ser Gln Ser Ile Ser Gln Ala Leu Gly
            675                 680

<210> SEQ ID NO 10
<211> LENGTH: 544
<212> TYPE: PRT
<213> ORGANISM: Caerostris darwini

<400> SEQUENCE: 10

Ala Gly Gly Ala Gly Gly Arg Gly Gly Leu Gly Gly Gln Gly Gly Gly
1               5                   10                  15

Gln Gly Ala Gly Gly Ala Gly Gln Gly Gly Tyr Gly Ser Gly Leu Gly
            20                  25                  30

Gly Leu Gly Gly Ala Ala Ala Ala Ala Ala Ala Gly Gly Ala
        35                  40                  45

Gly Gly Leu Gly Gly Gln Gly Gly Gly Gln Gly Ala Gly Gln Gly Gly

-continued

```
            50                  55                  60
Tyr Gly Ser Gly Gln Gly Gln Gly Ala Gly Ser Ala Ala Ala
65                  70                  75                  80

Ala Ala Ala Gly Gly Ala Gly Arg Gly Gly Leu Gly Gly Gln Gly
                85                  90                  95

Gly Gly Gln Gly Ala Gly Gly Ala Gly Gln Gly Gly Tyr Gly Ser Gly
                100                 105                 110

Leu Gly Gly Leu Gly Gly Gly Ala Ala Ala Ala Ala Ala Gly
                115                 120                 125

Gly Ala Gly Gly Leu Gly Gly Gln Gly Gly Gln Gly Ala Gly Gln
130                 135                 140

Gly Gly Tyr Gly Ser Gly Gln Gly Gln Gly Ala Gly Ser Ala Ala
145                 150                 155                 160

Ala Ala Ala Ala Ala Gly Gly Arg Gly Gly Tyr Gly Gly Gln Gly Gly
                165                 170                 175

Gly Gln Gly Ala Gly Gly Ala Gly Gln Gly Gly Tyr Gly Ser Gly Leu
                180                 185                 190

Gly Gly Leu Gly Gly Gly Ala Ala Ala Ala Ala Ala Gly Gly
                195                 200                 205

Ala Gly Gly Leu Gly Gly Gln Gly Gly Gln Gly Ala Gly Gln Gly
                210                 215                 220

Gly Tyr Gly Ser Gly Gln Gly Gln Gly Ala Gly Ser Ala Ala
225                 230                 235                 240

Ala Ala Ala Ala Gly Gly Ala Gly Gly Leu Gly Gly Tyr Gly Gly Gln
                245                 250                 255

Gly Gly Gly Gln Gly Ala Gly Gly Ala Gly Gln Gly Gly Tyr Gly Ser
                260                 265                 270

Gly Leu Gly Gly Leu Gly Gly Gly Ala Ala Ala Ala Ala Ala
                275                 280                 285

Gly Gly Ala Gly Gly Leu Val Gly Gln Gly Gly Gln Gly Ala Gly
                290                 295                 300

Gln Gly Gly Tyr Gly Ser Gly Gln Gly Gly Gln Gly Ala Gly Ser Ala
305                 310                 315                 320

Ala Ala Ala Ala Ala Gly Gly Ala Gly Gly Arg Gly Gly Leu Gly
                325                 330                 335

Gly Gln Gly Gly Gln Gly Ala Gly Gly Ala Gly Gln Gly Gly Tyr
                340                 345                 350

Gly Ser Gly Leu Gly Gly Leu Gly Gly Gly Ala Ser Ala Ala Ala
                355                 360                 365

Ala Ala Gly Gly Ala Gly Gly Leu Gly Gly Gln Gly Gly Gln Gly
                370                 375                 380

Ala Gly Gln Gly Gly Tyr Gly Ser Gly Gln Gly Gln Gly Ala Gly
385                 390                 395                 400

Ser Ala Ala Ala Ala Ala Ala Ala Gly Gly Ser Gly Gly Leu Gly Gly
                405                 410                 415

Gln Gly Gly Tyr Gly Gly Gln Gly Gly Tyr Gly Gly Tyr Gly Gly
                420                 425                 430

Gln Gln Val Ala Ala Ser Ala Thr Thr Ala Ser Ala Ala Ala Ser Arg
                435                 440                 445

Leu Ser Ser Pro Ala Ala Ser Ser Arg Val Ser Ser Ala Val Ser Ser
450                 455                 460

Leu Val Ser Ser Gly Pro Thr Ser Pro Ala Ala Leu Ser Asn Thr Ile
465                 470                 475                 480
```

```
Ser Asn Val Val Ser Gln Val Gly Ala Ser Asn Pro Gly Leu Ser Gly
            485                 490                 495

Cys Asp Val Leu Val Gln Ala Leu Leu Glu Ile Val Ser Ala Leu Ile
            500                 505                 510

His Ile Leu Gly Ser Ser Ile Gly Gln Val Asn Tyr Gly Ala Thr
        515                 520                 525

Ala Gln Ser Thr Gly Ile Val Ser Gln Ser Ile Ser Gln Ala Leu Gly
        530                 535                 540

<210> SEQ ID NO 11
<211> LENGTH: 478
<212> TYPE: PRT
<213> ORGANISM: Caerostris darwini

<400> SEQUENCE: 11

Gln Gly Gly Gly Gln Gly Ala Gly Gln Gly Gly Tyr Gly Ser Gly Gln
1               5                   10                  15

Gly Gly Gln Gly Ala Gly Ser Ala Ala Ala Ala Ala Ala Gly Gly
            20                  25                  30

Arg Gly Gly Tyr Gly Gly Gln Gly Gly Gln Gly Ala Gly Ala
            35                  40                  45

Gly Gln Gly Gly Tyr Gly Ser Gly Leu Gly Gly Leu Gly Gly Ala
    50                  55                  60

Ala Ala Ala Ala Gly Ala Gly Gly Leu Gly Gln Gly Gly Gly
65                  70                  75                  80

Gln Gly Ala Gly Gln Gly Gly Tyr Gly Ser Gly Gln Gly Gly Gln Gly
                85                  90                  95

Ala Gly Ser Ala Ala Ala Ala Ala Ala Gly Gly Arg Gly Gly Tyr
            100                 105                 110

Gly Gly Gln Gly Gly Gln Gly Ala Gly Ala Gly Gln Gly Gly
        115                 120                 125

Tyr Gly Ser Gly Leu Gly Gly Leu Gly Gly Ala Ala Ala Ala Ala
    130                 135                 140

Ala Ala Ala Gly Gly Ala Gly Gly Leu Ala Gly Gln Gly Gly Gly Gln
145                 150                 155                 160

Gly Ala Gly Gln Gly Gly Tyr Gly Ser Gly Gln Gly Gly Gln Gly Ala
            165                 170                 175

Gly Ser Ala Ala Ala Ala Ala Ala Gly Gly Ala Gly Gly Arg Gly
        180                 185                 190

Gly Tyr Gly Gly Gln Gly Gly Gln Gly Ala Gly Ala Gly Gln Gly
    195                 200                 205

Gly Tyr Gly Ser Gly Leu Gly Gly Leu Gly Gly Ala Ala Ala Ala
    210                 215                 220

Ala Ala Ala Ala Gly Gly Ala Gly Gly Leu Gly Gln Gly Gly Gly
225                 230                 235                 240

Gln Gly Ala Gly Gln Gly Gly Tyr Gly Ser Gln Gly Gly Gln Gly
            245                 250                 255

Ala Gly Ser Ala Ala Ala Ala Ala Ala Gly Gly Ala Gly Gly Gln
        260                 265                 270

Gly Gly Tyr Gly Gly Gln Gly Gly Gln Gly Ala Gly Ala Gly Gln
    275                 280                 285

Gly Gly Tyr Gly Ser Gly Leu Gly Gly Val Gly Gly Ala Ala Ala
    290                 295                 300

Gly Gly Ala Gly Gly Leu Gly Gly Gln Gly Gly Gly Gln Gly Ala Gly
```

```
                305                 310                 315                 320
Gln Gly Gly Tyr Gly Ser Gly Gln Gly Gly Gln Gly Ala Gly Ser Ala
                    325                 330                 335

Ala Ala Ala Ser Ala Ala Gly Gly Ala Leu Gly Leu Gly Gly Gln Gly
                    340                 345                 350

Gly Tyr Gly Gly Gln Met Gly Tyr Gly Gly Gly Tyr Gly Gly Gln Gln
                    355                 360                 365

Val Ala Ala Ser Ala Ala Thr Ala Ser Ala Ala Ser Arg Leu Ser
        370                 375                 380

Ser Pro Asp Ala Ser Ser Arg Val Ser Ala Val Ser Ser Leu Val
385                 390                 395                 400

Ser Ser Gly Pro Thr Asn Pro Ala Ala Leu Ser Asn Thr Ile Gly Ser
                    405                 410                 415

Val Val Ser Gln Ile Gly Ala Ser Asn Pro Gly Leu Ser Gly Cys Asp
                    420                 425                 430

Ile Leu Val Gln Ala Leu Leu Glu Ile Val Ser Ala Leu Ile Gln Ile
                    435                 440                 445

Leu Ala Ser Ser Ser Ile Gly His Val Asn Tyr Gly Ala Thr Ala Gln
                    450                 455                 460

Ser Thr Gly Ile Val Ser Gln Ser Ile Ser Gln Ala Leu Gly
465                 470                 475

<210> SEQ ID NO 12
<211> LENGTH: 687
<212> TYPE: PRT
<213> ORGANISM: Caerostris darwini

<400> SEQUENCE: 12

Pro Gln Ser Pro Tyr Gly Pro Gly Pro Gln Gly Pro Gly Pro Gln Gly
1               5                   10                  15

Pro Gly Pro Gln Gly Pro Ser Gly Pro Gly Pro Gln Arg Pro Gln Gly
                20                  25                  30

Pro Gly Pro Gln Gly Pro Tyr Gly Pro Gly Val Ser Val Val Ser
            35                  40                  45

Ala Thr Val Ser Gly Pro Gly Pro Gln Gly Pro Ser Gly Pro Gly Pro
        50                  55                  60

Gln Gly Pro Tyr Gly Pro Gly Pro Gln Gly Pro Gly Pro Gln Gly Pro
65                  70                  75                  80

Gly Pro Gln Leu Pro Gly Pro Gln Gly Pro Ser Gly Pro Gly Pro Gln
                85                  90                  95

Gly Pro Tyr Gly Pro Gly Pro Gln Gly Pro Gly Pro Gln Gly Pro Gly
            100                 105                 110

Pro Gln Gly Pro Ser Gly Pro Gly Pro Gln Gly Pro Gln Gly Pro Gly
        115                 120                 125

Pro Gln Arg Pro Tyr Gly Pro Gly Gly Val Ser Val Val Ser Thr Thr
    130                 135                 140

Val Ser Gly Pro Gly Pro Gln Gly Pro Leu Pro Gly Ala Gln Val
145                 150                 155                 160

Pro Tyr Gly Pro Gly Pro Gln Val Pro Gly Pro Gln Gly Pro Gly Pro
                165                 170                 175

Gln Gly Pro Ser Gly Pro Gly Pro Gln Arg Pro Gln Gly Pro Gly Pro
            180                 185                 190

Gln Gly Pro Tyr Gly Pro Gly Gly Val Ser Val Val Ser Gln Thr Val
        195                 200                 205
```

```
Ser Gly Pro Gly Pro Gln Gly Pro Ser Gly Pro Gly Pro Gln Gly Pro
210                 215                 220

Tyr Gly Pro Gly Pro Gln Gly Pro Gly Pro Gln Gly Pro Ala Pro Gln
225                 230                 235                 240

Gly Pro Ser Gly Pro Gly Pro Gln Arg Pro Gln Gly Pro Gly Pro Gln
            245                 250                 255

Arg Pro Tyr Gly Pro Gly Gly Ile Ser Val Val Ser Thr Thr Val Ser
            260                 265                 270

Gly Pro Gly Pro Gln Gly Pro Ser Ala Pro Gly Pro Gln Gly Pro Tyr
            275                 280                 285

Gly Pro Gly Pro Gln Val Pro Gly Pro Gln Gly Pro Gly Pro Gln Gly
            290                 295                 300

Pro Ser Gly Pro Gly Pro Gln Arg Pro Gln Gly Pro Gly Pro Gln Gly
305                 310                 315                 320

Pro Tyr Gly Pro Gly Gly Val Ser Val Val Ser Gln Thr Val Ser Gly
            325                 330                 335

Pro Gly Pro Gln Gly Pro Ser Gly Pro Gly Pro Gln Gly Pro Tyr Gly
            340                 345                 350

Pro Gly Pro Gln Gly Pro Gly Pro Gln Gly Pro Gly Pro Gln Gly Pro
            355                 360                 365

Ser Gly Ala Gly Pro Gln Arg Pro Gln Gly Pro Gly Pro Gln Gly Pro
370                 375                 380

Tyr Gly Pro Gly Gly Val Ser Val Val Ser Ala Thr Val Ser Gly Pro
385                 390                 395                 400

Gly Pro Gln Gly Pro Ser Gly Pro Gly Pro Gln Gly Pro Tyr Gly Pro
            405                 410                 415

Gly Pro Gln Gly Pro Gly Pro Gln Arg Pro Val Pro Gln Gly Pro Ser
            420                 425                 430

Gly Pro Arg Pro Gln Gln Pro Gln Gly Pro Gly Pro Gln Arg Pro Phe
            435                 440                 445

Gly Pro Gly Gly Val Ser Ala Val Ser Thr Thr Val Phe Gly Pro Gly
            450                 455                 460

Pro Gln Gly Pro Ser Gly Pro Gly Pro Gln Gly Pro Tyr Gly Pro Gly
465                 470                 475                 480

Pro Gln Gly Pro Gly Pro Gln Gly Pro Gly Pro Gln Gly Pro Ser Gly
            485                 490                 495

Gln Gly Pro Gln Arg Pro Ser Gly Pro Arg Pro Gln Gly Pro Tyr Gly
            500                 505                 510

Pro Gly Gly Ile Ser Val Val Ser Ala Thr Val Ser Gly Pro Gly Pro
            515                 520                 525

Gln Gly Pro Ser Gly Pro Gly Pro Gln Arg Pro Tyr Gly Pro Gly Pro
            530                 535                 540

Glu Gly Pro Gly Pro Gln Gly Ala Gly Pro Gln Gly Pro Gly Leu Gln
545                 550                 555                 560

Arg Pro Ser Gly Pro Gly Pro Gln Gly Pro Tyr Gly Pro Gly Pro Arg
            565                 570                 575

Gly Pro Ser Ser Thr Pro Glu Ser Ala Ala Ile Asn Ala Ala Ser Arg
            580                 585                 590

Leu Ser Pro Ala Ala Ser Ser Arg Val Ser Ser Thr Val Ser Gln
            595                 600                 605

Leu Val Ser Ser Gly Pro Pro Asn Ser Ala Ala Val Ser Gly Ala Ile
            610                 615                 620

Ser Ser Leu Val Ser Gln Val Ser Ala Ser Asn Pro Gly Leu Ser Gly
```

```
                625                 630                 635                 640

Cys Asp Ile Leu Val Gln Ala Leu Met Glu Leu Leu Ser Ala Leu Val
                    645                 650                 655

Ser Ile Val Gly Ser Ser Ile Gly Gln Val Asn Tyr Gly Ala Ser
                660                 665                 670

Gly Gln Tyr Ala Gln Leu Val Ser Gln Ala Ile Gly Gln Ala Phe
                675                 680                 685
```

<210> SEQ ID NO 13
<211> LENGTH: 491
<212> TYPE: PRT
<213> ORGANISM: Caerostris darwini

<400> SEQUENCE: 13

```
Pro Gln Gly Pro Tyr Gly Pro Gly Pro Gln Gly Pro Gly Pro Gln Gly
1               5                   10                  15

Pro Gly Pro Gln Gly Pro Gly Pro Gln Gly Pro Gly Pro Arg Gly Pro
                20                  25                  30

Ser Gly Pro Gly Pro Gln Gly Pro Tyr Gly Pro Gly Gly Val Ser Val
            35                  40                  45

Val Ser Ala Ser Val Ser Gly Pro Gly Pro Gln Gly Pro Ser Gly Pro
        50                  55                  60

Gly Pro Gln Gly Pro Tyr Gly Pro Gly Pro Gln Gly Pro Gly Pro Gln
65                  70                  75                  80

Gly Pro Gly Pro Gln Gly Pro Gly Pro Gln Gly Pro Gly Pro Arg Gly
                85                  90                  95

Pro Ser Gly Pro Gly Pro Gln Gly Pro Tyr Gly Pro Gly Gly Val Ser
                100                 105                 110

Val Ala Ser Ala Ser Val Ser Gly Pro Gly Pro Gln Gly Pro Ser Gly
            115                 120                 125

Pro Gly Pro Gln Gly Pro Tyr Gly Pro Gly Pro Gln Gly Pro Gly Pro
        130                 135                 140

Arg Gly Pro Gly Pro Gln Gly Pro Gly Pro Gln Gly Pro Gly Pro Gln
145                 150                 155                 160

Gly Pro Ser Gly Pro Gly Pro Gln Gly Pro Tyr Gly Pro Gly Gly Val
                165                 170                 175

Ser Val Val Ser Ala Ser Val Ser Gly Pro Gly Pro Gln Gly Pro Ser
            180                 185                 190

Gly Pro Gly Pro Gln Gly Pro Tyr Gly Pro Gly Pro Gln Gly Pro Gly
        195                 200                 205

Pro Gln Gly Pro Gly Pro Gln Gly Pro Gly Pro Gln Gly Pro Gly Pro
        210                 215                 220

Arg Gly Pro Ser Gly Pro Gly Pro Gln Gly Pro Tyr Gly Pro Gly Gly
225                 230                 235                 240

Val Ser Val Val Ser Ala Ser Val Ser Gly Pro Gly Pro Gln Gly Pro
                245                 250                 255

Ser Gly Pro Gly Pro Gln Gly Pro Tyr Gly Pro Gly Pro Gln Gly Pro
            260                 265                 270

Gly Pro Gln Val Pro Gly Pro Gln Gly Pro Gly Pro Gln Gly Pro Gly
        275                 280                 285

Pro Gln Gly Pro Ser Gly Pro Gly Pro Gln Gly Pro Tyr Gly Pro Gly
        290                 295                 300

Gly Val Ser Val Val Ser Ala Ser Val Ser Gly Pro Gly Pro Gln Gly
305                 310                 315                 320
```

```
Pro Ser Gly Pro Gly Pro Gln Gly Pro Tyr Gly Pro Gly Pro Gln Gly
            325                 330                 335

Pro Gly Pro Arg Gly Pro Gly Pro Gln Gly Pro Gly Pro Gln Gly Pro
        340                 345                 350

Gly Pro Gln Gly Pro Ser Gly Pro Gln Gly Pro Tyr Gly Pro
        355                 360                 365

Gly Gly Val Ser Val Ser Ala Ser Val Ser Gly Pro Gly Pro Gln
    370                 375                 380

Gly Pro Ser Gly Pro Ala Val Asn Ala Ala Arg Leu Ser Ser Pro
385                 390                 395                 400

Asp Ala Ser Ser Arg Val Ser Thr Val Ser Gln Leu Val Ser Gly
                405                 410                 415

Gly Pro Thr Ser Gly Ala Ala Val Ser Asn Ala Leu Ser Ser Leu Val
        420                 425                 430

Ser Gln Val Gly Ala Ser Asn Pro Gly Leu Ser Gly Cys Asp Ile Leu
            435                 440                 445

Val Gln Ala Leu Met Glu Met Leu Ser Ala Leu Val Ser Ile Val Gly
        450                 455                 460

Ser Ser Ser Ile Gly Gln Val Asn Tyr Gly Ala Ser Gly Gln Tyr Thr
465                 470                 475                 480

Gln Met Ile Gly Gln Ala Ile Ala Gln Ala Phe
            485                 490

<210> SEQ ID NO 14
<211> LENGTH: 388
<212> TYPE: PRT
<213> ORGANISM: Caerostris darwini
<220> FEATURE:
<221> NAME/KEY: misc_feature
<222> LOCATION: (35)..(35)
<223> OTHER INFORMATION: Xaa can be any naturally occurring amino acid

<400> SEQUENCE: 14

Gly Arg Gly Gly Tyr Gly Gly Arg Gly Gly Ala Gly Ser Ser Ser Ala
1               5                   10                  15

Ala Ala Ala Ala Gly Ser Gly Gly Asp Gly Ser Gly Ser Gly Gly Tyr
            20                  25                  30

Gly Gly Xaa Gly Gly Gln Gly Gly Asp Gly Ala Ser Ser Ala Ala Ala
        35                  40                  45

Ala Ala Gly Ser Gly Gly Asp Gly Ser Gly Ser Gly Gly Tyr Gly Gly
    50                  55                  60

Arg Gly Gly Arg Gly Gly Gln Gly Gly Ala Gly Ser Ser Ser Ala Ala
65                  70                  75                  80

Ala Ala Ala Gly Ser Gly Gly Asp Gly Ser Gly Ser Gly Gly Tyr Gly
                85                  90                  95

Gly Arg Gly Gly Arg Gly Gly Ala Gly Ser Ser Ser Ala Ala Ser Ala
            100                 105                 110

Ala Ala Gly Gly Glu Asp Gly Phe Gly Arg Gly Tyr Gly Gly Arg
        115                 120                 125

Gly Gly Ala Ser Ser Ser Ala Ala Ala Ala Gly Ser Gly Gly
        130                 135                 140

Asp Gly Ser Gly Ser Gly Gly Tyr Gly Gly Arg Gly Gly Gln Gly Gly
145                 150                 155                 160

Ala Gly Ser Ser Ser Ala Ala Ala Ala Gly Ser Gly Gly Asp Gly Tyr
                165                 170                 175

Gly Ser Gly Gly Tyr Gly Gly Arg Gly Gly Gln Gly Gly Ala Gly Ser
```

-continued

```
                180             185                 190
Ser Ser Ala Ala Ser Ala Gly Ser Gly Gly Asp Gly Phe Gly Ser
            195                 200                 205
Gly Phe Tyr Gly Gly Arg Gly Gly Glu Gly Gly Ala Gly Ser Ser Ser
            210                 215                 220
Ala Ala Ala Ala Ala Gly Ser Gly Gly Asp Gly Tyr Gly Ser Gly Gly
225                 230                 235                 240
Tyr Gly Gly Arg Gly Gly Gln Gly Gly Ala Gly Gly Ala Ser Ala Ser
                245                 250                 255
Ala Val Ala Ala Gly Gly Gly Arg Gly Gln Gly Gly Tyr Gly Gly Arg
                260                 265                 270
Gly Gly Gln Gly Gly Ala Gly Ser Ser Ser Ala Ser Ser Thr Ala Ser
                275                 280                 285
Ala Ala Ala Ser Arg Leu Tyr Ser Pro Asp Ser Ser Ala Arg Ile Ser
                290                 295                 300
Ser Ala Val Ser Ser Leu Ala Ser Tyr Gly Pro Asn Asn Pro Thr Ala
305                 310                 315                 320
Leu Ser Asp Val Ile Ser Asn Thr Met Ser Gln Val Ser Tyr Ser Ser
                325                 330                 335
Pro Glu Leu Ser Gly Cys Asp Val Leu Val Gln Thr Leu Met Glu Val
                340                 345                 350
Val Ser Ala Leu Val His Ile Leu Ser Val Ser Asp Ile Gly Pro Val
                355                 360                 365
Ala Tyr Asp Ser Asp Gln Ala Val Gln Val Val Gly Gln Ser Phe Asn
                370                 375                 380
Asn Leu Met Tyr
385

<210> SEQ ID NO 15
<211> LENGTH: 436
<212> TYPE: PRT
<213> ORGANISM: Caerostris darwini

<400> SEQUENCE: 15

Gly Gly Leu Gly Asp Ser Gly Gly Gly Leu Gly Gly Ser Arg Gly Gly
1               5                   10                  15
Leu Gly Gly Ser Gly Gly Gly Leu Gly Gly Ser Gly Gly Gly Leu Gly
                20                  25                  30
Gly Ser Gly Gly Gly Leu Gly Gly Ser Gly Gly Gly Leu Gly Gly Ser
            35                  40                  45
Gly Gly Gly Gln Gly Gly Ser Glu Gly Gly Leu Gly Gly Ser Gly Gly
            50                  55                  60
Gly Leu Gly Gly Ser Ser Gly Arg Leu Gly Gly Ser Gly Gly Arg Leu
65                  70                  75                  80
Gly Gly Ser Gly Gly Gly Leu Gly Arg Ser Gly Gly Gly Ile Gly Gly
                85                  90                  95
Ser Gly Gly Gly Leu Gly Gly Ser Gly Arg Gly Leu Gly Gly Ser Gly
                100                 105                 110
Val Gly Pro Gly Gly Ser Gly Gly Gly Leu Gly Asp Ser Gly Gly Gly
                115                 120                 125
Leu Gly Gly Ser Gly Gly Gly Val Gly Gly Ser Gly Gly Gly Leu Gly
            130                 135                 140
Asp Ser Gly Gly Arg Leu Gly Ser Ser Gly Ser Val Gly Gly Ser Gly
145                 150                 155                 160
```

```
Gly Arg Gly Gly Leu Gly Gly Pro Gly Ser Gly Gly Thr Asp Gly
            165                 170                 175

Gln Gly Ala Met Gly Gly Ser Gly Gly Arg Gly Leu Asp Gly Pro Gly
        180                 185                 190

Ser Leu Gly Gly Thr Gly Gly Gln Gly Gly Met Asp Gly Pro Gly Gly
        195                 200                 205

Gly Val Asp Gly Asp Tyr Ser Ala Ser Ala Ser Ser Arg Gly Leu
    210                 215                 220

Gly Gly Ser Gly Pro Gly Gly Tyr Gly Arg Ser Leu Gly Gly Pro Gly
225                 230                 235                 240

Gly Phe Gly Gly Asp Arg Asp Leu Gly Asp Ser Ala Ser Ser Ala Ala
            245                 250                 255

Ala Ser Ala Gly Gly Asp Gly Gly Ser Ser Gly Pro Gly Lys Arg Gly
            260                 265                 270

Gly Tyr Gly Arg Gly Ser Gly Gly Ala Lys Gly Leu Ser Gly Ser Gly
            275                 280                 285

Gly Gly Ile Gly Ser Gly Ala Ala Ala Thr Leu Ala Gly Gly Leu Gly
            290                 295                 300

Gly Ser Leu Ser Ala Gly Ser Gly Glu Phe Leu Gly Thr Ser Gly Gly
305                 310                 315                 320

Arg Gly Gly Asp Ser Ser Gln Thr Ser Ala Ser Ser Thr Ile Ser Ser
            325                 330                 335

Ala Ala Ser Arg Leu Ser Ser Pro Glu Ala Ser Ser Arg Ile Ser Ser
            340                 345                 350

Val Val Ser Ser Phe Leu Ser Asn Gly Ile Asp Asn Pro Ser Ser Leu
            355                 360                 365

Ser Ser Ser Leu Ser Gly Ile Val Ser Arg Ile Ser Ser Leu Asn Pro
370                 375                 380

Met Leu Ser Ser Cys Asp Ile Leu Leu Gln Ala Leu Leu Glu Ile Val
385                 390                 395                 400

Ser Ala Leu Leu Gln Ile Leu Ala Ser Ser Asn Ile Gly Pro Ile Asp
            405                 410                 415

Tyr Ser Ser Thr Arg Gln Ser Thr Gly Ile Val Ser Gln Ser Val Tyr
            420                 425                 430

Gln Ala Phe Ser
        435

<210> SEQ ID NO 16
<211> LENGTH: 183
<212> TYPE: PRT
<213> ORGANISM: Caerostris darwini

<400> SEQUENCE: 16

Gly Ala Gly Gly Ala Gly Arg Gly Gly Tyr Gly Gly Gly Ser Gly
1               5                   10                  15

Ala Gly Ala Gly Ala Ala Ala Ala Gly Ala Gly Ala Gly Gly Gly
            20                  25                  30

Tyr Gly Gly Gln Gly Gly Tyr Gly Gly Ser Gly Ser Ala Ala
            35                  40                  45

Gly Gly Ala Ser Ala Ala Gly Ala Ala Val Gly Ser Tyr Gly Ser Gly
        50                  55                  60

Gly Tyr Gly Gly Gly Ala Ser Tyr Ala Ser Ser Ala Gly Ser Val
65                  70                  75                  80

Val Asn Thr Val Ser Ser Arg Ile Thr Ser Ser Glu Ser Ser Arg
            85                  90                  95
```

```
Ile Ser Ser Ala Ala Ser Thr Leu Thr Ala Gly Gly Ala Leu Asn Ala
            100                 105                 110

Ala Ala Leu Ser Asp Val Ile Gly Asn Val Tyr Ser Gln Val Ser Ala
        115                 120                 125

Ser Ala Gly Gly Ala Ser Gly Ala Glu Val Leu Val Gln Thr Leu Leu
    130                 135                 140

Glu Ile Val Ser Ala Leu Leu His Ile Leu Ser Ser Ser Asn Ile Gly
145                 150                 155                 160

Tyr Val Asp Phe Gly Gly Val Ser Ser Ala Asn Ala Val Ala Gln
                165                 170                 175

Ser Val Ala Ala Ala Leu Gly
            180
```

<210> SEQ ID NO 17
<211> LENGTH: 509
<212> TYPE: PRT
<213> ORGANISM: Caerostris darwini

<400> SEQUENCE: 17

```
Ala Leu Gly Ser Gly Gly Phe Arg Gly Phe Gly Gly Pro Gly Gly
1               5                   10                  15

Pro Gly Gly Pro Gly Gly Pro Gly Ala Pro Gly Ala Pro Gly Gly Pro
                20                  25                  30

Gly Val Gly Gly Pro Gly Gly Tyr Tyr Gly Pro Gly Ala Gly Gly Ala
            35                  40                  45

Gly Gly Met Leu Gly Ser Gly Ala Gly Gly Val Ser Gly Gly Pro Gly
        50                  55                  60

Gly Leu Gly Gly Pro Gly Gly Phe Gly Gly Pro Gly Gly Val Gly Gly
65                  70                  75                  80

Leu Gly Gly Met Gly Gly Val Gly Pro Gly Gly Ser Gly Ile Met Tyr
                85                  90                  95

Gly Pro Gly Ala Gly Gly Ala Gly Gly Phe Gly Ser Gly Ala Gly
            100                 105                 110

Gly Ala Ala Gly Gly Gln Gly Gly Phe Gly Gly Ala Gly Gly Pro Gly
        115                 120                 125

Gly Pro Gly Gly Ala Gly Gly Pro Gly Ala Ala Gly Gly Val Gly Gly
    130                 135                 140

Ile Ser Gly Pro Gly Gly Ala Gly Pro Ser Gly Gly Ala Gly Gly
145                 150                 155                 160

Val Thr Val Val Asp Asn Leu Ser Val Asn Val Gly Gly Ala Gly Ala
                165                 170                 175

Gly Gly Ala Gly Thr Gly Gly Ala Gly Gly Ser Leu Gly Gly Leu Gly
            180                 185                 190

Gly Phe Gly Gly Pro Gly Gly Pro Gly Gly Pro Gly Gly Pro Gly Gly
        195                 200                 205

Pro Gly Gly Ser Gly Ala Ala Gly Gly Met Thr Gly Pro Gly Ala Gly
    210                 215                 220

Gly Ser Ala Gly Gly Ala Gly Gly Ser Gly Pro Ile Thr Ile Ser Gly
225                 230                 235                 240

Thr Leu Ser Val Gly Gly Ala Gly Ala Gly Gly Ala Gly Pro Gly Ala
                245                 250                 255

Gly Gly Arg Tyr Gly Ser Gly Gly Ser Gly Gly Ala Gly Gly Phe
            260                 265                 270

Gly Gly Pro Gly Gly Pro Gly Gly Pro Gly Gly Pro Gly Gly Pro Gly
```

-continued

```
                275                 280                 285
Gly Leu Gly Gly Ala Gly Ala Gly Gly Val Gly Pro Gly Thr Gly Gly
            290                 295                 300
Ala Ser Ser Pro Gly Gly Gly Ser Gly Pro Val Thr Val Thr Asp Asn
305                 310                 315                 320
Val Ser Val Thr Val Gly Gly Ser Gly Gly Ser Gly Gly Ser Asp Ala
                325                 330                 335
Gly Gly Ala Gly Gly Ala Leu Gly Ser Gly Gly Phe Arg Gly Phe
            340                 345                 350
Gly Gly Pro Gly Gly Pro Gly Gly Pro Gly Gly Pro Gly Ala Pro Gly
                355                 360                 365
Ala Pro Gly Gly Ala Gly Ala Gly Ile Ile Gly Gly Ala Pro Ser Pro
            370                 375                 380
Ser Gly Gly Ser Ser Gly Pro Val Thr Val Ser Asp Asn Ile Ser Ile
385                 390                 395                 400
Thr Ile Gly Gly Gln Met Ser Ser Ala Gly Ser Ala Gly Pro Gly Phe
                405                 410                 415
Gln Gly Gln Pro Val Val Ser Arg Leu Pro Ser Leu Val Asn Gly Met
            420                 425                 430
Leu Gly Ser Met Gln Ala Asn Gly Leu Asn Tyr Gln Asn Leu Gly Asn
            435                 440                 445
Leu Leu Ser Arg Tyr Ser Thr Gly Ser Gly Thr Cys Asn Ser Asn Asp
            450                 455                 460
Leu Asn Leu Leu Met Glu Ala Leu Gln Ala Ala Leu His Cys Leu Ser
465                 470                 475                 480
Tyr Pro Gly Pro Ala Ser Val Pro Ser Met Pro Pro Pro Ser Ser Thr
                485                 490                 495
Ser Ala Tyr Met Gln Ser Ile Arg Arg Val Phe Gly Tyr
                500                 505

<210> SEQ ID NO 18
<211> LENGTH: 344
<212> TYPE: PRT
<213> ORGANISM: Caerostris darwini

<400> SEQUENCE: 18

Ala Ala Ser Glu Ala Ser Ser Ser Ala Ser Ser Ser Ser Ala Ser
1               5                   10                  15
Ala Phe Ala Gln Ser Ala Ser Gln Ser Leu Ala Met Ser Ser Ser Phe
                20                  25                  30
Ala Ser Ala Phe Ser Ala Ala Ala Ser Ser Ala Glu Ser Leu Arg Ser
            35                  40                  45
Leu Gly Phe Gln Ile Gly Asn Ala Leu Val Asn Asn Leu Gly Leu Arg
            50                  55                  60
Leu Gln Pro Ala Asp Val Ala Gln Ala Leu Ser Ala Val Gly Thr Gly
65                  70                  75                  80
Ala Ser Thr Asn Ala Tyr Ala Asn Ala Leu Ser Ala Val Ala Arg
                85                  90                  95
Ala Ala Ala Ser Gln Gly Thr Leu Asn Ala Gly Asn Ser Gly Ser Leu
                100                 105                 110
Ala Ser Ala Ala Ser Ala Ala Ile Ser Ala Ala Ala Ser Ala Ser
            115                 120                 125
Ser Ser Gln Phe Gln Ser Ala Ala Gln Gln Ala Ala Ala Ala
            130                 135                 140
```

Ala Phe Arg Gln Ala Ala Ser Gln Ser Gly Ser Gln Ser Ala Ala Arg
145                 150                 155                 160

Ser Gly Ser Gln Ser Ser Ser Ala Thr Thr Thr Thr Ser Gly
            165                 170                 175

Ser Gln Ala Ala Ser Glu Ala Ala Ser Arg Arg Ala Gly Ala Ser Ala
            180                 185                 190

Gly Ala Gly Ser Asn Ala Gly Ala Phe Gly Ala Ala Phe Gly Arg Ser
            195                 200                 205

Ala Gly Gly Thr Gly Ala Asn Ala Gly Ala Phe Gly Ala Ala Leu Gly
        210                 215                 220

Arg Pro Val Gly Gln Asp Val Ala Pro Ser Leu Gln Ser Ala Leu Ala
225                 230                 235                 240

Pro Val Leu Ser Ser Val Leu Ser Ser Asp Ala Thr Ala Arg
            245                 250                 255

Val Asn Ser Leu Ala Glu Ser Val Ser Ser Ala Ile Ala Ser Ser Gly
            260                 265                 270

Gly Ser Leu Asn Val Ala Thr Phe Leu Asp Ser Leu Ser Ser Val Gly
        275                 280                 285

Ser Gln Val Arg Ser Gly Thr Ser Leu Asp Ala Ser Gln Ala Thr Ser
290                 295                 300

Glu Val Leu Leu Glu Ala Ile Ala Ala Leu Ile Lys Val Ile Asn Gly
305                 310                 315                 320

Ala Gly Ile Thr Arg Val Asn Leu Asp Asn Val Ser Asn Val Asn Ser
            325                 330                 335

Ala Leu Val Ser Ala Leu Ala Gly
            340

<210> SEQ ID NO 19
<211> LENGTH: 264
<212> TYPE: PRT
<213> ORGANISM: Caerostris darwini

<400> SEQUENCE: 19

Gly Tyr Gly Gly Gly Ala Gly Ala Gly Ala Gly Ala Ala Gly Ala Gly
1               5                   10                  15

Gly Ala Gly Gly Tyr Gly Gly Tyr Gly Gly Gly Ala Gly Ala Gly
            20                  25                  30

Ala Gly Ala Ala Gly Ala Gly Gly Ala Gly Tyr Gly Gly Tyr
        35                  40                  45

Gly Gly Gly Ala Gly Ala Gly Ala Ala Ala Gly Ala Gly Ala Gly Gly
        50                  55                  60

Arg Gly Val Tyr Gly Gly Ser Gly Ala Gly Ala Ala Gly Ala
65                  70                  75                  80

Gly Ala Gly Ala Ala Val Gly Tyr Gly Gly Tyr Gly Gly Ala
            85                  90                  95

Gly Ala Gly Ala Gly Ala Ala Ala Ala Gly Ala Gly Ala Gly Ala
            100                 105                 110

Gly Gly Gly Tyr Gly Gly Tyr Ser Gly Gly Ala Gly Ala Gly Ala Gly
        115                 120                 125

Ala Ala Ala Ala Ala Gly Ala Gly Ala Gly Gly Ser Tyr Gly Gly Gly
        130                 135                 140

Phe Gly Gly Tyr Ser Val Gly Ala Gly Ser Gly Ala Gly Val Val Ser
145                 150                 155                 160

Thr Val Ser Ser Thr Thr Thr Arg Leu Ser Ser Ala Glu Ala Ser Ser
            165                 170                 175

```
Arg Ile Ser Thr Ala Ala Ser Ser Leu Val Ala Gly Gly Val Val Asn
            180                 185                 190

Thr Ser Val Leu Pro Ser Val Ile Ser Asn Leu Tyr Ser Gln Val Ser
        195                 200                 205

Ala Ser Ser Pro Gly Ala Ser Ser Ser Glu Val Leu Val Gln Val Leu
    210                 215                 220

Leu Glu Ile Ile Ser Ser Leu Ile His Ile Leu Gly Ser Ser Ser Val
225                 230                 235                 240

Gly Gln Ile Asn Leu Gly Ser Val Ala Ser Ser Ala Ala Ala Val Gly
                245                 250                 255

Gln Ser Leu Gln Ala Val Met Gly
            260

<210> SEQ ID NO 20
<211> LENGTH: 216
<212> TYPE: PRT
<213> ORGANISM: Caerostris darwini

<400> SEQUENCE: 20

Ser Arg Ala Pro Ser Ala Tyr Ser Gly Gly Ser Met Ala Ser Leu Pro
1               5                   10                  15

Ser Gln Gly Ser Ser Ala Phe Ser Gly Gly Ser Val Ala Ser Leu Gln
            20                  25                  30

Ser Gln Gly Ser Ser Ala Tyr Ser Gly Ala Ser Ala Ala Ser Leu Gln
        35                  40                  45

Ser Arg Ala Ser Ser Ala Tyr Ser Gly Gly Ser Ala Arg Ser Leu Gln
    50                  55                  60

Ser Gln Ala Ser Ser Ala Phe Ser Gly Gly Ser Gly Thr Gln Tyr Gly
65                  70                  75                  80

Ser Ser Gln Ser Ser Ser Met Ser Ser Ser Ala Ala Leu Gly Pro Ile
                85                  90                  95

Ile Ala Pro Val Ser Val Pro Ser Tyr Val Gln Pro Thr Ser Arg Pro
            100                 105                 110

Ala Ser Val Gly Ile Ser Ser Gly Ser Ser Leu Ala Val Ser Ser Gln
        115                 120                 125

Gln Leu Met Ser Pro Ala Ala Ala Gln Arg Ile Ser Ala Leu Ser Asn
    130                 135                 140

Ser Leu Ala Ser Ala Ile Ala Gly Gly Arg Ile Asn Tyr Gly Ala Leu
145                 150                 155                 160

Ser Asn Ser Leu Ala Ala Ala Ser Arg Gln Ile Gln Ser Gly Ser Gly
                165                 170                 175

Met Ser Lys Thr Glu Ala Ile Val Glu Thr Leu Leu Glu Thr Leu Ala
            180                 185                 190

Ala Leu Leu Glu Thr Ile Ser Gly Ser Ser Gly Gly Gly Gln Thr Ala
        195                 200                 205

Gln Met Leu Leu Gln Ala Leu Ala
    210                 215

<210> SEQ ID NO 21
<211> LENGTH: 594
<212> TYPE: PRT
<213> ORGANISM: Caerostris darwini

<400> SEQUENCE: 21

Val Cys Ala Asn Val Ile Val Ser Ala Cys Val Lys Ala Met Leu Ser
1               5                   10                  15
```

```
Ser Gly Val Ser Val Ser Asp Ser Asn Ser Gln Gln Ile Ala Ser Gln
            20                  25                  30

Leu Ser Ser Thr Ile Val Asp Ala Val Cys Gly Ala Ala Gly Arg Ala
        35                  40                  45

Gly Met Arg Ile Pro Asp Ser Val Val Gln Ser Asp Lys Asn Leu Val
    50                  55                  60

Ser Gln Thr Ile Thr Ser Ile Ser Ser Thr Ser Ser Ala Thr Thr Thr
65                  70                  75                  80

Thr Thr Thr Ser Val Gln Ser Thr Asp Ser Ser Ser Ser Phe Ser
                85                  90                  95

Gly Leu Asp Ser Thr Gly Gly Tyr Thr Gly Ile Pro Ser Gly Gly Tyr
            100                 105                 110

Pro Gly Gly Pro Asp Tyr Gly Gln Gly Ser Asp Asn Val Gln Arg Gln
        115                 120                 125

Leu Val Gln Thr Leu Thr Glu Ala Leu Gln Gly Thr Gln Ser Met Ser
    130                 135                 140

Leu Val Ser Arg Ala Lys Leu Phe Ser Ile Asn Ser Ser Tyr Arg Thr
145                 150                 155                 160

Asp Phe Ala Arg Leu Val Ser Gly Pro Met Asn Leu Gly Gly Ser Ala
            165                 170                 175

Gln Ser Glu Leu Leu Val Ser Leu Ala Gly Ile Ser Pro Asn Ser Asp
        180                 185                 190

Ala Arg Val Cys Ala Asn Val Ile Val Ser Ala Cys Val Lys Ala Met
    195                 200                 205

Leu Ser Ser Gly Val Ser Val Ser Asp Ser Asn Ser Gln Gln Ile Ala
            210                 215                 220

Ser Gln Leu Ser Ser Thr Ile Val Asp Ala Val Cys Gly Ala Ala Gly
225                 230                 235                 240

Arg Ala Gly Met Arg Ile Pro Asp Ser Val Val Gln Ser Asp Lys Asn
            245                 250                 255

Leu Val Ser Gln Thr Ile Ser Ser Ile Ser Ser Thr Ser Ser Ala Thr
        260                 265                 270

Thr Thr Thr Thr Thr Ser Val Gln Ser Thr Asp Ser Ser Ser Ser Ser
    275                 280                 285

Phe Ser Gly Leu Asp Ser Thr Gly Gly Tyr Thr Gly Ile Pro Ser Gly
290                 295                 300

Gly Tyr Pro Gly Gly Pro Asp Tyr Gly Gln Gly Ser Asp Asn Val Gln
305                 310                 315                 320

Arg Gln Leu Val Gln Thr Leu Thr Glu Ala Leu Gln Gly Thr Gln Ser
            325                 330                 335

Met Lys Leu Val Phe Gly Ala Gln Leu Phe Pro Asn Asn Ser Phe Arg
        340                 345                 350

Thr Glu Phe Ala Arg Leu Val Ser Gly Ser Met Asn Leu Gly Gly Ser
    355                 360                 365

Ala Ser Ser Glu Leu Leu Val Ser Leu Ala Gly Ile Ser Pro Thr Ser
        370                 375                 380

Asp Ala Arg Val Ser Phe Lys Val Leu Val Ser Ala Cys Val Gly Ala
385                 390                 395                 400

Met Leu Ser Ser Gly Val Ser Val Ser Asp Ser Asn Cys Gln Gln Ile
            405                 410                 415

Ala Ser Gln Leu Ser Ser Thr Ile Val Asp Ala Val Cys Gly Ala Ala
        420                 425                 430
```

```
Gly Arg Ala Gly Val Arg Ile Pro Asp Ser Val Val Gln Ser Asp Lys
            435                 440                 445

Asn Leu Val Ser Gln Thr Ile Ser Ser Thr Ser Ala Thr Thr Thr
450                 455                 460

Ser Ala Thr Ser Val Gln Ser Thr Asp Leu Ser Ser Ser Ser Phe Leu
465                 470                 475                 480

Gly Gln Asp Ser Thr Gly Val Ser Ser Thr Ser Val Ser Ser Ile
                485                 490                 495

Ile Asn Ser Pro Asn Gly Leu Lys Ser Pro Gln Ala Asn Ala Arg Ile
                500                 505                 510

Asn Ser Leu Ala Ser Leu Phe Asn Asn Ala Ile Gly Ser Asn Gly Val
            515                 520                 525

Gln Ile Asp Ala Val Ser Gln Gly Leu Ala Gly Ile Met Ser Asn Leu
530                 535                 540

Lys Arg Ser Gly Met Ser Pro Thr Gln Ala Gln Val Glu Ala Leu Val
545                 550                 555                 560

Glu Met Asn Cys Ala Leu Leu Lys Ile Val Val Ala Ser Gln Gly Gly
                565                 570                 575

Ser Pro Asn Ser Val Ser Ser Ser Met Thr Ser Leu Leu Ser Val
                580                 585                 590

Met Leu

<210> SEQ ID NO 22
<211> LENGTH: 663
<212> TYPE: PRT
<213> ORGANISM: Caerostris darwini

<400> SEQUENCE: 22

Lys Phe Ile Val Pro Asn Gly Ala Phe Ser Thr Pro Gly Ser Ile Pro
1               5                   10                  15

Gly Pro Asp Gly Lys Pro Ile His Val Gln Pro Ala Gly Pro Gly Thr
                20                  25                  30

Thr Pro Gly Ala Ile Thr Asp Ser Asp Gly Asp Val Val Gln Ile Phe
            35                  40                  45

Leu Pro Ser Thr Pro Ala Pro Lys Pro Val Asn Pro Thr Thr Pro Thr
50                  55                  60

Ala Ile Thr Gly Pro Lys Gly Asn Pro Ile Val Ile Tyr Pro Ala Gly
65                  70                  75                  80

Pro Gly Thr Thr Pro Gly Thr Val Thr Gly Pro Asp Gly Lys Pro Thr
                85                  90                  95

Gln Phe Ile Val Pro Leu Gly Ala Phe Ser Thr Pro Gly Ser Ile Pro
                100                 105                 110

Gly Pro Asp Gly Lys Pro Ile Pro Val Glu Pro Ala Gly Pro Gly Thr
            115                 120                 125

Thr Pro Gly Thr Leu Thr Asp Pro Asp Gly Arg Val Asn Arg Ile Tyr
130                 135                 140

Leu Pro Thr Thr Pro Ala Pro Pro Ser Tyr Gln Pro Gln Val Pro Leu
145                 150                 155                 160

Thr Thr Thr Pro Ile Pro Gly Pro Gly Pro Gln Pro Ile Gln Ile Ile
                165                 170                 175

Pro Ala Gly Pro Gly Thr Thr Pro Gly Thr Val Thr Gly Pro Asp Gly
            180                 185                 190

Arg Pro Thr Gln Phe Ile Val Pro Gln Gly Ala Phe Ser Thr Pro Gly
        195                 200                 205
```

```
Thr Ile Pro Gly Ala Asp Gly Lys Pro Ile Pro Val Glu Pro Ala Gly
    210                 215                 220
Pro Gly Met Thr Pro Gly Ala Gln Thr Gly Pro Asp Gly Lys Ile Thr
225                 230                 235                 240
Arg Ile Val Leu Pro Thr Thr Thr Pro Leu Pro Pro Pro Gly Pro
                245                 250                 255
Leu Asn Pro Asp Gly Leu Pro Val Ala Pro Phe Gly Pro Gly Asn Ser
        260                 265                 270
Pro Asn Tyr Gln Ser Pro Gly Gly Tyr Pro Gly Phe Gln Phe Pro Gly
            275                 280                 285
Tyr Pro Gly Ala Pro Gly Ser Asp Gly Pro Thr Arg Tyr Ile Asn Ser
    290                 295                 300
Asn Glu Leu Pro Ser Gly Glu Thr Pro Asp Gly Tyr Leu Asn Val Asp
305                 310                 315                 320
Ser Leu Pro Asp Phe Val Thr Pro Gly Phe Pro Gln Ser Pro Leu Gly
                325                 330                 335
Tyr Leu Asp Phe Ser Gln Leu Pro Asp Asn Tyr Ser Pro Asp Phe Pro
        340                 345                 350
Gly Gln Leu Val Phe Pro Gly Tyr Pro Asn Ser Pro Gly Asn Gly Arg
            355                 360                 365
Asn Thr Pro Gly Gly Phe Leu Ser Phe Pro Asp Phe Pro Lys Asp Ile
    370                 375                 380
Thr Asn Lys Leu Asn Ser Pro Phe Ser Phe Pro Gln Ile Ile Gln Ala
385                 390                 395                 400
Leu Gln Pro Leu Phe Pro Gly Asn Thr Ile Asn Met Gly Ala Ile Pro
                405                 410                 415
Lys Asp Gln Leu Gln Asn Ile Pro Gly Leu Asp Gly Asp Tyr Asn Asn
        420                 425                 430
Leu Gln Ile Pro Asp Met Gly Asp Ser Ser His Pro Thr Gly Gly Val
            435                 440                 445
Phe Tyr Leu Pro Glu Leu Ile Arg Leu Ile Ser Tyr Leu Pro Val Gly
    450                 455                 460
Ser Phe Pro Gly Arg Gly Pro Gly Thr Met Asn Pro Asp Gly Thr Tyr
465                 470                 475                 480
Ser Asp Pro Phe Asp Phe Pro Gly Leu Asn Gly Ala Pro Gly Tyr Ile
                485                 490                 495
Cys Asp Tyr Pro Asp Asn Gly Asp Ala Thr Pro Asp Leu Gly Gln Glu
        500                 505                 510
Val Gln Gly Thr Asn Gln Gly Pro Val Gly Asp Val Glu Asp Ala Ala
            515                 520                 525
Pro Gly Ser Asp Asp Asp Leu Gly Ala Pro Ala Pro Gln Leu Glu Ser
    530                 535                 540
Asp Glu Ser Asp Cys Asp Asp Val Phe Gly Thr Phe Asn Lys Ala
545                 550                 555                 560
Arg Ser Ser Leu Leu Asp Val Ala Ser Ser Thr Gly Val Gln Thr Ile
                565                 570                 575
Ser Asp Leu Met Gln Ala Leu Ile Ser Gly Ile Asn Pro Tyr Glu Asn
        580                 585                 590
Thr Val Asp Tyr Asn Asp Phe Phe Asn Glu Leu Ser Ser Leu Phe Ser
            595                 600                 605
Gln Val Arg Ala Gly Ser Asp Ser Gln Gly Pro Asn Lys Glu Phe Ile
    610                 615                 620
Lys Ile Leu Phe Glu Ala Leu Val Ala Ser Leu Glu Ala Leu Asn Ala
```

```
                   625                 630                 635                 640
Ala Lys Val Asn Gly Phe Arg Asp Val Ser Val Pro Ser Ala Leu Pro
                                   645                 650                 655

Val Tyr Thr Ser Phe Leu Ser
                660

<210> SEQ ID NO 23
<211> LENGTH: 230
<212> TYPE: PRT
<213> ORGANISM: Caerostris darwini

<400> SEQUENCE: 23

Met Ser Tyr Leu Thr Arg Leu Ala Leu Ala Leu Leu Ala Val Leu Ser
1               5                  10                  15

Thr Gln Ala Ile Phe Ala Asn Gly Gln Ile Thr Pro Trp Ser Asn Thr
            20                  25                  30

Arg Leu Ala Glu Ala Phe Ile Asn Ser Phe Met Ser Lys Val Gly Tyr
        35                  40                  45

Ser Gly Ala Phe Thr Ala Glu Gln Met Asp Asp Met Ser Thr Val Ser
    50                  55                  60

Asp Thr Ile Met Thr Ala Met Asp Lys Met Ala Ser Ser Asn Lys Ser
65                  70                  75                  80

Ser Lys Ser Lys Leu Gln Ala Leu Asn Met Ala Phe Ala Ser Thr Met
                85                  90                  95

Ala Glu Ile Ala Ala Thr Glu Glu Gly Gly Gln Ser Met Ala Val Lys
            100                 105                 110

Thr Asn Ala Ile Thr Asp Ala Leu Ser Ala Ala Phe Leu Glu Thr Thr
        115                 120                 125

Gly Gln Val Asn Tyr Gln Phe Ile Asn Glu Ile Lys Ser Leu Val Tyr
    130                 135                 140

Met Leu Ala Gln Gln Ser Met Asn Asp Val Tyr Ala Ser Ala Gly Thr
145                 150                 155                 160

Ala Ser Gly Gly Gly Tyr Gly Pro Gly Pro Gln Gly Pro Ser Gly Pro
                165                 170                 175

Gly Pro Tyr Gly Pro Arg Gly Val Ser Val Val Ser Thr Ser Val Ser
            180                 185                 190

Gly Pro Gly Pro Gln Gly Pro Ser Gly Pro Gly Pro Gln Gly Pro Tyr
        195                 200                 205

Gly Pro Gly Pro Gln Gly Pro Gly Pro Gln Gly Pro Gly Pro Gln Gly
    210                 215                 220

Pro Gly Pro Gln Gly Pro
225                 230

<210> SEQ ID NO 24
<211> LENGTH: 315
<212> TYPE: PRT
<213> ORGANISM: Caerostris darwini

<400> SEQUENCE: 24

Met Tyr Ser Ser Thr Arg Leu Ala Leu Thr Leu Leu Ala Val Leu Cys
1               5                  10                  15

Thr Gln Ala Ile Phe Thr Ala Ala Gln Ala Pro Ser Pro Trp Glu Ser
            20                  25                  30

Thr Ala Leu Ala Glu Arg Phe Met Ala Ser Phe Leu Ala Ala Thr Gly
        35                  40                  45

Gln Ser Gly Ala Phe Thr Ala Glu Gln Leu Asp Asp Met Ser Thr Ile
```

```
           50                  55                  60
Gly Asp Thr Leu Ser Ser Ala Met Asp Lys Met Ala Arg Ser Asn Lys
65                  70                  75                  80

Ser Ser Lys Ser Lys Leu Gln Ala Leu Asn Met Ala Phe Ala Ser Ser
                85                  90                  95

Met Ala Glu Ile Ala Ala Val Glu Gln Gly Gly Gln Ser Ile Ala Val
            100                 105                 110

Lys Thr Asn Ala Ile Glu Asn Ala Leu Ile Ser Ala Phe Met Gln Thr
        115                 120                 125

Thr Gly Ala Val Asn Tyr Gln Phe Val Ser Glu Ile Arg Asn Leu Val
    130                 135                 140

Asn Met Met Ala Gln Ala Ser Ala Asn Glu Val Ser Tyr Ala Ser Ala
145                 150                 155                 160

Gly Gly Ser Ala Ala Ser Ala Ser Gly Gly Tyr Gly Pro Ser Ser
                165                 170                 175

Gln Gly Pro Ser Gly Pro Gly Gly Tyr Ser Ser Ser Val Ser Val Ser
            180                 185                 190

Gly Val Tyr Gly Pro Gly Pro Gln Gly Pro Ala Pro Gln Gly Pro Ser
        195                 200                 205

Gly Pro Thr Pro Gln Gly Pro Gln Gly Ile Ser Ser Ser Val Ser Val
    210                 215                 220

Ser Gly Val Tyr Gly Pro Gly Pro Gln Gly Pro Ala Pro Gln Gly Pro
225                 230                 235                 240

Ser Gly Pro Thr Pro Gln Gly Pro Gln Gly Thr Tyr Ser Ser Val Ser
                245                 250                 255

Val Ser Gly Ala Tyr Gly Pro Gly Pro Gln Gly Pro Ala Gly Gln Gly
            260                 265                 270

Pro Ser Gly Pro Gly Pro Gln Gly Pro Gly Gly Ala Ala Ala Ala Ala
        275                 280                 285

Ala Ala Ala Ser Gly Tyr Gly Pro Gly Gly Gln Gly Pro Ser Gly Ser
    290                 295                 300

Gly Gly Gln Gly Pro Ser Gly Pro Gly Gly Ser
305                 310                 315

<210> SEQ ID NO 25
<211> LENGTH: 365
<212> TYPE: PRT
<213> ORGANISM: Caerostris darwini

<400> SEQUENCE: 25

Met Thr Trp Thr Ser Arg Leu Ala Leu Ser Leu Leu Val Ala Ile Cys
1               5                   10                  15

Thr Gln Ser Met Phe Ala Leu Gly Gln Asp Asn Thr Pro Trp Ser Ser
            20                  25                  30

Thr Gly Thr Ala Glu Ser Phe Met Ser Ser Phe Met Ser Ala Ala Gly
        35                  40                  45

Asn Ser Gly Ala Phe Thr Ala Asp Gln Leu Asp Asp Met Asn Thr Ile
    50                  55                  60

Thr Asp Thr Ile Arg Ser Ala Met Asp Lys Met Ala Arg Ser Asn Lys
65                  70                  75                  80

Ser Ser Lys Ser Lys Leu Gln Ala Leu Asn Met Ala Phe Ser Ser Ala
                85                  90                  95

Met Ala Glu Ile Ala Ile Asp Glu Gly Gly Gln Ser Val Gly Tyr Lys
            100                 105                 110
```

```
Thr Asp Ala Ile Ala Asp Ala Leu Ser Gln Ala Phe Leu Gln Thr Thr
        115                 120                 125
Gly Val Val Asn Gly Ala Phe Ile Asn Glu Ile Arg Ser Leu Ile Ser
    130                 135                 140
Met Phe Ala Gln Asn Ser Ala Asn Ala Ile Gly Ser Gly Ser Ser
145                 150                 155                 160
Ala Ser Val Ser Val Ala Ala Ser Ala Gly Gly Tyr Gly Gln
                165                 170                 175
Gly Ser Tyr Gly Pro Gly Pro Gln Gly Pro Ser Gly Pro Gly Pro Gln
            180                 185                 190
Gly Ala Gly Ala Ser Ser Ala Ser Ala Val Ser Ala Ala Ser Gly Pro
        195                 200                 205
Gly Gly Tyr Ala Pro Gly Pro Gln Gly Pro Ser Gly Pro Gln Gly Pro
    210                 215                 220
Gly Gln Ser Ser Tyr Gln Tyr Ser Val Ser Ile Ser Thr Gln Gly Gly
225                 230                 235                 240
Ser Gln Gly Gly Tyr Gly Gly Gln Gln Gly Ala Gly Gln Gly Gly
                245                 250                 255
Tyr Gly Gly Gly Leu Gly Gly Gln Gly Ala Gly Ala Ala Ala Ala
            260                 265                 270
Ala Ala Ala Gly Gly Ala Gly Gly Leu Gly Gly Gln Gly Gly Gln Gly
        275                 280                 285
Gly Gly Gln Gly Ala Gly Ala Ala Gly Gln Gly Gly Tyr Gly Ser Gly
    290                 295                 300
Leu Gly Gly Gln Gly Gly Ala Ala Ala Ala Ala Ala Ala Gly
305                 310                 315                 320
Gly Ala Gly Gly Leu Gly Gly Gln Gly Gly Gln Gly Gly Gln Gly
                325                 330                 335
Ala Gly Gly Ala Gly Gln Gly Gly Tyr Gly Ser Gly Leu Gly Gly Gln
            340                 345                 350
Gly Gly Gly Ala Ala Ala Ala Ala Ala Gly Gly
        355                 360                 365

<210> SEQ ID NO 26
<211> LENGTH: 367
<212> TYPE: PRT
<213> ORGANISM: Caerostris darwini

<400> SEQUENCE: 26

Met Ser Trp Thr Ser Arg His Ala Leu Phe Tyr Leu Val Ile Cys
1               5                   10                  15
Thr Gln Ser Val Leu Ala Leu Gly Arg Asn Asn Asn Pro Trp Ser Asn
            20                  25                  30
Pro Ser Ser Ala Glu Ser Phe Met Asn Tyr Phe Met Asp Gly Val Thr
        35                  40                  45
Asn Ser Gly Ser Phe Thr Pro Asp Gln Leu Asp Asp Met Cys Val Ile
    50                  55                  60
Cys Asp Thr Ile Lys Ala Thr Thr Asp Arg Met Ser Arg Ser Asn Lys
65                  70                  75                  80
Asn Thr Glu Ser Ser Leu Gln Ala Leu Asn Ile Ala Phe Ala Ser Ala
                85                  90                  95
Val Ala Glu Ile Ala Ala Ala Glu Gly Thr Glu Asn Ile Gly Met Lys
            100                 105                 110
Thr Gly Ala Ile Thr Asp Ala Leu Ser Ser Ala Phe Met Gln Thr Thr
        115                 120                 125
```

Gly Gln Val Asn Thr Glu Phe Val Asn Glu Ile Arg Ser Leu Ile Asn
    130                 135                 140

Met Phe Ser Gln Val Ser Arg Asn Asn Ile Ser Gln Gly Gly Leu Gly
145                 150                 155                 160

Gly Thr Gly Asp Val Gly Gly Ala Gly Gly Arg Gly Gly Leu Ser Gly
                165                 170                 175

Ala Gly Gly Leu Ser Gly Pro Ser Gly Leu Gly Gly Thr Gly Gly Arg
            180                 185                 190

Gly Gly Phe Ala Gly Ser Gly Gly Leu Gly Ala Ser Ala Ser Ser
        195                 200                 205

Ala Ser Ser Gly Gly Pro Gly Gly Ser Gly Gln Gly Tyr Gly Gly
    210                 215                 220

Ser Leu Gly Gly Pro Gly Gly Phe Gly Arg Ser Gly Gly Gly Leu Gly
225                 230                 235                 240

Gly Gly Asp Ser Ala Ala Ser Thr Ser Ser Ile Gly Ser Gly Gly Pro
                245                 250                 255

Gly Gly Ser Gly Gln Gly Gly Tyr Gly Gly Ser Leu Gly Gly Pro Gly
            260                 265                 270

Gly Phe Gly Arg Ser Gly Gly Gly Leu Gly Gly Gly Asp Ser Ala Ala
        275                 280                 285

Ser Ala Ser Ser Val Gly Ser Gly Gly Pro Asp Gly Ser Gly Pro Gly
    290                 295                 300

Gly Tyr Arg Gly Asn Ile Asp Gly Pro Gly Gly Phe Gly Arg Ser Gly
305                 310                 315                 320

Gly Gly Leu Gly Gly Gly Asp Ser Ala Ala Ser Ala Ser Ser Val Gly
                325                 330                 335

Ser Gly Gly Pro Asp Gly Ser Gly Pro Gly Gly Tyr Gly Gly Ser Leu
            340                 345                 350

Gly Gly Pro Gly Gly Phe Gly Arg Ser Gly Gly Gly Leu Gly Gly
        355                 360                 365

<210> SEQ ID NO 27
<211> LENGTH: 383
<212> TYPE: PRT
<213> ORGANISM: Caerostris darwini

<400> SEQUENCE: 27

Met Ile Trp Ile Ala Arg Leu Ala Leu Leu Val Ala Val Ala Phe Ser
1               5                   10                  15

Thr Gln Ser Gln Leu Ala Leu Gly Gln Asp Asn Thr Pro Trp Ser Ser
            20                  25                  30

Thr Ser Ser Ala Glu Arg Phe Met Glu Ala Phe Ile Gly Gly Ala Gln
        35                  40                  45

Asn Thr Gly Val Phe Thr Asp Gly Gln Ile Ser Asp Met Lys Asp Ile
    50                  55                  60

Ile Asp Thr Ile Lys Ala Ala Met Glu Lys Met Lys Asn Lys Asn Lys
65                  70                  75                  80

Asn Ser Lys Ser Val Leu Gln Ala Leu Asn Met Ala Phe Ala Ser Ser
                85                  90                  95

Val Ser Glu Ile Ala Val Thr Glu Gly Ser Gln Ser Ile Glu Ala Lys
            100                 105                 110

Thr Asn Ala Ile Ser Asp Ala Leu Ala Ser Ala Phe Met Gln Thr Thr
        115                 120                 125

Gly Ser Val Asn Gln Gly Phe Ile Asn Glu Met Lys Thr Leu Val Ser

```
            130                 135                 140
Met Phe Ala Gln Thr Ser Phe Asn Asp Val Ser Tyr Ser Asp Ser Ser
145                 150                 155                 160

Ala Ser Ser Ser Gly Gly Tyr Gly Ser Pro Gly Gly Tyr Asn Ser
                165                 170                 175

Gly Gly Pro Gly Ala Ala Ser Ala Val Ser Thr Ser Ser Ala Ser Gly
                180                 185                 190

Ala Ala Glu Pro Ile Phe Tyr Gly Gln Gly Pro Ser Ala Tyr Gln Tyr
            195                 200                 205

Ser Val Ser Ile Ser Thr Gln Ser Gly Gly Gln Gly Gly Tyr Glu Gly
            210                 215                 220

Ile Gly Gly Val Gly Thr Ala Ser Ala Ala Ser Ala Gly Gly Gly Thr
225                 230                 235                 240

Gly Ala Gly Glu Ser Gly Gln Gly Gly Tyr Gly Gly Ile Gly Thr Gly
                245                 250                 255

Ser Ser Ser Ala Ala Ala Ala Gly Ala Gly Gly Ala Gly Gly Phe Gly
                260                 265                 270

Pro Gly Gly Tyr Gly Met Gly Gly Leu Gly Gly Ala Gly Ser Ala Ala
            275                 280                 285

Ala Ala Ala Gly Gly Ala Gly Gly Ile Gly Pro Gly Gly Tyr Gly Gly
290                 295                 300

Asn Gly Gly Gln Gly Gly Val Gly Ser Ala Ser Ala Ala Ala Ala Gly
305                 310                 315                 320

Ala Gly Gly Thr Gly Gly Phe Gly Pro Gly Gly Tyr Gly Gly Gly Gly
                325                 330                 335

Leu Gly Gly Glu Gly Ala Ala Ser Ala Ala Ala Gly Ala Gly Gly Gly
                340                 345                 350

Ala Gly Gly Phe Gly His Ala Ala Gly Ala Gly Gly Pro Asp Gly Tyr
            355                 360                 365

Gly Ser Gly Gly Tyr Gly Gly Arg Gly Gly Gln Gly Gly Ala Gly
    370                 375                 380

<210> SEQ ID NO 28
<211> LENGTH: 400
<212> TYPE: PRT
<213> ORGANISM: Caerostris darwini

<400> SEQUENCE: 28

Met Ser Trp Leu Pro Ala Leu Ser Leu Leu Val Leu Leu Val Pro
1               5                   10                  15

Asn Thr Asn Ala Ile Ser Ala Ser Lys Ala Ser Phe Gln Asp Glu Gly
                20                  25                  30

Thr Thr Ile Tyr Leu Leu Arg Ser Ile Leu Glu Tyr Leu Arg Glu Cys
            35                  40                  45

Asp Val Leu Lys Ile Asp Gln Glu Ser Asp Ala Val Asn Ala Leu Phe
    50                  55                  60

Glu Val Ser Leu Leu Phe Gln Asn Asn Val Lys Met Ser Lys Arg Lys
65                  70                  75                  80

Gln Ala Ile Ala Ser Lys Leu Ala Gly Ile Ile Met Glu Gly Leu Glu
                85                  90                  95

Gly Ser Asn Glu Thr Ala Tyr Lys Leu Asp Cys Ala Thr Asn Ala Met
            100                 105                 110

Ile Ala Ala Met Glu Asn Thr Ser Gly Thr Val Asp Met Ser Phe Ile
            115                 120                 125
```

-continued

```
Asp Ser Val Lys Glu Leu Ala Val Val Met Tyr Asn Asn Asp Ile Glu
    130                 135                 140

Ala Lys Leu Glu Glu Leu Glu Glu Gln Glu Glu Leu Tyr Gln Glu
145                 150                 155                 160

Gln Leu Leu Ser Ser Val Ile Pro Glu Ser Gln Ile Ser Thr Asp Gln
                165                 170                 175

Ser Asp Tyr Gly Ser Ile Gln Ile Gln Asn Gln Leu Val Asp Gln Gly
            180                 185                 190

Val Ser Ser Ile Thr Thr Ser Asn Glu Asn Gln Ile Gln Thr Gln Gln
        195                 200                 205

Ser Val Thr Asn Gln Ile Gln Leu Thr Ser Thr Ala Glu Thr Gln Ser
    210                 215                 220

Gln Gln Ser Ala Gly Thr Thr Ala Ser Gln Gln Ser Tyr Ile Asp Gly
225                 230                 235                 240

Gln Gln Ser Tyr Ile Ser Gln Gln Ser Ala Glu Ser Gln Gln Gln
                245                 250                 255

Tyr Ala Asn Thr Gln Gln Gln Ser Val Glu Ser Gln Gln Gln Ser Ala
            260                 265                 270

Glu Ser Gln Gln Gln Tyr Ala Asn Ser Gln Gln Ala Thr Gly Ser
        275                 280                 285

Thr Gln Asn Tyr Ala Thr Ser Gln Gln Asn Ile Gln Ser Ser Asn Ser
    290                 295                 300

Tyr Glu Asp Gln Ser Ser Ile Ser Gln Ala Gln Val Gln Ser Ser
305                 310                 315                 320

Tyr Ser Gln Asn Gln Tyr Ser Ala Ser His Gln Gln Ala Thr Asp Thr
                325                 330                 335

Leu Gln Gln Thr Ile Glu Ser Gln Pro Gln Tyr Thr Ser Ser Gln Gln
            340                 345                 350

Gln Ile Gln Gln Ser Ser Asn Glu Tyr Ser Asp Gln Ser Ser Leu Thr
        355                 360                 365

Gln Tyr Gln Val Asp Ser Ser Ala Ser Ile Tyr Phe Gln Thr Asp
    370                 375                 380

Val Val His Asn Arg Val Ala Gln Ser Leu Leu Ser Ser Ser Val Leu
385                 390                 395                 400
```

<210> SEQ ID NO 29
<211> LENGTH: 584
<212> TYPE: PRT
<213> ORGANISM: Caerostris darwini

<400> SEQUENCE: 29

```
Met Tyr Ser Ser Thr Arg Leu Ala Leu Thr Leu Leu Ala Val Leu Cys
1               5                   10                  15

Thr Gln Ala Ile Phe Thr Ala Ala Gln Ala Pro Ser Pro Trp Glu Ser
                20                  25                  30

Thr Ala Leu Ala Glu Arg Phe Met Ala Ser Phe Leu Ala Ala Thr Gly
            35                  40                  45

Gln Ser Gly Ala Phe Thr Ala Glu Gln Leu Asp Asp Met Ser Thr Ile
        50                  55                  60

Gly Asp Thr Leu Ser Ser Ala Met Asp Lys Met Ala Arg Ser Asn Lys
65                  70                  75                  80

Ser Ser Lys Ser Lys Leu Gln Ala Leu Asn Met Ala Phe Ala Ser Ser
                85                  90                  95

Met Ala Glu Ile Ala Ala Val Glu Gln Gly Gly Gln Ser Ile Ala Val
            100                 105                 110
```

```
Lys Thr Asn Ala Ile Glu Asn Ala Leu Ile Ser Ala Phe Met Gln Thr
        115                 120                 125

Thr Gly Ala Val Asn Tyr Gln Phe Val Ser Glu Ile Arg Asn Leu Val
    130                 135                 140

Asn Met Met Ala Gln Ala Ser Ala Asn Glu Val Ser Tyr Ala Ser Ala
145                 150                 155                 160

Gly Gly Ser Ala Ala Ser Ala Ser Gly Gly Tyr Gly Pro Ser Ser
            165                 170                 175

Gln Gly Pro Ser Gly Pro Gly Gly Tyr Ser Ser Val Ser Val Ser
            180                 185                 190

Gly Val Tyr Gly Pro Gly Pro Gln Gly Pro Ala Pro Gln Gly Pro Ser
        195                 200                 205

Gly Pro Thr Pro Gln Gly Pro Gln Gly Ile Ser Ser Val Ser Val
    210                 215                 220

Ser Gly Val Tyr Gly Pro Gly Pro Gln Gly Pro Ala Pro Gln Gly Pro
225                 230                 235                 240

Ser Gly Pro Thr Pro Gln Gly Pro Gln Gly Thr Tyr Ser Ser Val Ser
            245                 250                 255

Val Ser Gly Ala Tyr Gly Pro Gly Pro Gln Gly Pro Ala Gly Gln Gly
        260                 265                 270

Pro Ser Gly Pro Gly Pro Gln Gly Pro Gly Ala Ala Ala Ala
    275                 280                 285

Ala Ala Ala Ser Gly Tyr Gly Pro Gly Gly Gln Gly Pro Ser Gly Pro
        290                 295                 300

Gly Ser Gln Gly Pro Gly Gln Gly Pro Ser Gly Pro Gly Ser Gln
305                 310                 315                 320

Gly Pro Gly Gly Gln Gly Pro Tyr Gly Pro Gly Ala Ala Ala Ala
            325                 330                 335

Ala Ala Ala Thr Gly Gly Tyr Gly Gln Gly Gly Tyr Gly Ser Gly Gln
            340                 345                 350

Gly Gly Gln Gly Ala Gly Ser Ala Ala Ala Ala Ala Gly Gly
        355                 360                 365

Ala Gly Gly Arg Gly Gly Tyr Gly Gly Gln Gly Gly Gln Gly Ala Gly
    370                 375                 380

Gly Ala Gly Gln Gly Gly Tyr Gly Ser Gly Leu Gly Gly Leu Gly Gly
385                 390                 395                 400

Gly Ala Ala Ala Ala Ala Ala Ala Gly Gly Ala Gly Gly Leu Gly
            405                 410                 415

Gly Gln Gly Gly Gly Gln Gly Ala Gly Gln Gly Gly Tyr Gly Ser Gly
            420                 425                 430

Gln Gly Gly Gln Gly Ala Gly Ser Ala Ala Ala Ala Ala Ala Gly
            435                 440                 445

Gly Ala Gly Gly Arg Gly Gly Leu Gly Gly Gln Gly Ala Gly Gln Gly
    450                 455                 460

Gly Tyr Gly Ser Gly Gln Gly Gly Tyr Gly Pro Gly Gln Ile Pro
465                 470                 475                 480

Ser Ala Ala Ala Ala Ala Ser Arg Leu Ser Ser Pro Ala Val Ala Ser
            485                 490                 495

Arg Val Ser Ser Thr Val Ser Ser Leu Val Ser Ser Gly Pro Thr Ser
            500                 505                 510

Gln Gly Ala Leu Ser Asn Ala Ile Ser Asn Ala Val Ser Gln Ile Ser
            515                 520                 525
```

Ala Ser Asn Pro Gly Leu Ser Gly Cys Asp Val Leu Val Gln Ala Leu
530                 535                 540

Leu Glu Ile Val Ser Ala Leu Val His Ile Leu Gly Ser Ser Ser Val
545                 550                 555                 560

Gly Gln Val Ser Tyr Asn Thr Ala Gly Gln Ser Ala Ala Val Val Ser
            565                 570                 575

Gln Ser Ile Ser Gln Ala Leu Gly
            580

<210> SEQ ID NO 30
<211> LENGTH: 489
<212> TYPE: PRT
<213> ORGANISM: Caerostris darwini

<400> SEQUENCE: 30

Met Ser Tyr Leu Thr Arg Leu Ala Leu Ala Leu Ala Val Leu Ser
1               5                   10                  15

Thr Gln Ala Ile Phe Ala Asn Gly Gln Ile Thr Pro Trp Ser Asn Thr
            20                  25                  30

Arg Leu Ala Glu Ala Phe Ile Asn Ser Phe Met Ser Lys Val Gly Tyr
        35                  40                  45

Ser Gly Ala Phe Thr Ala Glu Gln Met Asp Asp Met Ser Thr Val Ser
    50                  55                  60

Asp Thr Ile Met Thr Ala Met Asp Lys Met Ala Ser Ser Asn Lys Ser
65                  70                  75                  80

Ser Lys Ser Lys Leu Gln Ala Leu Asn Met Ala Phe Ala Ser Thr Met
                85                  90                  95

Ala Glu Ile Ala Ala Thr Glu Glu Gly Gly Gln Ser Met Ala Val Lys
            100                 105                 110

Thr Asn Ala Ile Thr Asp Ala Leu Ser Ala Ala Phe Leu Glu Thr Thr
        115                 120                 125

Gly Gln Val Asn Tyr Gln Phe Ile Asn Glu Ile Lys Ser Leu Val Tyr
    130                 135                 140

Met Leu Ala Gln Gln Ser Met Asn Asp Val Tyr Ala Ser Ala Gly Thr
145                 150                 155                 160

Ala Ser Gly Gly Gly Tyr Gly Pro Gly Pro Gln Gly Pro Ser Gly Pro
                165                 170                 175

Gly Pro Tyr Gly Pro Arg Gly Val Ser Val Ser Thr Ser Val Ser
            180                 185                 190

Gly Pro Gly Pro Gln Gly Pro Ser Gly Pro Gly Pro Gln Gly Pro Tyr
    195                 200                 205

Gly Pro Gly Pro Gln Gly Pro Gly Pro Gln Gly Pro Gly Pro Gln Gly
210                 215                 220

Pro Gly Pro Gln Gly Pro Ser Gly Pro Gly Pro Gln Gly Pro Tyr Gly
225                 230                 235                 240

Pro Gly Ser Val Ser Val Val Ser Gly Ser Val Ser Gly Pro Gly Pro
                245                 250                 255

Gln Gly Ser Ser Gly Pro Gly Pro Gln Gly Pro Tyr Gly Pro Gly Pro
            260                 265                 270

Gln Gly Pro Ala Pro Lys Gly Pro Gly Pro Gln Gly Pro Gly Pro Gln
        275                 280                 285

Gly Ser Gly Pro Gln Gly Pro Ser Gly Pro Gly Pro Gln Gly Pro Tyr
    290                 295                 300

Gly Pro Gly Gly Val Ser Val Val Ser Thr Thr Val Ser Gly Pro Gly
305                 310                 315                 320

-continued

Pro Ser Gly Pro Gly Pro Gln Gly Pro Tyr Gly Pro Ala Pro Gln Gly
              325                 330                 335

Pro Gly Pro Gln Gly Pro Gly Pro Gln Gly Pro Gly Pro Gln Gly Pro
              340                 345                 350

Gly Pro Gln Gly Pro Ser Gly Gln Gly Pro Gln Arg Pro Ser Gly Pro
              355                 360                 365

Arg Pro Gln Gly Pro Tyr Gly Pro Gly Ile Ser Val Val Ser Ala
              370                 375                 380

Thr Val Ser Gly Pro Gly Pro Gln Gly Pro Ser Gly Pro Gly Pro Gln
385                 390                 395                 400

Arg Pro Tyr Gly Pro Gly Pro Glu Gly Pro Gly Pro Gln Gly Ala Gly
              405                 410                 415

Pro Gln Gly Pro Gly Leu Gln Arg Pro Ser Gly Pro Gly Pro Gln Gly
              420                 425                 430

Pro Tyr Gly Pro Gly Pro Arg Gly Pro Ser Ser Thr Pro Glu Ser Ala
              435                 440                 445

Ala Ile Asn Ala Ala Ser Arg Leu Ser Ser Pro Ala Ala Ser Ser Arg
              450                 455                 460

Val Ser Ser Thr Val Ser Gln Leu Val Ser Ser Gly Pro Pro Asn Ser
465                 470                 475                 480

Ala Ala Val Ser Gly Ala Ile Ser Ser
              485

<210> SEQ ID NO 31
<211> LENGTH: 394
<212> TYPE: PRT
<213> ORGANISM: Caerostris darwini

<400> SEQUENCE: 31

Met Ser Tyr Leu Thr Arg Leu Ala Leu Ala Leu Ala Val Leu Ser
1               5                   10                  15

Thr Gln Ala Ile Phe Ala Asn Gly Gln Asn Pro Trp Ser Asn Thr Gly
              20                  25                  30

Leu Ala Glu Ala Phe Ile Asn Ser Phe Met Ser Lys Val Gly Tyr Ser
              35                  40                  45

Gly Ala Phe Thr Ala Asp Gln Met Asp Asp Met Ser Thr Val Ser Asp
          50                  55                  60

Thr Ile Met Ser Ala Met Asp Lys Met Ala Arg Ser Asn Lys Ser Ser
65                  70                  75                  80

Lys Ser Lys Leu Gln Ala Leu Asn Met Ala Phe Ala Ser Thr Met Ala
              85                  90                  95

Glu Ile Ala Ala Thr Glu Glu Gly Gln Ser Met Ser Val Lys Thr
              100                 105                 110

Asn Ala Ile Thr Asp Ala Leu Ser Ala Ala Phe Leu Glu Thr Thr Gly
              115                 120                 125

Gln Val Asn Tyr Gln Phe Ile Asn Glu Ile Lys Ser Leu Val Tyr Met
              130                 135                 140

Leu Ala Gln Gln Ser Met Asn Asp Val Tyr Ala Ser Ala Gly Thr Ala
145                 150                 155                 160

Ser Gly Gly Gly Tyr Gly Pro Gly Pro Gln Gly Pro Ser Ala Pro Gly
              165                 170                 175

Pro Tyr Gly Pro Gly Gly Val Ser Val Ser Ala Ser Val Ser Gly
              180                 185                 190

Pro Gly Pro Gln Gly Pro Ser Gly Pro Gly Pro Gln Gly Pro Tyr Gly

```
              195                 200                 205
Pro Gly Pro Gln Gly Pro Ala Pro Gln Gly Pro Gly Pro Gln Gly Pro
210                 215                 220
Ser Gly Pro Gly Pro Gln Gly Pro Tyr Gly Pro Gly Pro Gln Gly Pro
225                 230                 235                 240
Gly Pro Arg Gly Pro Gly Pro Gln Gly Pro Gly Pro Gln Gly Pro Gly
            245                 250                 255
Pro Gln Gly Pro Ser Gly Pro Gly Pro Gln Gly Pro Tyr Gly Pro Gly
                260                 265                 270
Gly Val Ser Val Val Ser Ala Ser Val Ser Gly Pro Gly Pro Gln Gly
            275                 280                 285
Pro Ser Gly Pro Ala Val Asn Ala Ala Arg Leu Ser Ser Pro Asp
290                 295                 300
Ala Ser Ser Arg Val Ser Thr Val Ser Gln Leu Val Ser Gly Gly
305                 310                 315                 320
Pro Thr Ser Gly Ala Ala Val Ser Asn Ala Leu Ser Ser Leu Val Ser
                325                 330                 335
Gln Val Gly Ala Ser Asn Pro Gly Leu Ser Gly Cys Asp Ile Leu Val
                340                 345                 350
Gln Ala Leu Met Glu Met Leu Ser Ala Leu Val Ser Ile Val Gly Ser
                355                 360                 365
Ser Ser Ile Gly Gln Val Asn Tyr Gly Ala Ser Gly Gln Tyr Thr Gln
            370                 375                 380
Met Ile Gly Gln Ala Ile Ala Gln Ala Phe
385                 390
```

<210> SEQ ID NO 32
<211> LENGTH: 1001
<212> TYPE: PRT
<213> ORGANISM: Caerostris darwini

<400> SEQUENCE: 32

```
Gln Ser Ser Asn Thr Gln Ser Gln Gln Thr Ala Thr Ser Gln Ser Gln
1               5                   10                  15
Gln Ser Ser Phe Ser Gln Ser Ser Gln Gln Ala Tyr Asn Ala Ala Ser
                20                  25                  30
Thr Ala Ala Ser Ser Val Gln Gln Ser Val Thr Asn Thr Phe Asn Ser
                35                  40                  45
Gln Thr Val Gln Asn Ser Val Ala Gln Ser Leu Met Ser Ser Ser Val
50                  55                  60
Leu Asn Thr Ile Ala Ser Gly Gln Thr Ser Ala Thr Gln Ser Asp Phe
65                  70                  75                  80
Ala Ser Val Ile Ser Asn Ala Leu Ala Asn Thr Leu Gly Val Ser Gln
                85                  90                  95
Ser Ser Val Asn Gly Val Val Asn Gln Gln Ile Ser Asn Leu Arg Pro
                100                 105                 110
Gly Thr Ser Ala Ser Thr Phe Ala Gln Thr Val Ser Asn Ile Ile Ser
                115                 120                 125
Ser Leu Leu Pro Gln Ser Asn Ala Ala Val Ala Gly Gln Glu Gln Ser
                130                 135                 140
Val Ser Gln Ser Val Ser Ala Ser Val Val Asn Ala Leu Ala Asn Leu
145                 150                 155                 160
Ile Ser Arg Gln Ser Arg Pro Val Ala Leu Pro Gln Pro Ala Pro Arg
                165                 170                 175
```

```
Pro Ile Pro Ala Pro Arg Pro Gln Pro Ala Pro Arg Pro Leu Pro Ala
                180                 185                 190

Pro Arg Pro Val Ala Pro Val Ile Gln Ala Pro Ala Pro Val Val Ser
            195                 200                 205

Gln Ile Gln Gln Ser Ser Asn Thr Gln Ser Gln Gln Ser Ser Ile Ser
        210                 215                 220

Gln Ser Gln Gln Thr Ala Phe Ala Glu Ser Gln Gln Arg Gly Ile Ser
225                 230                 235                 240

Glu Ser Gln Ile Ser Ser Phe Ser Thr Ser Gln Gln Thr Gly Asn Leu
                245                 250                 255

Tyr Gly Ser Ala Thr Thr Ala Thr Ser Asn Val Val Gln Ala Pro Ala
            260                 265                 270

Val Ile Ser Arg Thr Ala Asn Tyr Phe Asn Ser Glu Leu Ala Arg Asn
        275                 280                 285

Ser Leu Leu Ser Tyr Leu Gln Ser Ser Asp Ile Leu Asn Val Leu Ala
        290                 295                 300

Ser Gly Gln Thr Ser Thr Ser Leu Ser Asp Leu Ser Ser Val Ile Ala
305                 310                 315                 320

Asn Ser Val Ala Lys Val Leu Gly Gly Ser Gln Thr Thr Phe Tyr Asn
                325                 330                 335

Val Ile Asn Gln Gln Leu Ser Ser Val Gly Ser Gly Ser Ser Ala Ala
            340                 345                 350

Ala Leu Ala Gln Ala Val Ala Asp Ser Val Ser Gly Leu Leu Glu Asn
        355                 360                 365

Ser Gly Val Ala Ile Ala Gly Arg Glu Gln Asp Ile Ser Ser Ser Ile
        370                 375                 380

Ser Ser Ser Ile Leu Ser Ala Leu Ala Gln Arg Val Ser Gln Ser Ser
385                 390                 395                 400

Ile Gln Ala Pro Ala Pro Ile Ala Arg Pro Leu Ser Ala Pro Arg Pro
                405                 410                 415

Val Ser Ala Pro Ser Phe Ala Pro Gln Pro Val Val Ser Gln Ser Gln
            420                 425                 430

Gln Ser Phe Ala Ser Gln Ile Asn Ser Gln Gln Ser Ala Ala Ser Gln
        435                 440                 445

Thr Gln Gln Ser Val Ala Gln Ala Gln Gln Ser Ser Val Ala Gln Val
        450                 455                 460

Gln Gln Ser Ser Tyr Gly Gln Gln Ser Thr Tyr Ala Gln Ala Gln
465                 470                 475                 480

Gln Phe Ser Ser Gly Gln Ser Gln Gln Ala Ser Asn Ala Tyr Ser Thr
                485                 490                 495

Ala Ser Val Gly Pro Ser Asn Val Ala Gln Ser Pro Ser Leu Ser Ser
            500                 505                 510

Ser Gly Tyr Phe Asn Ser Gln Ile Val Gln Asn Asn Leu Val Ser Ser
        515                 520                 525

Leu Gln Ser Ser Asn Ala Phe Asn Ser Val Ile Tyr Gly Gln Thr Gly
        530                 535                 540

Ala Ser Leu Ala Asp Val Glu Ser Ala Ile Ala Ser Ser Ile Ser Gln
545                 550                 555                 560

Ser Ile Gly Ile Pro Leu Ser Ser Val Gln Asn Tyr Ile Arg Gln Gln
                565                 570                 575

Leu Ser Gly Leu Gly Ser Gly Val Thr Thr Ser Thr Phe Ala Gln Ala
            580                 585                 590

Val Ala Asn Gly Val Ser Asn Met Ile Gln Asn Ser Gly Val Ala Ser
```

```
                    595                 600                 605
Ala Gly Gln Glu Gln Asn Val Ser Gln Ile Ile Phe Ser Gly Ile Gln
            610                 615                 620
Thr Ala Leu Thr Gly Leu Met Ser Gln Arg Ser Arg Gln Leu Pro Ala
625                 630                 635                 640
Pro Leu Pro Thr Pro Ser Gln Pro Ile Ser Pro Ser Val Tyr Ala Pro
                645                 650                 655
Gln Pro Ala Ile Ser Pro Ile Gln Gln Ser Phe Ala Thr Gln Ala Gln
            660                 665                 670
Ser Gln Arg Ser Ser Val Gly Gln Ser Gln Gln Ser Ser Phe Ala Gln
        675                 680                 685
Ser Gln Gln Ile Ser Ala Gln Ser Gln Gln Ala Lys Ser Gln Gln Ser
    690                 695                 700
Ser Phe Gly Gln Ser Gln Gln Ser Arg Tyr Ala Gln Ala Gln Gln Val
705                 710                 715                 720
Ser Ser Gln Pro Gln Gln Ser Thr Leu Tyr Gly Gln Ser Gln Gln Ser
                725                 730                 735
Ser Asn Leu Tyr Ser Thr Gly Ser Ser Ser Ser Gly Leu Thr Gln
            740                 745                 750
Ser Ser Ser Tyr Phe Asn Pro Glu Ile Val Gln Asn Leu Val Ser
        755                 760                 765
Ser Leu Gln Ser Ser Ala Leu Asn Ser Ile Ala Ser Gly Gln Ile
    770                 775                 780
Ser Ala Ser Thr Ser Asp Ile Ser Ser Val Ile Ala Asn Ala Val Ala
785                 790                 795                 800
Pro Leu Ala Gly Leu Ser Gln Ser Val Val Gln Asn Val Ile Asn Gln
                805                 810                 815
Gln Leu Ser Ser Val Gly Ser Gly Ala Pro Ala Gly Ile Phe Ala Arg
            820                 825                 830
Ala Leu Ala Thr Ser Leu Ser Arg Leu Ile Gln Lys Ser Gly Ile Ala
        835                 840                 845
Ser Ala Gly Glu Glu Ser Gly Ile Ser Gln Met Ile Ser Ser Gly Ile
    850                 855                 860
Glu Ser Ala Leu Ile Lys Leu Val Ser Gln Lys Ser Met Phe Ala Pro
865                 870                 875                 880
Ala Pro Arg Asn Ala Pro Met Pro Ile Ser Gln Pro Ala Pro Leu Pro
                885                 890                 895
Gln Thr Val Pro Ala Tyr Ala Pro Arg Pro Ser Pro Val Tyr Phe Thr
            900                 905                 910
Ala Pro Ser Leu Gln Gln Ser Ser Ile Ser Gln Asn Gln Gln Ser Asn
        915                 920                 925
Asn Ala Tyr Ser Ser Asn Ala Ala Gln Asn Gln Phe Gln Gln Ala
    930                 935                 940
Ser Ser Leu Gln Ser Gln Ala Ser Ser Ala Tyr Ser Gly Gly Thr Ala
945                 950                 955                 960
Ala Thr Leu Gln Ser Gln Gly Ser Ser Ala Tyr Ser Gly Gly Ser Met
                965                 970                 975
Ala Ser Leu Gln Ser Gln Gly Ser Ser Ala Tyr Ser Gly Gly Ser Met
            980                 985                 990
Ala Ser Leu Gln Ser Gln Gly Ser   Ser
        995                 1000

<210> SEQ ID NO 33
```

```
<211> LENGTH: 19
<212> TYPE: DNA
<213> ORGANISM: Artificial Sequence
<220> FEATURE:
<223> OTHER INFORMATION: Illumina TruSeq P5

<400> SEQUENCE: 33
aatgatacgg cgaccaccg                                                19

<210> SEQ ID NO 34
<211> LENGTH: 19
<212> TYPE: DNA
<213> ORGANISM: Artificial Sequence
<220> FEATURE:
<223> OTHER INFORMATION: Illumina TruSeq P5

<400> SEQUENCE: 34
cggtggtcgc cgtatcatt                                                19

<210> SEQ ID NO 35
<211> LENGTH: 21
<212> TYPE: DNA
<213> ORGANISM: Artificial Sequence
<220> FEATURE:
<223> OTHER INFORMATION: Illumina TruSeq P7

<400> SEQUENCE: 35
agcatacggc agaagacgaa c                                             21

<210> SEQ ID NO 36
<211> LENGTH: 21
<212> TYPE: DNA
<213> ORGANISM: Artificial Sequence
<220> FEATURE:
<223> OTHER INFORMATION: Illumina TruSeq P7

<400> SEQUENCE: 36
gttcgtcttc tgccgtatgc t                                             21

<210> SEQ ID NO 37
<211> LENGTH: 34
<212> TYPE: DNA
<213> ORGANISM: Artificial Sequence
<220> FEATURE:
<223> OTHER INFORMATION: TS index primer

<400> SEQUENCE: 37
agatcggaag agcacacgtc tgaactccag tcac                               34

<210> SEQ ID NO 38
<211> LENGTH: 34
<212> TYPE: DNA
<213> ORGANISM: Artificial Sequence
<220> FEATURE:
<223> OTHER INFORMATION: TS index primer

<400> SEQUENCE: 38
gtgactggag ttcagacgtg tgctcttccg atct                               34

<210> SEQ ID NO 39
<211> LENGTH: 33
<212> TYPE: DNA
<213> ORGANISM: Artificial Sequence
<220> FEATURE:
<223> OTHER INFORMATION: TS R2 Seq Primer

<400> SEQUENCE: 39
```
ctagccttct cgtgtgcaga cttgaggtca gtg                                    33

<210> SEQ ID NO 40
<211> LENGTH: 33
<212> TYPE: DNA
<213> ORGANISM: Artificial Sequence
<220> FEATURE:
<223> OTHER INFORMATION: TS R2 Seq Primer

<400> SEQUENCE: 40
cactgacctc aagtctgcac acgagaaggc tag                                    33

<210> SEQ ID NO 41
<211> LENGTH: 33
<212> TYPE: DNA
<213> ORGANISM: Artificial Sequence
<220> FEATURE:
<223> OTHER INFORMATION: Illumina Universal R1

<400> SEQUENCE: 41
acactctttc cctacacgac gctcttccga tct                                    33

<210> SEQ ID NO 42
<211> LENGTH: 33
<212> TYPE: DNA
<213> ORGANISM: Artificial Sequence
<220> FEATURE:
<223> OTHER INFORMATION: Illumina Universal R1

<400> SEQUENCE: 42
agatcggaag agcgtcgtgt agggaaagag tgt                                    33

<210> SEQ ID NO 43
<211> LENGTH: 30
<212> TYPE: DNA
<213> ORGANISM: Artificial Sequence
<220> FEATURE:
<223> OTHER INFORMATION: Illumina PCR index2 fastqc

<400> SEQUENCE: 43
cgatgtatct cgtatgccgt cttctgcttg                                        30

<210> SEQ ID NO 44
<211> LENGTH: 30
<212> TYPE: DNA
<213> ORGANISM: Artificial Sequence
<220> FEATURE:
<223> OTHER INFORMATION: Illumina PCR index2 fastqc

<400> SEQUENCE: 44
caagcagaag acggcatacg agatacatcg                                        30

<210> SEQ ID NO 45
<211> LENGTH: 25
<212> TYPE: DNA
<213> ORGANISM: Artificial Sequence
<220> FEATURE:
<223> OTHER INFORMATION: Illumina SE PCR fastqc

<400> SEQUENCE: 45
agatctcggt ggtcgccgta tcatt                                             25

<210> SEQ ID NO 46
<211> LENGTH: 25
<212> TYPE: DNA

```
<213> ORGANISM: Artificial Sequence
<220> FEATURE:
<223> OTHER INFORMATION: Illumina SE PCR fastqc

<400> SEQUENCE: 46
aatgatacgg cgaccaccga gatct                                              25

<210> SEQ ID NO 47
<211> LENGTH: 25
<212> TYPE: DNA
<213> ORGANISM: Artificial Sequence
<220> FEATURE:
<223> OTHER INFORMATION: Clontech common

<400> SEQUENCE: 47
aagcagtggt atcaacgcag agtac                                              25

<210> SEQ ID NO 48
<211> LENGTH: 25
<212> TYPE: DNA
<213> ORGANISM: Artificial Sequence
<220> FEATURE:
<223> OTHER INFORMATION: Clontech common

<400> SEQUENCE: 48
gtactctgcg ttgataccac tgctt                                              25

<210> SEQ ID NO 49
<211> LENGTH: 30
<212> TYPE: DNA
<213> ORGANISM: Artificial Sequence
<220> FEATURE:
<223> OTHER INFORMATION: Clontech SMARTERIIA
<220> FEATURE:
<221> NAME/KEY: misc_feature
<222> LOCATION: (26)..(30)
<223> OTHER INFORMATION: n is a, c, g, or t

<400> SEQUENCE: 49
aagcagtggt atcaacgcag agtacnnnnn                                         30

<210> SEQ ID NO 50
<211> LENGTH: 30
<212> TYPE: DNA
<213> ORGANISM: Artificial Sequence
<220> FEATURE:
<223> OTHER INFORMATION: Clontech SMARTERIIA
<220> FEATURE:
<221> NAME/KEY: misc_feature
<222> LOCATION: (1)..(5)
<223> OTHER INFORMATION: n is a, c, g, or t

<400> SEQUENCE: 50
nnnnngtact ctgcgttgat accactgctt                                         30

<210> SEQ ID NO 51
<211> LENGTH: 50
<212> TYPE: DNA
<213> ORGANISM: Artificial Sequence
<220> FEATURE:
<223> OTHER INFORMATION: Clontech polyT

<400> SEQUENCE: 51
aagcagtggt atcaacgcag agtacttttt tttttttttt tttttttttt                   50

<210> SEQ ID NO 52
<211> LENGTH: 50
```

```
<212> TYPE: DNA
<213> ORGANISM: Artificial Sequence
<220> FEATURE:
<223> OTHER INFORMATION: Clontech polyT

<400> SEQUENCE: 52
aaaaaaaaaa aaaaaaaaaa aaaaagtact ctgcgttgat accactgctt              50

<210> SEQ ID NO 53
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: (1)..(1)
<223> OTHER INFORMATION: G, S, A or Q
<220> FEATURE:
<221> NAME/KEY: misc_feature
<222> LOCATION: (4)..(4)
<223> OTHER INFORMATION: Xaa can be any naturally occurring amino acid

<400> SEQUENCE: 53

Gly Pro Gly Xaa
1

<210> SEQ ID NO 54
<211> LENGTH: 5
<212> TYPE: PRT
<213> ORGANISM: Artificial Sequence
<220> FEATURE:
<223> OTHER INFORMATION: Motif

<400> SEQUENCE: 54

Gly Pro Gly Pro Gln
1               5

<210> SEQ ID NO 55
<211> LENGTH: 4
<212> TYPE: PRT
<213> ORGANISM: Artificial Sequence
<220> FEATURE:
<223> OTHER INFORMATION: Motif

<400> SEQUENCE: 55

Gly Pro Gly Gly
1

<210> SEQ ID NO 56
<211> LENGTH: 9
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: (6)..(6)
<223> OTHER INFORMATION: A or T

<400> SEQUENCE: 56

Val Ser Val Val Ser Xaa Thr Val Ser
1               5

<210> SEQ ID NO 57
<211> LENGTH: 2123
<212> TYPE: DNA
<213> ORGANISM: Caerostris darwini
```

<400> SEQUENCE: 57

```
tacggaccag gtggcgcagc agctgctgcc gctgccgcag gaggttatgg acctggagga      60
agtggcccat caggacctgg atctcaaggg ccatctggac caggatccca aggacctgga     120
ggagcaggac catatggacc aggtggagca gcagcagctg cggcagccgc aggtggatat     180
ggaccaggaa gtcaaggccc atcaggacct ggatcacaag gaccaggagg ggcagggcca     240
tatggaccag gtggagcagc agcagctgca gcagctgcag gtggatatgc accagctggg     300
caaggacaat ctggacctgg atctcaagga caaggacaat caggaccagg ttcacaagga     360
ccaggaggag caggaccgta tggacctggt ggagctgcag ccgctggtgg atatggacca     420
ggaggacaag gaccatcagg gcctggatca aaggaccag gaggacgagg accatcagga      480
cctggtggag cagcagcagc tgcagcaagt gcatatggac ccggaggaca aggaccatca     540
gggccaggat ctcaaggacc aggagggcaa ggaccatatg gaccaggtgc agcagcagct     600
gcagcagcag ccgtggata tggacccggt ggacgaggac cctcaggacc tggatctcaa      660
ggaccttcag gacctggatc acaaggacca ggaggggcag ggccatatgg accaggtgga     720
gcagcagcag ctgcagcagc tgcaggtgga tatgcaccag ctgggcaagg acaatctgga     780
cctggatctc aaggacaagg acaatcagga ccaggttcac aaggaccagg aggagcagga     840
ccgtatggac ctggtggagc agcagcagct gccgcagccg ctggcggata tggaccaggt     900
ggacagggac catctggacc tggttctcaa ggacctggaa gtcaaggacc atcaggacct     960
ggactagcag ctgcagctgc agcagcaggt ggatatggac ccggaggaca aggaccatca    1020
ggatcagcat ctcaaggacc aggtgggcaa ggaccatacg gaccaggtgg cgcagcagct    1080
gctgccgctg ccgcaggagg ttatggacct ggaggaagtg gcccatcagg acctggatct    1140
caagggccat ctggaccagg atcccaagga cctggaggag caggaccata tggaccaggt    1200
ggagcagcag cagctgcggc agccgcaggt ggatatggac caggaagtca aggcccatca    1260
ggacctggat cccaaggtcc tggaggtcgg ggaccatctg gacccggatc acaaggacct    1320
ggaggagctg gaccatatgg accaggtgga gcagcagcag ctgcagcagc cgcaggtgga    1380
tatggacctg gaagtcaagg cccatctgga cctggatctc aaggaccagg aggacaagga    1440
ccatatggac caggtggagc agcagcagct gcagcagccg caggtggata tggaccagga    1500
agtcaaggcc catctggacc tggatctcaa ggaccaggag acaaggacc atatggacca     1560
agtggagctg cagcagctgc agcagccgct ggtggatatg gaccagcagg acaagggccc    1620
tctggacctg gatctcaagg accaggagga caaggaccat ctggtcctgg cggttacgga    1680
cctagtagtg cagcagctgc atttggtggt tatggaccaa gtgggcaaat accctctgct    1740
gctgcggcgg cctctcgttt atcatctcca gcagtcgctt caagagtttc ctccactgtg    1800
tcctcattgg tatcaagcgg gccaacaagt caaggtgctt tatcaaatgc tataagcaat    1860
gccgtctccc aaataagtgc tagtaatcct ggtctctctg gatgtgatgt ccttgttcaa    1920
gcattgttag aaattgtatc agctcttgtt cacattcttg gttcttctag tgtaggtcaa    1980
gtgagctaca atactgcagg ccagtctgct gcagtagtta gtcaatctat atcacaagct    2040
cttggctaag cattcaactt tttcttccaa cacaataatt ttctgttatg ttgaatatct    2100
ttcaataaag gatgagcata ttt                                            2123
```

<210> SEQ ID NO 58
<211> LENGTH: 1722
<212> TYPE: DNA
<213> ORGANISM: Caerostris darwini

<400> SEQUENCE: 58

```
ccgctggtgg tgctggtgga cgaggcggat tgggaggaca aggaggcgga caaggagccg    60
gtggtgctgg tcaaggcggt tacggatctg gattaggagg actaggtgga ggagctgctg   120
ctgctgctgc tgccgctggt ggtgcaggag gattaggcgg acaaggaggt ggacaaggtg   180
caggacaagg aggttatggt tccggacaag gtggacaagg tgcaggatct gctgctgctg   240
cagctgccgc tggtggtgca ggtggacgag gcggtttggg aggacaagga ggcggacaag   300
gagccggcgg tgctggtcaa ggcggttacg atctggatt aggaggacta ggtggaggag   360
ctgcagctgc tgctgctgcc gctggtggtg caggaggatt aggcggacaa ggaggtggcc   420
aaggagcagg acaaggaggt tatggatccg gacaaggtgg acaaggtgca ggatctgctg   480
ctgctgcagc tgccgctggt ggacgaggtg gttatggagg acaaggaggt ggacaaggag   540
ccggtggtgc tggtcaaggc ggttacggat ctggattagg aggactaggt ggaggagctg   600
ctgctgctgc tgctgccgct ggtggtgcag gaggattagg cggacaagga ggtggccaag   660
gagcaggaca aggaggttat ggatctggac aaggtggaca aggtgcagga tctgctgctg   720
ctgcagctgc cgctggtggt gcgggtggac taggtggtta tggaggacaa ggaggtggac   780
aaggagccgg tggtgctggt caaggtggtt acggatctgg attaggagga ctaggtggag   840
gagctgccgc tgctgctgct gccgctggtg gtgcaggagg cttagtcgga caaggaggtg   900
gacaaggtgc aggacaagga ggttatggat ccggacaagg tggacaaggt gcaggatctg   960
ctgctgctgc agctgccgct ggtggtgctg gtggacgagg cggattggga ggacaaggag  1020
gcggacaagg agccggtggt gctggtcaag gcggttacgg atctggatta ggaggactag  1080
gtggaggagc ttccgctgct gctgctgccg ctggtggtgc aggaggctta ggcggacaag  1140
gaggtggaca aggggcagga caaggaggtt atggatccgg acaaggagga caaggtgcag  1200
gatctgctgc cgctgctgct gcagctgtgg gttctggagg cttaggtgga caaggtggtt  1260
atggtggaca aggtggttat ggtggaggat atggaggtca acaagtagca gcttcagcca  1320
caacagcatc tgctgcggct tcacgacttt cttctcctgc tgcaagttca agagtatcct  1380
cagcagtttc ttcattagta tcaagcggcc caactagtcc agctgctctt tccaatacaa  1440
tcagtaatgt ggtttctcaa gttggcgcta gtaatcctgg tctatctgga tgtgatgttc  1500
ttgttcaagc attattggaa attgtttctg ctccttattca catacttgga tcatctagta  1560
ttggccaagt taattacggg gctaccgctc aatcaactgg cattgttagt caatctattt  1620
cccaagctct tggttaaatg atgttattaa gaatttttt caataaatcc tttataatga  1680
attagtttgt tacaataaaa caacgcattt ttgaaatatc gt                     1722
```

<210> SEQ ID NO 59
<211> LENGTH: 1509
<212> TYPE: DNA
<213> ORGANISM: Caerostris darwini

<400> SEQUENCE: 59

```
caaggaggtg acaaggtgc aggacaagga ggttatggat ccggacaagg tggacaaggt    60
gcaggatctg ctgctgctgc agctgccgct ggtggacgag gtggtatgg aggacaagga   120
ggtggacaag gagccggtgg tgctggtcaa ggcggttacg atctggatt aggaggacta   180
ggtggaggag ctgctgctgc cgctggtggt gcaggaggct taggcggaca aggaggtgga   240
caaggtgcag gacaaggagg ttatggttcc ggacaaggtg gacaaggtgc aggatctgct   300
```

| | |
|---|---|
| gctgctgcag ctgccgctgg tggacgaggt ggttatggag gacaaggggg tggacaagga | 360 |
| gccggtggtg ctggtcaagg cggttacgga tctggattag gaggactagg tggaggagct | 420 |
| gctgctgctg ctgctgccgc tggtggtgca ggaggcttag ccggacaagg aggtggacaa | 480 |
| ggtgcaggac aaggaggtta tggatccgga caaggtggac aaggtgcagg atctgctgct | 540 |
| gctgctgccg ccgctggtgg tgctggtgga cgaggtggtt acggaggaca aggaggccag | 600 |
| ggagctggtg gtgctggtca aggaggttac ggatctggat taggaggact aggtggagga | 660 |
| gctgccgctg ctgctgctgc cgctggtggt gcaggtggct taggcggaca aggaggtgga | 720 |
| caaggtgcag gacaaggagg ttatggatcc ggacaaggtg acaaggtgc aggatctgct | 780 |
| gctgctgcag ctgccgctgg tggtgctggt ggacaaggtg gttacggagg acaaggtgga | 840 |
| caaggagccg gtggtgctgg tcaaggtggt tacggatctg gattaggagg agtaggtgga | 900 |
| ggagctgccg ctggtggtgc aggaggatta ggcggacaag gaggtggaca aggtgcagga | 960 |
| caaggaggtt atggatccgg acaaggtgga caaggtgcag gatctgctgc cgctgcttct | 1020 |
| gcagctggtg gtgctttagg cttaggtgga caaggcggtt atggtggaca aatgggttat | 1080 |
| ggtggaggat atggaggtca acaagtagca gcttcagccg caacagcgtc tgctgccgct | 1140 |
| tcacgactct cttctcctga tgccagttca agagtttcct cagcagtttc ttcattagta | 1200 |
| tcaagtggcc caaccaatcc agctgctctt tccaatacaa tcggtagtgt tgtttcacaa | 1260 |
| attggagcta gcaatcctgg tctatctggt tgtgatattc ttgttcaagc attgttggaa | 1320 |
| atcgtttctg ctcttataca aatcctcgca tcatctagta tcggccatgt taattatggg | 1380 |
| gcaaccgctc aatcaactgg tattgttagt caatctattt cccaagcact tggttaaatg | 1440 |
| atgacgttta gagtcttttg aataaactct tataattatt taaattgtta caataaaata | 1500 |
| atgcattt | 1509 |

<210> SEQ ID NO 60
<211> LENGTH: 2132
<212> TYPE: DNA
<213> ORGANISM: Caerostris darwini

<400> SEQUENCE: 60

| | |
|---|---|
| gaccacaaag tccatatgga ccaggtccac aaggcccagg cccgcaagga ccaggaccac | 60 |
| aaggaccttc aggaccaggt ccgcaacgac cacaaggacc aggtccacaa gggccatacg | 120 |
| gcccaggtgg cgtcagtgta gtgtctgcaa cagtttccgg tcctggacca caaggaccat | 180 |
| caggaccagg accacaaggt ccgtatggac caggaccaca aggcccagga ccgcaaggac | 240 |
| caggaccaca attacctgga ccacaaggac catcaggacc aggaccacaa ggtccgtatg | 300 |
| gaccaggacc acaaggtcca ggaccgcaag gaccaggacc acaaggacct tcaggaccag | 360 |
| gtccgcagca accacaagga ccaggaccac aaagaccata cggcccaggt ggcgtcagtg | 420 |
| tagtgtctac tacagtttcc ggacctggac ctcaaggacc attaggacca ggagcacaag | 480 |
| tcccgtacgg accaggtcca caagtcccag gaccgcaagg accaggacca caaggacctt | 540 |
| caggaccagg tcctcaacga ccacaaggac caggaccaca agggccatat ggtccaggtg | 600 |
| gcgtcagtgt agtgtctcaa acagtttccg gtcctggacc acaaggacca tcaggaccag | 660 |
| gaccacaagg tccgtatgga ccaggaccac aaggaccagg accgcaagga ccagcaccac | 720 |
| aaggaccttc aggaccaggt ccccaaagac cacaaggacc aggaccacaa agaccgtatg | 780 |
| gcccaggtgg tatcagtgtg gtgtctacta cagtttccgg acctggacct caagggccat | 840 |
| cagcaccagg accacaaggt ccgtatggac caggaccaca agtcccagga ccgcaaggac | 900 |

```
caggaccaca aggaccttca ggaccaggtc ctcaacgacc acaaggacca ggaccacaag    960
ggccatatgg tccaggtggc gtcagtgtag tgtctcaaac agtttccggt cctggaccac   1020
aaggaccatc aggaccagga ccacaaggtc cgtatggacc aggaccacaa ggaccaggac   1080
cgcaaggacc aggaccacaa ggaccttcag gagcaggtcc gcaacgacca caaggaccag   1140
gtccacaagg gccatacggc ccaggtggcg tcagtgtagt gtctgcaaca gtttccggtc   1200
ctggaccaca aggaccatca ggaccaggac cacaaggtcc gtatggacca ggaccacaag   1260
gcccaggacc gcaaagacca gtaccacaag gaccttcagg accacgtccg cagcaaccac   1320
aaggaccagg accacaaaga ccattcggcc caggtggcgt cagtgcagtg tctactacag   1380
ttttcggacc cggaccccaa ggaccatcag gaccaggtcc acaaggcccg tatggaccag   1440
gtccacaagg accaggcccg caaggaccag gaccacaagg accttcagga caaggtccgc   1500
aacgacttc aggaccacga ccacaaggac catatggacc aggcggtatc agtgtagtgt   1560
ctgctacagt ttccggccct ggaccacaag gaccttcagg accaggacca caacgcccgt   1620
atggaccagg accagaaggc ccaggcctc aaggagcagg accacaagga ccaggtctgc   1680
aaagaccttc aggaccaggc ccacaaggac cctatggtcc gggcccacga ggtccttcat   1740
ctacccctga atctgcggca ataaatgcag cttctcgttt gtcctctcct gctgcgtcgt   1800
ctagggtatc ttctactgtt tctcaattag tctcaagtgg acctcctaac agtgctgcag   1860
tatctggtgc tataagtagt ttggtatctc aagttagtgc cagcaatcca ggcctttccg   1920
gttgtgatat tctcgtccaa gctttgatgg aattgttatc tgctttagtt agtattgttg   1980
ggtcttccag tatcggtcag gttaattatg gtgcaagtgg tcagtacgct cagttggtta   2040
gccaagcaat tggtcaagca ttttgatgca atacttcgcg gactctttt tttaatactt    2100
ctgtcttgta aattttaata aatatatgat at                                 2132

<210> SEQ ID NO 61
<211> LENGTH: 1636
<212> TYPE: DNA
<213> ORGANISM: Caerostris darwini

<400> SEQUENCE: 61
gaccacaagg tccatatgga ccaggaccac agggaccagg accacaagga ccgggaccac     60
agggaccagg accacaagga ccaggaccgc gaggaccttc aggaccagga ccacaaggac    120
catatggtcc aggcggtgtc agtgtagtgt ctgcttcagt ttctggacct ggaccccaag    180
gaccgtcagg accaggacca cagggtccat atggaccagg acctcaggga ccaggaccac    240
aaggaccagg accacaggga ccaggaccac aaggaccagg accgcgagga ccctcaggac    300
caggaccaca aggaccatat gggccaggcg tgtcagtgt agcgtctgct tcagtttctg     360
gacctggacc acaaggaccg tcaggaccag gaccacaggg tccatatggg ccaggaccac    420
agggaccagg cccacgagga ccaggaccgc agggaccagg accacaaggt ccaggaccgc    480
aaggaccttc aggaccagga ccacaaggac catatggtcc aggtggtgtc agtgtagtgt    540
ctgcttcagt ttctggacct ggaccacaag gaccatcagg accaggacca cagggtccat    600
atggacctgg accacaggga ccaggacccc aaggaccagg accacaggga ccaggaccac    660
aaggaccagg accgcgagga ccttcaggac caggaccaca aggaccatat ggtccaggcg    720
gtgtcagtgt agtgtctgct tcagtttctg gacctggacc acaaggacct tcaggaccag    780
gaccacaagg tccatatggg ccaggaccac agggaccagg cccacaagta ccaggaccac    840
```

| | |
|---|---|
| agggtccagg accacaaggt ccaggaccac aaggaccttc aggaccagga ccacaaggac | 900 |
| catatggtcc aggcggtgtc agtgtagtgt ctgcttcagt ttctggacct ggaccacaag | 960 |
| gaccgtcagg accaggacca cagggtccat atggaccagg accacaggga ccaggtccac | 1020 |
| gaggaccagg accacaagga ccaggacctc aaggtccagg accgcaggga ccttcaggac | 1080 |
| caggaccaca gggaccatat ggtcccggcg gtgtcagtgt agtgtctgct tcagtttctg | 1140 |
| gacctggacc acaaggacca tccggtcctg cagtcaatgc agctgcacgt tgtcatctc | 1200 |
| ctgatgcatc atctagagta tcttcaactg tttctcaatt agtatctggt ggaccaacta | 1260 |
| gtggtgcagc agtttctaat gctttaagta gcttggtatc tcaagttgga gccagcaatc | 1320 |
| caggccttc aggttgtgat attcttgtcc aagctttgat ggaaatgctt tctgctttag | 1380 |
| ttagcatcgt tggctcttcc agtattggtc aagttaatta tggcgcaagt ggtcaatata | 1440 |
| ctcagatgat tggccaagca attgctcaag cattttaatg aaacttttta atgacttgat | 1500 |
| ttttgaaatt atcctgtctt gtaaattta ataaatagta agtttgaaaa gcagttttt | 1560 |
| attgatttat attttagtac agaaagctat gtgtgcaaaa tatatgaaat aaaatttaaa | 1620 |
| tattatttt atgatt | 1636 |

<210> SEQ ID NO 62
<211> LENGTH: 1335
<212> TYPE: DNA
<213> ORGANISM: Caerostris darwini
<220> FEATURE:
<221> NAME/KEY: misc_feature
<222> LOCATION: (103)..(103)
<223> OTHER INFORMATION: n is a, c, g, or t

<400> SEQUENCE: 62

| | |
|---|---|
| ggccgtggcg gttatggagg acgaggcgga gcgggatctt catctgctgc tgcggcagcg | 60 |
| ggtagtggtg gcgatggatc tggttcaggc ggttatggag gangaggagg acaaggtggt | 120 |
| gacggtgctt cgtctgctgc tgccgcagcg ggtagtggtg gtgatggatc tggttctggc | 180 |
| ggttacggag gaagaggagg aagaggaggg caaggtggtg ccggttcttc atctgctgct | 240 |
| gccgcagcgg gcagtggtgg tgatggatct ggttcaggcg gttatggagg aagaggagga | 300 |
| cgaggcggag cgggatcttc atctgctgct tccgcagctg ctggtggtga agatggattc | 360 |
| ggccgtggcg gttatggagg acgaggcgga gcgggatctt catctgctgc tgcggcagcg | 420 |
| ggtagtggtg gcgatggatc tggttcaggc ggttatggag gaagaggagg acaaggtggt | 480 |
| gccggttctt catctgctgc tgcagctggt agtggtggcg atggatatgg ttctggcggt | 540 |
| tacggaggaa gaggaggaca aggtggtgcc ggttcttcgt ctgctgcttc cgcagcgggt | 600 |
| agtggtggtg atggatttgg ttctggcttt tacggaggta gaggaggaga aggtggtgcc | 660 |
| ggttcttcgt ctgctgctgc agcagcgggt agtggtggcg atggatatgg ttctggcggt | 720 |
| tacggaggac gaggaggaca gggcggtgcg ggaggtgcat ctgcttctgc agttgcagct | 780 |
| ggcggcggta gaggtcaagg aggatacggt ggtagaggag acaaggagg tgctggttct | 840 |
| tcatctgcgt catctacagc gtctgccgca gcatctcgcc tttatagtcc cgattcaagt | 900 |
| gctcgaattt catcagctgt ttcatccttg gcatcctacg gaccaaataa tccaacagct | 960 |
| ctttcagatg ttataagcaa cacaatgtcc caagtaagtt atagcagtcc ggaattgtct | 1020 |
| ggctgcgatg tgctggttca aaccttaatg gaagttgttt cagctctcgt acatattctt | 1080 |
| agtgtatctg atataggccc agttgccat gattctgatc aggctgtcca agttgtgggt | 1140 |
| caatcgttta ataatttgat gtattaaata ttatactact gtttttattc aataactata | 1200 |

```
ctatttagt atattatttt ttttagtaat atggcgtaaa attaacctta taagttttaa    1260
taaaattaaa agttgtgttg ttttttcaac tcattctttg ttgttctttt ctgcttcaat    1320
aaatatttaa acaac                                                     1335
```

<210> SEQ ID NO 63
<211> LENGTH: 1444
<212> TYPE: DNA
<213> ORGANISM: Caerostris darwini

<400> SEQUENCE: 63

```
gtggaggatt aggcgattct ggaggaggat taggtggttc tagaggtgga ctaggtggtt      60
ctggaggtgg actaggtggt tctggtggag gattaggcgg ttctggagga ggattaggcg     120
gttctggagg tggactaggg ggttctggag gtggacaagg tggttctgaa ggtggattag     180
gtggttctgg aggaggatta ggcggttcta gtggaagatt aggcggttcc ggtggaagat     240
taggtggttc tggaggagga ttaggccgtt ctggaggagg aataggcggt tctggaggag     300
gattaggggg ttctggaaga ggattaggcg gttctggagt tggaccaggt ggttctggtg     360
gaggtctagg tgattctgga ggtggacttg gtggttctgg tggaggagta ggcggttctg     420
gaggtggatt aggtgattct ggaggaagat taggtagttc tggaagtgtc ggaggatcag     480
gtggacgtgg aggattaggt ggtcctggaa gttcaggcgg aacagatgga caaggtgcaa     540
tgggtggttc tggaggtaga ggattggatg gtccaggaag tttaggagga acaggtggac     600
aaggaggaat ggatggtcct ggaggtgaag tagatggtga ttatagtgct gcatctgcat     660
catctcgtgg gctgggtggt tctggtccag gaggttatgg tagaagttta ggtggaccag     720
gaggatttgg aggtgacaga gacttgggtg atagcgctag ctcagcagct gcatcagcag     780
gtggagatgg tggtagcagt ggtcccggaa aaagaggtgg ttacggcaga ggttctggtg     840
gagcgaaggg attaagcggc tcaggtggag gaattggaag tggtgcagca gctaccctag     900
caggaggtct tggtggatct ttatctgcag gctctggaga attcttagga acatcaggtg     960
gacgaggagg tgattcttcc caaacgagtg catcgtctac tatatcttct gccgcatctc    1020
gtctttcttc tccagaagct agctcaagaa tttcatcagt tgtttcctct tttctatcta    1080
acggtataga caatcccagt tctttatcaa gttctctgag cggtattgtg tcaaggatta    1140
gttcactcaa tcctatgcta tcttcttgtg acattctcct tcaagcattg ctggaaattg    1200
tttcggcgct gcttcagatt cttgcctctt ctaacatagg tccgattgac tacagttcta    1260
cacgtcagtc tacaggaatt gtaagtcagt ctgtatatca agctttcagt taatatttct    1320
gtttatgaaa aaggaatttt tcaattatac atctgtattg aaatatctat gttaccgaaa    1380
atctatatta agcattctat ctgtttgtta ttaataaaat ttgttgaaat aaaccatgca    1440
tttt                                                                  1444
```

<210> SEQ ID NO 64
<211> LENGTH: 558
<212> TYPE: DNA
<213> ORGANISM: Caerostris darwini

<400> SEQUENCE: 64

```
ggcgctggag gtgctggcgg acgtggaggt tacggtggtg gatctggtgc aggagccggc      60
gctgcagctg ctgcaggtgc aggagcaggc ggtggctacg gaggtggaca gggtggatac    120
ggtggtggat ctggttctgc tgctggtggt gcttctgcag caggtgcagc cgttggaagt    180
```

```
tacggaagcg gaggatatgg aggaggtgca agttacgctt catctagtgc tggaagcgtt    240
gttaacactg tttcttcacg tataacatcc tccgaatctt cttcaagaat atcttctgcg    300
gcatcgactc tgactgctgg tggcgcattg aatgctgctg ctttgtccga tgtcattgga    360
aatgtttatt ctcaagtaag cgcttcagcg ggtggtgcgt ctggtgcaga agtcttagtt    420
caaactctgt tggaaattgt atcagctttg ctgcatattt tgagttcatc aaacattggc    480
tatgttgatt tcggtggtgt ttcttcttct gctaatgccg ttgcacagtc tgtagctgca    540
gccttgggtt aagttttta                                                 558

<210> SEQ ID NO 65
<211> LENGTH: 1619
<212> TYPE: DNA
<213> ORGANISM: Caerostris darwini

<400> SEQUENCE: 65
gagctctagg atctggtgga ggattcagag gatttggtgg accgggagga cctggaggtc      60
ccggaggacc aggagcacca ggtgcgccag gcggaccggg agtaggtggt cctggtggat     120
actatggccc aggagctggt ggtgctggtg gaatgcttgg atctggagca ggtggtgttt     180
ccggaggacc tggaggtctc ggcggacctg gtggatttgg aggaccaggc ggtgttggag     240
gacttggtgg aatgggtggt gtaggacccg gtggttctgg aataatgtac ggtccgggag     300
ccggaggtgc aggtggaggt tttggatccg gagcaggtgt cgcagctgga ggtcaaggag     360
gatttggtgg agcaggtggc ccaggcggac caggaggggc gggaggacca ggtgcagcag     420
gtggtgttgg tggtatctca ggacctggtg gtgctggacc atcaggtgga ggtgctggtg     480
gagtaaccgt tgtagataat ctctctgtga atgttggagg tgcaggagct ggtggtgccg     540
gaactggtgg tgctggaggt tcacttggtg gtcttggagg attcggtgga ccaggcggtc     600
cgggaggtcc tggcggacca ggtggaccag gaggttctgg agcagctgga ggcatgacag     660
gcccaggtgc tggaggatct gccggtggcg ctggaggatc tggcccaata actatttctg     720
gaacactgtc cgtaggaggt gcaggagctg gaggagccgg tcctggtgca ggaggtcgat     780
atggatccgg tggatcgggc ggcggtgcag gaggatttgg aggaccaggt gggccaggtg     840
gaccaggtgg accgggaggt ccgggtggtc ttggtggagc aggagctgga ggtgttggac     900
caggaacagg aggggcttcc agtcccggcg gaggttcagg accagtaact gttactgata     960
atgtctctgt tactgtcgga ggttcaggag gatccggtgg gtcagatgct ggtggggccg    1020
gtggagctct aggatctggt ggaggattca gaggatttgg tggaccggga ggacctggag    1080
gtcccggagg accaggagca ccaggtgcgc caggcggagc aggagcgggt attattggag    1140
gagctccttc tcctagtggt ggatcttccg gtcccgtaac tgtttctgat aatatatcca    1200
taacaatagg aggtcaaatg tcatctgctg gttcagctgg acctggattc caaggacaac    1260
ctgtggtatc cagattacct tccttagtga atggaatgct cggttctatg caagcaaatg    1320
ggcttaatta ccagaatttg ggaaatcttt tgtcgcgtta ttctactgga tctgaacct     1380 gtaacagtaa tgatctaaat cttttaatgg aagctcttca agcagctctt cattgtctta    1440
gttacccagg tcctgcgtcg gttcctagca tgcctcctcc atcttctacg tctgcataca    1500
tgcagtctat tcgaagagta tttggttact aagcgcaagc aattataaaa ttatattaaa    1560
atatatttgt tcattttcaa atataggaca aatctaataa atatttgaag cacaaaaaaa    1619

<210> SEQ ID NO 66
<211> LENGTH: 1093
```

<212> TYPE: DNA
<213> ORGANISM: Caerostris darwini

<400> SEQUENCE: 66
aggctgcaag tgaggcagca agcagcagtg ccagctcctc aagtgcctct gcatttgcgc 60
aatcggcatc acaatccctg gccatgtcaa gttctttcgc cagcgccttt tctgccgctg 120
cctcttcagc tgaatctctc cgtagcctag gcttccaaat aggcaatgcg ttagtcaaca 180
atctcggact ccgactacaa ccggcggacg tagcgcaagc tctatcagcg gtcggcactg 240
gagccagcac taatgcctac gcaaatgccc tagcgagtgc agttgcccgg gcagcggcca 300
gtcagggtac tttgaatgct ggcaattccg gtagccttgc ctccgcagct tcggcagcca 360
tctcagcagc agctgcatcc gcctcttcct cgcagttcca atctgcagcc gcacaacaac 420
aagcagcagc cgcagccttc cgtcaagcag catcgcagag cggcagccag agtgctgcac 480
gtagcggatc tcagagttct tcctccgcaa ccacaacttc gacctccggt agccaggctg 540
caagtgaggc agcaagccgc agggcaggag cctcagcagg agcgggttcg aatgcaggtg 600
cttttggggc tgcgttcgga aggtctgctg gtggaactgg tgcgaacgca ggtgcttttg 660
gagctgcgct aggaaggccg gttggtcagg atgtcgcacc ttctttgcaa tctgcccttg 720
ctccggtctt gtcttcttct gtcctatctt cttccgatgc aactgcaaga gtgaacagtt 780
tagccgagtc cgtctcttca gccattgctt cttctggcgg ttctttaaat gttgccacct 840
tcttggattc gttatcttca gtcggatctc aagttagatc gggcacatct ctggatgcat 900
ctcaagcgac ttctgaggtc ctcttggaag ccattgcggc gcttattaaa gttatcaatg 960
gagccggaat caccagagtg aatcttgaca atgtttccaa tgtcaattcg gctttagtgt 1020
cagcactagc cggttgattt tcttaagacg tttcatagaa ggcttttcaa caatgcgttt 1080
atatttttta tta 1093

<210> SEQ ID NO 67
<211> LENGTH: 925
<212> TYPE: DNA
<213> ORGANISM: Caerostris darwini

<400> SEQUENCE: 67
ggatacggtg gtggagctgg agctggagca ggtgctgctg gagcaggtgg agcaggtgga 60
tatggaggag gatacggtgg tggagctgga gctggagcag gtgctgctgg agcaggtgga 120
gcaggtggat atggaggagg atacggtggt ggagctggag caggtgctgc tgctggagca 180
ggtgctggcg gacgtggagt ttacggaggc ggatctggtg ctggagctgc tgcgggagct 240
ggagcaggtg ctgcagttgg atatggtgga ggctacggag gtggagccgg tgcaggtgca 300
ggcgctgccg ctgctgcagg agctggcgca ggtgcgggtg gtggctatgg aggttacagc 360
ggtggtgctg gtgctggagc cggtgctgca gctgcagctg gagctggcgc aggaggtagc 420
tatggaggcg gatttggagg ttacagtgtt ggcgctggtt caggtgcagg tgtagtttca 480
actgtttctt ctactacaac tcgtctcagt tctgcggaag cttcttcaag aatatcgact 540
gccgcctctt ctcttgtagc tggtggtgtt gtaaatacaa gtgtcctgcc ttccgtcatt 600
tcgaaccttt attcacaagt aagcgcgtcg tcgcccggtg cgtcttcaag cgaagtattg 660
gtgcaagtct tgttggaaat tatttcatct ttgatacata tcctcggttc ttcaagtgtc 720
ggacaaataa atctgggttc tgtggcctca tctgcagccg cagttggtca atctttacaa 780
gctgttatgg gttaagtcag ttgattttcc cttatgttac aatatatatt aatgtttaac 840

```
taatggatga ttttctttt tctgtattta catgttgtaa caatacatga ataattctg      900 catgaaacaa aaaaaaaaaa caaac                                           925
```

<210> SEQ ID NO 68
<211> LENGTH: 790
<212> TYPE: DNA
<213> ORGANISM: Caerostris darwini

<400> SEQUENCE: 68

```
atcacgagca ccttctgcct attctggagg atccatggca tctcttccat cacaaggatc     60
ttctgccttt tctggaggtt ctgtagcatc tcttcaatca caaggatcct ctgcctattc    120
tggagcttct gcagcatctc ttcaatcacg agcgtcttct gcttattctg gaggttctgc    180
aagatctctt caatcacaag cttcgtctgc cttttctgga ggttccggga cacaatatgg    240
ttcttcccaa tcatcatcta tgtcttcctc ggctgctctg ggtcctataa ttgcaccagt    300
tagcgttcct tcatatgtac aaccaacgag tagaccagct tctgtaggta tttcctctgg    360
cagttctttg gcagtttctt ctcagcagct catgtcacct gcagcagcgc agcgaatatc    420
agccttgtct aattcccttg catcggccat agctggagga cgaataaatt atggagcttt    480
gtcaaattcc ctagctgcgg catctagaca gattcaaagt ggatcaggca tgtcaaaaac    540
ggaagccata gtcgaaactc ttctggaaac cttggctgct tgctggaaa ccatttctgg     600 ttccagcggt ggaggtcaaa ctgctcaaat gttacttcaa gcattagctt aaattttca    660 agtgcaccaa atggaaattt aggaagtgct tattctcaat tcaaagcagt gattaattaa    720
taaaggaatt tatgttccat attttaatt ttggttaagg gaaataaaa tgcaatgcaa     780 gcaaaaaaaa                                                            790
```

<210> SEQ ID NO 69
<211> LENGTH: 1862
<212> TYPE: DNA
<213> ORGANISM: Caerostris darwini

<400> SEQUENCE: 69

```
gtttgtgcta atgtaatagt tagtgcttgc gttaaggcga tgctaagttc aggagtatca     60
gtgtctgaca gtaactctca gcagattgcc tcccagcttt catcaacgat cgtagatgca    120
gtatgtggtg cagcaggtag agcgggcatg agaatacctg acagtgttgt gcagtctgac    180
aagaatttgg ttagccaaac aatcacctct atttccagta catcctcggc aacaacgaca    240
accacaactt cagttcaatc gaccgattca tcatcaagtt cgttctcggg actggattcc    300
acaggtggct ataccggaat accgagtgga ggatatcctg gtgaccccga ctatggccaa    360
ggttcggaca atgtccagag gcagttggta caaacgctta cagaagcact acaaggtact    420
cagtccatga gtttagtttc aagagcaaaa ttgttttcaa ttaatagtag ttaccggacc    480
gacttcgcaa gactagttag tgggccgatg aatttgggtg gctcggcgca aagtgaactg    540
cttgttagcc tagctggcat ttctcctaat tctgatgccc gtgtttgtgc taatgtaata    600
gttagtgctt gcgttaaggc gatgctaagt tcaggagtat cagtgtctga cagtaactct    660
cagcagattg cctcccagct ttcatcaacg atcgtagatg cagtatgtgg tgcagcaggc    720
agagcgggca tgagaatacc tgacagtgtt gtgcagtctg acaagaattt ggttagccaa    780
acaatctcct ctatttccag tacatcctcg gcaacaacga caaccacaac atcagttcaa    840
tcgaccgatt catcatcaag ttcgttctcg ggactggatt ccacaggtgg ctataccgga    900
ataccgagtg gaggatatcc tggtggaccc gactatggcc aaggttcgga caatgtccag    960
```

```
aggcagttgg tacaaacgct tacagaagca ctacaaggta ctcagtccat gaaattagtt    1020
ttcggtgcac aattgtttcc aaataatagt ttccggaccg agttcgcaag actagttagt    1080
gggtcgatga atttgggtgg ctcggcgtca agtgaactgc ttgttagcct agctggcatt    1140
tctcctactt ctgatgcccg tgtttctttt aaagtattgg ttagtgcttg tgttggggcg    1200
atgctaagtt caggagtatc agtgtctgac agtaactgtc agcagattgc ctcccagctt    1260
tcatcaacga tcgtagatgc agtatgtggt gcagcaggta gagcgggcgt gagaatacct    1320
gacagtgttg tgcagtctga caagaatttg gttagccaaa ctatttccag tacatcctcg    1380
gcaacaacga caagcgcaac atcagttcaa tcgaccgatt tatcatcaag ttcgttcttg    1440
ggacaggatt ccacaggtgt cagctcaagt acatctgtat ctagtatcat taattctcca    1500
aatggactga agtcaccgca agccaatgca agaatcaact cgttggcttc attgtttaac    1560
aatgctattg gttctaacgg tgtgcagatc gacgctgttt cccaaggact tgccggaatc    1620
atgtccaatc tgaagagatc tggaatgtca cctacccaag cgcaggtgga agctttggtg    1680
gagatgaact gcgctttgct aaagattgtt gtcgcctctc agggtggcag tccgaattct    1740
gtatcttcct cttctatgac atctttgctc tctgttatgt tgtgaaatat gactgctttt    1800
caataagtaa tgtctttaat tggaataata ataatcttta ataaatgcat tcaggaaaaa    1860
ac                                                                    1862

<210> SEQ ID NO 70
<211> LENGTH: 1990
<212> TYPE: DNA
<213> ORGANISM: Caerostris darwini

<400> SEQUENCE: 70
aaattcattg ttccaaatgg tgcattctct actccaggtt ctatacctgg tcctgatgga      60
aaacccattc atgttcagcc tgctggacct ggaaccacac caggagcaat aacagactct     120
gatggagatg tagtacaaat attttttgcca agtactccag cacctaaacc tgtaaatcca     180
acgacgccta cagctataac tggacctaaa ggaaatccaa ttgttatcta tccggctgga     240
ccaggaacaa caccccggaac agtgacagga ccagatggca aacctacaca gtttatagta     300
ccattaggag ctttctccac tccaggttcg attcctggac ctgatggaaa accaataccc     360
gtcgaaccag ctggtccagg caccacgcca ggaacgctaa ctgatccaga tggaagagta     420
aatagaattt atttgcctac aactcctgct cctccatcat accaaccaca agttccactt     480
accacaacgc ctataccagg tcccggacct caaccgatcc agatcatacc tgcgggccct     540
ggaacaacac cgggaactgt tacaggacca gacggaaggc caacacaatt tatagtcccg     600
caaggagcat ttagcactcc tggaactatt cctggtgctg atggtaaacc cattcctgtc     660
gaaccagcag gacctggaat gactccaggt gctcaaactg gacctgatgg aaaaataact     720
agaatagttc tgcctacaac tactcctctc ccaccacctc ctggaccgtt gaatcctgat     780
ggtttacctg ttgcaccttt tgggcccggg aacagtccta attatcaatc acccggtggt     840
tatccaggat ccaatttcc aggttaccca ggtgctccag gatcagatgg tccaacaagg     900
tacataaatt ccaatgagtt acctagtggt gagactccag atggatattt gaatgttgat     960
tccctcccag actttgtcac tccgggtttc cctcaaagtc ctttaggtta cttggatttc    1020
agtcagttgc ctgataatta cagtccagac tttccgggtc aactggtttt ccccggatac    1080
cctaattccc ctggaaacgg aagaaacact ccaggcgggct ttttgagctt cccagacttc    1140
```

```
ccgaaagata tcaccaataa attgaatagt ccgttcagct tcccacaaat aattcaggct    1200
ctgcaacctc tgttccccgg aaacaccata aacatgggag ccattccgaa ggaccagttg    1260
cagaacattc ccggactgga cggcgactac aacaaccttc agattccaga catgggagac    1320
agcagccacc cgaccggcgg agtcttctac cttccggaac tcatacgtct cataagctac    1380
cttccggtgg gatctttccc aggacgcgga ccgggcacca tgaatccgga cggaacgtac    1440
agcgatccct tcgacttccc gggactgaac ggcgctcccg gatacatctg cgactatccg    1500
gataacggcg acgcgacgcc cgatctcggt caggaggtcc agggcacgaa ccagggtccg    1560
gtcggagacg tggaggacgc cgctccggga agcgacgacg acctgggggc cccggcaccc    1620
cagctcgaat cggacgagtc cgactgcgac gacgacgtct tcggcacctt caacaaggcg    1680
aggtcgtctc tgctcgacgt ggcctccagc acgggcgtgc agaccatcag tgatctgatg    1740
caggcgctca tctctggaat caacccgtac gagaacactg tcgactacaa cgacttcttc    1800
aacgagctct cgtccctgtt ctcgcaggtc cgagccggat ccgactcgca gggtcccaac    1860
aaggagttca taaagatcct gttcgaagcc ctcgtcgcca gctggaagc cctgaacgcc    1920 gccaaggtca acggcttcag ggacgtctcg gtgcccagcg ctctgcccgt gtacacgtcc    1980
ttcctgtccg                                                          1990

<210> SEQ ID NO 71
<211> LENGTH: 756
<212> TYPE: DNA
<213> ORGANISM: Caerostris darwini

<400> SEQUENCE: 71
ggctgtataa aaagacagga aaataacaga acggacattc ggacgagaac attcctcaga     60
gaaaatgagt tacttgactc gtctagcttt agcgctcctg gcggtgctca gcacccaggc    120
gatctttgca aatggccaga tcactccttg gtccaatacc agattagcag aagctttcat    180
taattccttt atgagtaaag ttggctattc tggagcattc actgcagaac agatggacga    240
tatgtccact gttagtgata ccattatgac tgcaatggac aaaatggcaa gcagtaacaa    300
gagttcaaaa tccaaacttc aagccctgaa catggccttc gcttcaacta tggcagaaat    360
agctgccacg gaagaaggtg gccaaagtat ggctgtgaag acaaatgcca taactgacgc    420 tcttctgct gccttcttag agacaacagg tcaagtaaat tatcagttta taatgaaat    480 aaagagctta gtatacatgt tagctcaaca aagcatgaat gatgtatatg cttcagctgg    540
aacagcatca ggcggtggct atggtcccgg tcctcaagga ccttctggac caggaccata    600
tggtccacga ggagtcagtg tagtgtctac ttcagtttct ggacctggac acaaggacc    660 gtcaggacca ggaccacagg gtccatatgg accaggacca cagggaccag gaccacaagg    720
accaggacca caaggaccag gaccacaagg accagg                              756

<210> SEQ ID NO 72
<211> LENGTH: 1008
<212> TYPE: DNA
<213> ORGANISM: Caerostris darwini

<400> SEQUENCE: 72
aagcaaagat aacaacacag agtacatggg gacattcaga cgagatcaat actcaattga     60
aatgtattcg tctactcgtc tagctcttac gcttctggcg gtgctttgca cccaagctat    120
tttcactgct gctcaagcac ccagcccatg ggagagcacg cgctcgcag agagattcat    180 ggcaagcttc ttagcggcaa ctgggcagag tggtgcattc acagctgaac agttggatga    240
```

```
catgtctaca attggagaca ccttatcatc tgcaatggac aaaatggcaa gaagtaataa    300
aagttcgaaa tcgaaactgc aagccttaaa tatggcattc gcctcatcta tggcagaaat    360
tgcagctgta gagcagggag gtcaaagtat agctgtgaaa acgaatgcca ttgagaacgc    420
cttgatatca gcatttatgc agacaacagg tgcagtaaac taccagtttg ttagcgaaat    480
tagaaattta gttaatatga tggcacaagc atctgcaaat gaagtatcct acgcatcagc    540
tggtggaagt gcggcagctt cagcatccgg aggatatggt ccaagttcac aaggcccatc    600
tggacctgga ggttattcaa gttcagtaag tgtaagtggg gtatatggtc ctggaccaca    660
aggacctgca cctcaaggac catcgggacc tacaccacaa ggaccacagg gaatttctag    720
ttctgtaagt gtaagtgggg tatatggtcc tggaccacaa ggaccagcac ctcaaggacc    780
atcgggaccg acaccacaag gcccacaggg aacatacagt tctgtaagtg taagtggggc    840
atacgggcca ggaccacaag gtccggcagg acaaggacca tccggacccg gacctcaagg    900
accaggagga gcagcagcag ctgcagcagc cgcaagtgga tatggaccag gtggacaagg    960
accatcagga tctggaggac agggaccatc tggacctgga ggttcttc                1008

<210> SEQ ID NO 73
<211> LENGTH: 1127
<212> TYPE: DNA
<213> ORGANISM: Caerostris darwini

<400> SEQUENCE: 73
ggcattcagt cgacaagacc aattatcaaa atgacttgga catctcgact tgcgctatca     60
ctcctagtgg cgatctgcac tcagagcatg tttgctctgg gtcaggacaa cactccgtgg    120
tccagtacag gcacggcaga gtcttttatg tcttctttca tgtctgcagc aggtaactca    180
ggagctttca cagctgacca attagacgac atgaacacca tcactgatac catcagatca    240
gcgatggaca aaatggctcg aagcaataag agttcaaaat ctaaattgca agctctaaac    300
atggcgttct cttctgcaat ggcggaaatt gctattgatg aaggtggaca aagtgttggt    360
tataagacag acgcaattgc tgatgcactc agtcaagcat ttttacagac aactggagtt    420
gtaaatggtg ctttttattaa cgaaatcaga agtttaatta gcatgtttgc tcaaaactcc    480
gcaaatgcaa ttggctctgg aggaagttca gcatctgtta gtgtagcagc ctcagcagga    540
gggggatatg gaggtcaagg ttcatacggc cctggacccc aaggaccatc cggacctgga    600
ccacaaggtg caggagcatc ttcagcgtcc gctgtctctg cagcaagtgg accgggagga    660
tacgcaccag gacctcaagg accatctgga ccacaaggac caggacaaag ttcataccag    720
tattctgtaa gcatatcaac tcaaggagga agtcaaggtg gatatggagg acaacaaggt    780
ggtgctggac aagtggata cggaggagga ttaggcggtc aaggagcagg agctgccgca    840
gctgctgctg ccgctggtgg tgcaggaggc ttaggcggac aaggaggaca aggaggcgga    900
caaggagccg gtggtgctgg tcaaggaggt tacggatctg gattaggagg acaaggtgga    960
ggagctgccg ctgctgctgc tgccgctggt ggtgcaggag gcttaggcgg acaaggagga   1020
caaggaggcg acaaggagcc cggtggtgct ggtcaaggag gttacggatc tggattagga   1080
ggacaaggtg gaggagctgc cgctgctgct gctgccgctg gtggtgc                 1127

<210> SEQ ID NO 74
<211> LENGTH: 1118
<212> TYPE: DNA
<213> ORGANISM: Caerostris darwini
```

<400> SEQUENCE: 74

```
gaaacaactc caattatgtc ttggacatct cgacatgcgc tattctatct actagtgatc      60
tgcactcaga gtgttcttgc tctgggtcgg aacaataacc cttggtccaa tccaagttcg     120
gcagagagtt ttatgaatta cttcatggat ggagtaacta actcaggaag ttttacacca     180
gaccaattag acgacatgtg cgtcatatgt gacaccatca aagccacgac agatagaatg     240
tcaagaagta acaagaatac tgaatcgagt ttgcaagccc tgaacatcgc atttgcatcc     300
gcagtggcag aaattgctgc agccgaaggt actgaaaata tcggaatgaa aaccggagct     360
atcacggatg ctctgagttc agcatttatg cagacaacag acaagttaa cacggaattc      420
gtcaatgaaa ttcgaagctt aataaatatg ttttcacaag tatcaaggaa taatatctct     480
caaggaggtc ttggtggtac tggagatgtt ggaggagcag gtggacgagg aggtttaagt     540
ggtgctggag gattaagtgg tcctagtgga ttaggaggaa caggtggaag aggaggattt     600
gcaggttctg gaggtggatt aggtgcatct gcatcatctg ctagttctgg tgggcctggt     660
ggttctggtc aaggaggata cggtggaagt ttaggtggac caggaggatt tggacgttct     720
ggaggtggat taggtggtgg cgatagtgct gcatctacat catctatagg ttctggtggg     780
cctggtggtt ctggtcaagg aggatatggt ggaagtttag gtggaccagg aggatttgga     840
cgctctggag gtggattagg tggtggcgat agtgctgcat ctgcatcatc tgtaggttct     900
ggtgggcctg atggttctgg gcctggagga taccgtggaa atatagatgg accaggagga     960
tttggacgtt ctggaggtgg attaggtggt ggcgatagtg ctgcatctgc atcatctgta    1020
ggttctggtc ggcctgatgg ttctgggcct ggaggatacg gtggaagttt aggtggacca    1080
ggaggatttg gacgttctgg aggtggatta ggtggtgg                            1118
```

<210> SEQ ID NO 75
<211> LENGTH: 1209
<212> TYPE: DNA
<213> ORGANISM: Caerostris darwini

<400> SEQUENCE: 75

```
aagcagaaaa acaacgcag agtacatggg gactcagtcg aatagtccga tcttcacaat       60
gatttggata gctcgacttg cactgttggt agcggtggcc ttctccactc agagccagtt     120
agccctgggt caagacaaca cgccatggtc aagcacatcg tctgctgaaa ggttcatgga     180
agccttcata ggaggagctc aaaacaccgg cgtattcaca gatggacaga ttagcgacat     240
gaaagatata attgacacca ttaaagcggc aatggaaaag atgaaaaata aaacaagaa     300
ttcaaaatcg gtgctgcaag ctttgaatat ggctttcgca tcgtctgtgt cggagattgc     360
tgtaaccgaa ggaagccaaa gcattgaggc aaagacaaac gcaatatctg acgcgctggc     420
ttcagcattt atgcagacta ccggatctgt aaaccaaggg ttcattaatg aaatgaaaac     480
gttggtaagc atgtttgctc aaacatcatt taacgatgtc tcctattcag atagctcagc     540
gtcttcgtca tcaggaggat atggttcacc gggaggatat aattcaggag tcctggtgc      600
agcttcagca gtttctacat ccagtgcttc tggtgcagct gaaccaatat tctatggaca     660
aggtccaagc gcctatcaat attcagtaag catttccacc caaagtgggg acaaggcgg      720
ttatgaagga ataggaggag taggaacagc atctgctgcc tcagccggag gaggaacagg     780
agcaggagaa gcggacaag gcgggtacgg tggaatcgga actgggtctt catcagctgc      840
agccgcagga gctggggtg caggtggatt tggtcctggc ggatacggaa tgggaggatt     900
aggaggcgcc ggatctgccg ctgcagcagc tggtggtgca ggtggaattg gacctggtgg     960
```

```
ttatggagga aatggaggac aaggaggagt tggttctgca tctgcagccg cagcaggagc      1020
tggtgggacc ggtggatttg gtcctggagg atacggagga ggaggattag gaggcgaagg      1080
agctgcatct gctgctgcag caggagctgg tggggccggt ggatttggtc atgcagcagg      1140
agctggtggt ccggatggat atggttctgg cggttacgga ggacgaggag gacagggcgg      1200
tgcgggagg                                                             1209

<210> SEQ ID NO 76
<211> LENGTH: 1230
<212> TYPE: DNA
<213> ORGANISM: Caerostris darwini

<400> SEQUENCE: 76
gacacaaccg ctagccgaaa gcattcaaca atgtcttggc ttccagctct atccttgtta       60
ttggtgcttt tagtaccaaa cactaatgct atttcagcat caaaggcctc ctttcaagat      120
gagggaacga cgatttattt gttgaggagt atcctcgaat atctgaggga atgcgatgtt      180
ttaaaaatcg accaagaaag tgatgccgtg aatgctttat tcgaagtaag tttgctgttc      240
cagaataacg taaaaatgag taagcgaaag caggccattg catctaaatt ggcaggcatt      300
ataatggaag gtttggaagg atcgaatgag actgcataca aacttgactg tgccactaac      360
gccatgattg ccgccatgga aaacacaagt ggtactgtgg acatgtcctt catagattcg      420
gtaaaagagt tagctgtggt aatgtataat aatgacatag aagcaaaatt ggaagaatta      480
gaagaagaac aagaagaact atatcaagag caactattgt cttcagtcat tccagaaagt      540
caaatttcaa ctgatcagtc ggattatgga tctatacaga ttcaaaatca gttggtagat      600
cagggtgtgt caagtataac tacttccaat gaaaatcaaa ttcaaacaca acaatcagtc      660
actaatcaaa ttcaactaac ttcaacagct gaaacacagt ctcaacaatc tgcgggaaca      720
acagcatccc aacaaagtta tatagatgga cagcaatcat atatttctca gcagcaatct      780
gctgaatccc aacagcaata cgccaacact caacagcaat ctgttgaatc acaacagcaa      840
tctgctgaat ctcaacagca atacgccaat tctcaacagc aagcaactgg atcaacacag      900
aactatgcta catcgcaaca aaatattcaa tcgtccaatt cctacgagga tcaatcaagt      960
atatctcaag ctcaagaagt ccaatcatcc tattcacaaa atcaatactc tgcctctcac     1020
cagcaagcaa cagataccct tcaacaaaca attgaatcgc agccacaata cacaagttca     1080
cagcagcaaa tccaacaatc gtccaatgaa tatagcgatc aatcgagttt aacacaatat     1140
caagtagaca gctcctctgc atccatctat tttcaaacag acgtagttca caaccgtgtg     1200
gctcagtcac tactatcatc gagtgtctta                                      1230

<210> SEQ ID NO 77
<211> LENGTH: 1860
<212> TYPE: DNA
<213> ORGANISM: Caerostris darwini

<400> SEQUENCE: 77
cattcagacg agatcaatac tcaattgaaa tgtattcgtc tactcgtcta gctcttacgc       60
ttctggcggt gctttgcacc caagctattt tcactgctgc tcaagcaccc agcccatggg      120
agagcacggc gctcgcagag agattcatgg caagcttctt agcggcaact gggcagagtg      180
gtgcattcac agctgaacag ttggatgaca tgtctacaat tggagacacc ttatcatctg      240
caatggacaa aatggcaaga agtaataaaa gttcgaaatc gaaactgcaa gccttaaata      300
```

```
tggcattcgc ctcatctatg gcagaaattg cagctgtaga gcaggaggt  caaagtatag    360 ctgtgaaaac gaatgccatt gagaacgcct tgatatcagc atttatgcag acaacaggtg    420
cagtaaacta ccagtttgtt agcgaaatta gaaatttagt taatatgatg gcacaagcat    480
ctgcaaatga agtatcctac gcatcagctg gtggaagtgc ggcagcttca gcatccggag    540
gatatggtcc aagttcacaa ggcccatctg gacctggagg ttattcaagt tcagtaagtg    600
taagtggggt atatggtcct ggaccacaag gacctgcacc tcaaggacca tcggaccta     660 caccacaagg accacaggga atttctagtt ctgtaagtgt aagtggggta tatggtcctg    720
gaccacaagg accagcacct caaggaccat cggaccgac  accacaaggc ccacagggaa    780
catacagttc tgtaagtgta agtggggcat acgggccagg accacaaggt ccggcaggac    840
aaggaccatc cggacccgga cctcaaggac caggaggagc agcagcagct gcagcagccg    900
caagtggata tggaccaggt ggacaaggtc catccggacc cggatctcaa ggacctggag    960
gacaaggacc atcaggacca ggatctcaag gaccaggagg acaaggacca tatggtccag   1020
gtggagcagc agcagctgca gcagccacag gtggatatgg acaaggaggt tatggatccg   1080
gacaaggtgg acaaggtgca ggatctgctg ctgctgcagc tgccgctggt ggtgctggtg   1140
gaagaggtgg ttacggagga caaggcggac aaggtgccgg tggtgccggt caaggtggtt   1200
acggatctgg attaggagga ctaggtggag gagctgctgc tgctgctgct gccgctggtg   1260
gtgcaggagg attaggcgga caaggaggtg acaaggtgca aggacaagga ggttatggat   1320
ccggacaagg tgggcaaggt gcaggatctg ctgctgctgc agctgcggct ggtggtgctg   1380
gtggacgtgg cggattggga ggacaaggtg caggacaagg aggttatggt tccggacaag   1440
gtggttatgg accaagtggg caaatacct  ctgctgctgc ggcggcctct cgtttatcat   1500
ctccagcagt cgcttcaaga gtttcctcca ctgtgtcctc attggtatca agcgggccaa   1560
caagtcaagg tgctttatca aatgctataa gcaatgccgt ctcccaaata agtgctagta   1620
atcctggtct ctctggatgt gatgtccttg ttcaagcatt gttagaaatt gtatcagctc   1680
ttgttcacat tcttggttct tctagtgtag gtcaagtgag ctacaatact gcaggccagt   1740
ctgctgcagt agttagtcaa tctatatcac aagctcttgg ctaagcattc aacttttttct   1800 tccaacacaa taattttctg ttatgttgaa tatctttcaa taaaggatga gcatattttg   1860
```

<210> SEQ ID NO 78
<211> LENGTH: 1747
<212> TYPE: DNA
<213> ORGANISM: Caerostris darwini

<400> SEQUENCE: 78

```
acattcggac gagaacattc ctcagagaaa atgagttact tgactcgtct agctttagcg     60
ctactggcgg tgctcagcac ccaggcgatc tttgcaaatg ccagatcac  tccttggtcc    120 aataccagat tagcagaagc tttcattaat tcctttatga gtaaagttgg ctattctgga    180
gcattcactg cagaacagat ggacgatatg tccactgtta gtgataccat tatgactgca    240
atggacaaaa tggcaagcag taacaagagt tcaaaatcca aacttcaagc cctgaacatg    300
gccttcgctt caactatggc agaaatagct gccacgaag  aaggtggcca agtatggct     360 gtgaagacaa atgccataac tgacgctctt tctgctgcct tcttagagac aacaggtcaa    420
gtaaattatc agtttataaa tgaaataaag agcttagtat acatgttagc tcaacaaagc    480
atgaatgatg tatatgcttc agctggaaca gcatcaggcg gtggctatgg tcccggtcct    540
caaggacctt ctggaccagg accatatggt ccacgaggag tcagtgtagt gtctacttca    600
```

```
gtttctggac ctggaccaca aggaccgtca ggaccaggac cacagggtcc atatggacca      660
ggaccacagg gaccaggacc acaaggacca ggaccacaag gaccaggacc gcaaggacct      720
tctggaccag gaccacaagg cccatatggt cccggtagtg tcagtgtagt gtctggttca      780
gtttctggcc ctggcccaca aggatcatca ggaccaggac cacagggacc atacggacca      840
ggaccacagg gaccagcgcc aaaaggacca ggaccacaag gacctggacc gcaaggatca      900
ggaccgcaag gaccttcagg accaggacca caagggccat atggtccagg tggtgtcagt      960
gtagtgtcca acacagtttc tggacctgga ccgtcaggac caggaccaca gggtccatat     1020
ggtccagcac cacagggacc aggaccacaa ggaccaggac cacagggacc aggaccacaa     1080
ggaccaggac acaaggacc ttcaggacaa ggtccgcaac gaccttcagg accacgacca     1140
caaggaccat atggaccagg cggtatcagt gtagtgtctg ctacagtttc cggccctgga     1200
ccacaaggac cttcaggacc aggaccacaa cgcccgtatg gaccaggacc agaaggccca     1260
ggccctcaag gagcaggacc acaaggacca ggtctgcaaa gaccttcagg accaggccca     1320
caaggaccct atggtccggg cccacgaggt ccttcatcta cccctgaatc tgcggcaata     1380
aatgcagctt ctcgtttgtc ctctcctgct gcgtcgtcta gggtatcttc tactgtttct     1440
caattagtct caagtggacc tcctaacagt gctgcagtat ctggtgctat aagtagtttt     1500
ggtatctcaa gttagtgcca gcaatccagg cctttccggt tgtgatattc tcgtccaagc     1560
tttgatggaa ttgttatctg ctttagttag tattgttggg tcttccagta tcggtcaggt     1620
taattatggt gcaagtggtc agtacgctca gttggttagc caagcaattg gtcaagcatt     1680
ttgatgcaat cttcgcggac tctttttttt aatacttctg tcttgtaaat tttaataaat     1740
atatgat                                                               1747
```

<210> SEQ ID NO 79
<211> LENGTH: 1363
<212> TYPE: DNA
<213> ORGANISM: Caerostris darwini

<400> SEQUENCE: 79

```
attctgacga gaacattcct cagaaaaaat gagttacttg actcgtctag ctttagcgct       60
cctggcggtg ctcagcaccc aggcgatctt tgcaaatggc cagaatcctt ggtccaatac      120
cggattagca gaagctttca ttaactcatt catgagtaaa gttggctatt ctggagcatt      180
cactgcagat cagatggacg atatgtccac tgttagtgat accattatgt cagcaatgga      240
caaaatggca agaagcaaca agagctcgaa atccaaactt caagccctga acatggcatt      300
cgcttcaact atggcagaaa tagctgccac agaagaaggt ggtcaaagta tgtctgtgaa      360
gacaaatgct ataactgacg ctctttctgc tgccttctta gagacaacag gtcaagtaaa      420
ctatcagttt ataaatgaaa taaagagctt agtctacatg ttagctcaac aaagcatgaa      480
tgatgtatat gcttcagctg gaacagcgtc aggcggtggc tatggtcccg gtcctcaagg      540
accttctgca ccaggaccat atggtccagg aggagtcagt gtagtgtctg cttcagtttc      600
tggacctgga ccacaaggac cgtcaggacc aggaccacag ggtccatatg gaccaggacc      660
acagggacca gcaccacaag gaccaggacc acaaggaccg tcaggaccag gaccacaggg      720
tccatatgga ccaggaccac aggaccaggt ccacgaggga ccaggaccac aaggaccagg      780
acctcaaggt ccaggaccgc agggaccttc aggaccagga ccacagggac catatggtcc      840
tggcggtgtc agtgtagtgt ctgcttcagt ttctggacct ggaccacaag gaccatccgg      900
```

-continued

```
tcctgcagtc aatgcagctg cacgtttgtc atctcctgat gcatcatcta gagtatcttc    960
aactgtttct caattagtat ctggtggacc aactagtggt gcagcagttt ctaatgcttt   1020
aagtagcttg gtatctcaag ttggagccag caatccaggc ctttcaggtt gtgatattct   1080
tgtccaagct tgatggaaa tgctttctgc tttagttagc atcgttggct cttccagtat    1140
tggtcaagtt aattatggcg caagtggtca atatactcag atgattggcc aagcaattgc   1200
tcaagcattt taatgaaact ttttaatgac ttgattttg aaattatcct gtcttgtaaa    1260
ttttaataaa tagtaagttt gaaagaagt ttttattga tttatattt agtacagaaa      1320 gctatgtgtg caaatatat gaataaaat ttaaatatta ttt                       1363
```

<210> SEQ ID NO 80
<211> LENGTH: 154
<212> TYPE: PRT
<213> ORGANISM: Caerostris darwini

<400> SEQUENCE: 80

Met Ser Tyr Leu Thr Arg Leu Ala Leu Ala Leu Leu Ala Val Leu Ser
1               5                   10                  15

Thr Gln Ala Ile Phe Ala Asn Gly Gln Ile Thr Pro Trp Ser Asn Thr
            20                  25                  30

Arg Leu Ala Glu Ala Phe Ile Asn Ser Phe Met Ser Lys Val Gly Tyr
        35                  40                  45

Ser Gly Ala Phe Thr Ala Glu Gln Met Asp Asp Met Ser Thr Val Ser
    50                  55                  60

Asp Thr Ile Met Thr Ala Met Asp Lys Met Ala Ser Ser Asn Lys Ser
65                  70                  75                  80

Ser Lys Ser Lys Leu Gln Ala Leu Asn Met Ala Phe Ala Ser Thr Met
                85                  90                  95

Ala Glu Ile Ala Ala Thr Glu Glu Gly Gly Gln Ser Met Ala Val Lys
            100                 105                 110

Thr Asn Ala Ile Thr Asp Ala Leu Ser Ala Ala Phe Leu Glu Thr Thr
        115                 120                 125

Gly Gln Val Asn Tyr Gln Phe Ile Asn Glu Ile Lys Ser Leu Val Tyr
    130                 135                 140

Met Leu Ala Gln Gln Ser Met Asn Asp Val
145                 150

<210> SEQ ID NO 81
<211> LENGTH: 153
<212> TYPE: PRT
<213> ORGANISM: Caerostris darwini

<400> SEQUENCE: 81

Met Ser Tyr Leu Thr Arg Leu Ala Leu Ala Leu Leu Ala Val Leu Ser
1               5                   10                  15

Thr Gln Ala Ile Phe Ala Asn Gly Gln Asn Pro Trp Ser Asn Thr Gly
            20                  25                  30

Leu Ala Glu Ala Phe Ile Asn Ser Phe Met Ser Lys Val Gly Tyr Ser
        35                  40                  45

Gly Ala Phe Thr Ala Asp Gln Met Asp Asp Met Ser Thr Val Ser Asp
    50                  55                  60

Thr Ile Met Ser Ala Met Asp Lys Met Ala Arg Ser Asn Lys Ser Ser
65                  70                  75                  80

Lys Ser Lys Leu Gln Ala Leu Asn Met Ala Phe Ala Ser Thr Met Ala
                85                  90                  95

```
Glu Ile Ala Ala Thr Glu Gly Gly Gln Ser Met Ser Val Lys Thr
            100                 105                 110

Asn Ala Ile Thr Asp Ala Leu Ser Ala Ala Phe Leu Glu Thr Thr Gly
        115                 120                 125

Gln Val Asn Tyr Gln Phe Ile Asn Glu Ile Lys Ser Leu Val Tyr Met
130                 135                 140

Leu Ala Gln Gln Ser Met Asn Asp Val
145                 150
```

<210> SEQ ID NO 82
<211> LENGTH: 155
<212> TYPE: PRT
<213> ORGANISM: Caerostris darwini

<400> SEQUENCE: 82

```
Met Tyr Ser Ser Thr Arg Leu Ala Leu Thr Leu Leu Ala Val Leu Cys
1               5                   10                  15

Thr Gln Ala Ile Phe Thr Ala Ala Gln Ala Pro Ser Pro Trp Glu Ser
            20                  25                  30

Thr Ala Leu Ala Glu Arg Phe Met Ala Ser Phe Leu Ala Ala Thr Gly
        35                  40                  45

Gln Ser Gly Ala Phe Thr Ala Glu Gln Leu Asp Asp Met Ser Thr Ile
50                  55                  60

Gly Asp Thr Leu Ser Ser Ala Met Asp Lys Met Ala Arg Ser Asn Lys
65                  70                  75                  80

Ser Ser Lys Ser Lys Leu Gln Ala Leu Asn Met Ala Phe Ala Ser Ser
            85                  90                  95

Met Ala Glu Ile Ala Ala Val Glu Gln Gly Gly Gln Ser Ile Ala Val
            100                 105                 110

Lys Thr Asn Ala Ile Glu Asn Ala Leu Ile Ser Ala Phe Met Gln Thr
        115                 120                 125

Thr Gly Ala Val Asn Tyr Gln Phe Val Ser Glu Ile Arg Asn Leu Val
    130                 135                 140

Asn Met Met Ala Gln Ala Ser Ala Asn Glu Val
145                 150                 155
```

<210> SEQ ID NO 83
<211> LENGTH: 154
<212> TYPE: PRT
<213> ORGANISM: Caerostris darwini

<400> SEQUENCE: 83

```
Met Thr Trp Thr Ser Arg Leu Ala Leu Ser Leu Leu Val Ala Ile Cys
1               5                   10                  15

Thr Gln Ser Met Phe Ala Leu Gly Gln Asp Asn Thr Pro Trp Ser Ser
            20                  25                  30

Thr Gly Thr Ala Glu Ser Phe Met Ser Ser Phe Met Ser Ala Ala Gly
        35                  40                  45

Asn Ser Gly Ala Phe Thr Ala Asp Gln Leu Asp Asp Met Asn Thr Ile
50                  55                  60

Thr Asp Thr Ile Arg Ser Ala Met Asp Lys Met Ala Arg Ser Asn Lys
65                  70                  75                  80

Ser Ser Lys Ser Lys Leu Gln Ala Leu Asn Met Ala Phe Ser Ser Ala
            85                  90                  95

Met Ala Glu Ile Ala Ile Asp Glu Gly Gly Gln Ser Val Gly Tyr Lys
            100                 105                 110
```

```
Thr Asp Ala Ile Ala Asp Ala Leu Ser Gln Ala Phe Leu Gln Thr Thr
        115                 120                 125

Gly Val Val Asn Gly Ala Phe Ile Asn Glu Ile Arg Ser Leu Ile Ser
130                 135                 140

Met Phe Ala Gln Asn Ser Ala Asn Ala Ile
145                 150

<210> SEQ ID NO 84
<211> LENGTH: 155
<212> TYPE: PRT
<213> ORGANISM: Caerostris darwini

<400> SEQUENCE: 84

Met Ser Trp Thr Ser Arg His Ala Leu Phe Tyr Leu Val Ile Cys
1               5                   10                  15

Thr Gln Ser Val Leu Ala Leu Gly Arg Asn Asn Pro Trp Ser Asn
                20                  25                  30

Pro Ser Ser Ala Glu Ser Phe Met Asn Tyr Phe Met Asp Gly Val Thr
                35                  40                  45

Asn Ser Gly Ser Phe Thr Pro Asp Gln Leu Asp Asp Met Cys Val Ile
50                  55                  60

Cys Asp Thr Ile Lys Ala Thr Thr Asp Arg Met Ser Arg Ser Asn Lys
65                  70                  75                  80

Asn Thr Glu Ser Ser Leu Gln Ala Leu Asn Ile Ala Phe Ala Ser Ala
                85                  90                  95

Val Ala Glu Ile Ala Ala Ala Glu Gly Thr Glu Asn Ile Gly Met Lys
                100                 105                 110

Thr Gly Ala Ile Thr Asp Ala Leu Ser Ser Ala Phe Met Gln Thr Thr
        115                 120                 125

Gly Gln Val Asn Thr Glu Phe Val Asn Glu Ile Arg Ser Leu Ile Asn
130                 135                 140

Met Phe Ser Gln Val Ser Arg Asn Asn Ile Ser
145                 150                 155

<210> SEQ ID NO 85
<211> LENGTH: 154
<212> TYPE: PRT
<213> ORGANISM: Caerostris darwini

<400> SEQUENCE: 85

Met Ile Trp Ile Ala Arg Leu Ala Leu Leu Val Ala Val Ala Phe Ser
1               5                   10                  15

Thr Gln Ser Gln Leu Ala Leu Gly Gln Asp Asn Thr Pro Trp Ser Ser
                20                  25                  30

Thr Ser Ser Ala Glu Arg Phe Met Glu Ala Phe Ile Gly Gly Ala Gln
                35                  40                  45

Asn Thr Gly Val Phe Thr Asp Gly Gln Ile Ser Asp Met Lys Asp Ile
                50                  55                  60

Ile Asp Thr Ile Lys Ala Ala Met Glu Lys Met Lys Asn Lys Asn Lys
65                  70                  75                  80

Asn Ser Lys Ser Val Leu Gln Ala Leu Asn Met Ala Phe Ala Ser Ser
                85                  90                  95

Val Ser Glu Ile Ala Val Thr Glu Gly Ser Gln Ser Ile Glu Ala Lys
                100                 105                 110

Thr Asn Ala Ile Ser Asp Ala Leu Ala Ser Ala Phe Met Gln Thr Thr
        115                 120                 125
```

-continued

```
Gly Ser Val Asn Gln Gly Phe Ile Asn Glu Met Lys Thr Leu Val Ser
            130                 135                 140

Met Phe Ala Gln Thr Ser Phe Asn Asp Val
145                 150

<210> SEQ ID NO 86
<211> LENGTH: 97
<212> TYPE: PRT
<213> ORGANISM: Caerostris darwini

<400> SEQUENCE: 86

Ser Arg Leu Ser Ser Pro Ala Ala Ser Ser Arg Val Ser Ser Thr Val
1               5                   10                  15

Ser Gln Leu Val Ser Ser Gly Pro Pro Asn Ser Ala Ala Val Ser Gly
            20                  25                  30

Ala Ile Ser Ser Leu Val Ser Gln Val Ser Ala Ser Asn Pro Gly Leu
        35                  40                  45

Ser Gly Cys Asp Ile Leu Val Gln Ala Leu Met Glu Leu Leu Ser Ala
    50                  55                  60

Leu Val Ser Ile Val Gly Ser Ser Ile Gly Gln Val Asn Tyr Gly
65                  70                  75                  80

Ala Ser Gly Gln Tyr Ala Gln Leu Val Ser Gln Ala Ile Gly Gln Ala
                85                  90                  95

Phe

<210> SEQ ID NO 87
<211> LENGTH: 97
<212> TYPE: PRT
<213> ORGANISM: Caerostris darwini

<400> SEQUENCE: 87

Ala Arg Leu Ser Ser Pro Asp Ala Ser Ser Arg Val Ser Ser Thr Val
1               5                   10                  15

Ser Gln Leu Val Ser Gly Gly Pro Thr Ser Gly Ala Ala Val Ser Asn
            20                  25                  30

Ala Leu Ser Ser Leu Val Ser Gln Val Gly Ala Ser Asn Pro Gly Leu
        35                  40                  45

Ser Gly Cys Asp Ile Leu Val Gln Ala Leu Met Glu Met Leu Ser Ala
    50                  55                  60

Leu Val Ser Ile Val Gly Ser Ser Ser Ile Gly Gln Val Asn Tyr Gly
65                  70                  75                  80

Ala Ser Gly Gln Tyr Thr Gln Met Ile Gly Gln Ala Ile Ala Gln Ala
                85                  90                  95

Phe

<210> SEQ ID NO 88
<211> LENGTH: 98
<212> TYPE: PRT
<213> ORGANISM: Caerostris darwini

<400> SEQUENCE: 88

Ser Arg Leu Ser Ser Pro Ala Val Ala Ser Arg Val Ser Ser Thr Val
1               5                   10                  15

Ser Ser Leu Val Ser Ser Gly Pro Thr Ser Gln Gly Ala Leu Ser Asn
            20                  25                  30

Ala Ile Ser Asn Ala Val Ser Gln Ile Ser Ala Ser Asn Pro Gly Leu
        35                  40                  45
```

```
Ser Gly Cys Asp Val Leu Val Gln Ala Leu Leu Glu Ile Val Ser Ala
 50                  55                  60

Leu Val His Ile Leu Gly Ser Ser Val Gly Gln Val Ser Tyr Asn
 65                  70                  75                  80

Thr Ala Gly Gln Ser Ala Ala Val Val Ser Gln Ser Ile Ser Gln Ala
                 85                  90                  95

Leu Gly

<210> SEQ ID NO 89
<211> LENGTH: 98
<212> TYPE: PRT
<213> ORGANISM: Caerostris darwini

<400> SEQUENCE: 89

Ser Arg Leu Ser Ser Pro Ala Ala Ser Ser Arg Val Ser Ala Val
 1               5                  10                  15

Ser Ser Leu Val Ser Ser Gly Pro Thr Ser Pro Ala Ala Leu Ser Asn
                 20                  25                  30

Thr Ile Ser Asn Val Val Ser Gln Val Gly Ala Ser Asn Pro Gly Leu
             35                  40                  45

Ser Gly Cys Asp Val Leu Val Gln Ala Leu Leu Glu Ile Val Ser Ala
 50                  55                  60

Leu Ile His Ile Leu Gly Ser Ser Ile Gly Gln Val Asn Tyr Gly
 65                  70                  75                  80

Ala Thr Ala Gln Ser Thr Gly Ile Val Ser Gln Ser Ile Ser Gln Ala
                 85                  90                  95

Leu Gly

<210> SEQ ID NO 90
<211> LENGTH: 98
<212> TYPE: PRT
<213> ORGANISM: Caerostris darwini

<400> SEQUENCE: 90

Ser Arg Leu Ser Ser Pro Asp Ala Ser Ser Arg Val Ser Ser Ala Val
 1               5                  10                  15

Ser Ser Leu Val Ser Ser Gly Pro Thr Asn Pro Ala Ala Leu Ser Asn
                 20                  25                  30

Thr Ile Gly Ser Val Val Ser Gln Ile Gly Ala Ser Asn Pro Gly Leu
             35                  40                  45

Ser Gly Cys Asp Ile Leu Val Gln Ala Leu Leu Glu Ile Val Ser Ala
 50                  55                  60

Leu Ile Gln Ile Leu Ala Ser Ser Ser Ile Gly His Val Asn Tyr Gly
 65                  70                  75                  80

Ala Thr Ala Gln Ser Thr Gly Ile Val Ser Gln Ser Ile Ser Gln Ala
                 85                  90                  95

Leu Gly

<210> SEQ ID NO 91
<211> LENGTH: 97
<212> TYPE: PRT
<213> ORGANISM: Caerostris darwini

<400> SEQUENCE: 91

Ser Arg Leu Tyr Ser Pro Asp Ser Ser Ala Arg Ile Ser Ala Val
 1               5                  10                  15
```

```
Ser Ser Leu Ala Ser Tyr Gly Pro Asn Asn Pro Thr Ala Leu Ser Asp
            20              25                  30

Val Ile Ser Asn Thr Met Ser Gln Val Ser Tyr Ser Ser Pro Glu Leu
            35              40                  45

Ser Gly Cys Asp Val Leu Val Gln Thr Leu Met Glu Val Val Ser Ala
            50              55                  60

Leu Val His Ile Leu Ser Val Ser Asp Ile Gly Pro Val Ala Tyr Asp
65              70                  75                      80

Ser Asp Gln Ala Val Gln Val Val Gly Gln Ser Phe Asn Asn Leu Met
                85              90                  95

Tyr

<210> SEQ ID NO 92
<211> LENGTH: 98
<212> TYPE: PRT
<213> ORGANISM: Caerostris darwini

<400> SEQUENCE: 92

Ser Arg Leu Ser Ser Pro Glu Ala Ser Ser Arg Ile Ser Ser Val Val
1               5                   10                  15

Ser Ser Phe Leu Ser Asn Gly Ile Asp Asn Pro Ser Ser Leu Ser Ser
            20              25                  30

Ser Leu Ser Gly Ile Val Ser Arg Ile Ser Ser Leu Asn Pro Met Leu
            35              40                  45

Ser Ser Cys Asp Ile Leu Leu Gln Ala Leu Leu Glu Ile Val Ser Ala
            50              55                  60

Leu Leu Gln Ile Leu Ala Ser Ser Asn Ile Gly Pro Ile Asp Tyr Ser
65              70                  75                      80

Ser Thr Arg Gln Ser Thr Gly Ile Val Ser Gln Ser Val Tyr Gln Ala
                85              90                  95

Phe Ser
```